(12) United States Patent
Owen et al.

(10) Patent No.: US 11,853,691 B2
(45) Date of Patent: *Dec. 26, 2023

(54) AUTOMATED CLINICAL DOCUMENTATION SYSTEM AND METHOD

(71) Applicant: Nuance Communications, Inc., Burlington, MA (US)

(72) Inventors: Donald E. Owen, Orlando, FL (US);
Uwe Helmut Jost, Groton, MA (US);
Daniel Paulino Almendro Barreda, London (GB); Dushyant Sharma, Woburn, MA (US)

(73) Assignee: Nuance Communications, Inc., Burlington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/210,052

(22) Filed: Mar. 23, 2021

(65) Prior Publication Data
US 2021/0210180 A1 Jul. 8, 2021

Related U.S. Application Data

(63) Continuation of application No. 16/058,912, filed on Aug. 8, 2018, now Pat. No. 10,957,427.
(Continued)

(51) Int. Cl.
*G16H 10/60* (2018.01)
*A61B 5/00* (2006.01)
(Continued)

(52) U.S. Cl.
CPC .......... *G16H 10/60* (2018.01); *A61B 5/7405* (2013.01); *G06F 3/16* (2013.01); *G06F 16/637* (2019.01);
(Continued)

(58) Field of Classification Search
USPC ................................. 386/223–224, 239–248
See application file for complete search history.

(56) References Cited

U.S. PATENT DOCUMENTS

| 5,357,427 A | 10/1994 | Langen et al. |
| 5,805,747 A | 9/1998 | Bradford |

(Continued)

FOREIGN PATENT DOCUMENTS

| JP | 2011182857 A | 9/2011 |
| KR | 20130118510 A | 10/2013 |

(Continued)

OTHER PUBLICATIONS

Non-Final Office Action issued in U.S. Appl. No. 16/059,944 dated Sep. 28, 2018.
(Continued)

*Primary Examiner* — Hung Q Dang
(74) *Attorney, Agent, or Firm* — Brian J. Colandreo; Heath M. Sargeant; Holland & Knight LLP

(57) ABSTRACT

A method, computer program product, and computing system for synchronizing machine vision and audio is executed on a computing device and includes obtaining encounter information of a patient encounter, wherein the encounter information includes machine vision encounter information and audio encounter information. The machine vision encounter information and the audio encounter information are temporally-aligned to produce a temporarily-aligned encounter recording.

18 Claims, 29 Drawing Sheets

Related U.S. Application Data

(60) Provisional application No. 62/638,809, filed on Mar. 5, 2018, provisional application No. 62/543,762, filed on Aug. 10, 2017.

(51) Int. Cl.

| | |
|---|---|
| *G06F 3/16* | (2006.01) |
| *G06F 16/635* | (2019.01) |
| *G06F 16/683* | (2019.01) |
| *G06F 16/904* | (2019.01) |
| *G06F 21/62* | (2013.01) |
| *G06F 40/174* | (2020.01) |
| *G06F 40/30* | (2020.01) |
| *G06F 40/40* | (2020.01) |
| *G06K 9/62* | (2022.01) |
| *G06K 19/077* | (2006.01) |
| *G06N 3/00* | (2006.01) |
| *G06T 7/00* | (2017.01) |
| *G06V 20/10* | (2022.01) |
| *H04R 3/12* | (2006.01) |
| *G16H 40/20* | (2018.01) |
| *G10L 17/00* | (2013.01) |
| *G16Y 20/00* | (2020.01) |
| *G06V 20/52* | (2022.01) |
| *G06V 40/16* | (2022.01) |
| *G06V 40/20* | (2022.01) |
| *G06V 40/10* | (2022.01) |
| *H04L 51/222* | (2022.01) |
| *G06F 18/25* | (2023.01) |
| *G16H 50/30* | (2018.01) |
| *G16H 80/00* | (2018.01) |
| *G16H 30/00* | (2018.01) |
| *G16H 40/63* | (2018.01) |
| *H04N 7/18* | (2006.01) |
| *H04R 3/00* | (2006.01) |
| *G16H 10/20* | (2018.01) |
| *H04R 1/32* | (2006.01) |
| *G16H 15/00* | (2018.01) |
| *H04L 51/02* | (2022.01) |
| *G16H 40/60* | (2018.01) |
| *G16H 30/20* | (2018.01) |
| *G16H 30/40* | (2018.01) |
| *G10L 21/0232* | (2013.01) |
| *G16H 50/20* | (2018.01) |
| *G06N 3/006* | (2023.01) |
| *G16B 50/00* | (2019.01) |
| *G10L 15/08* | (2006.01) |
| *G11B 27/10* | (2006.01) |
| *H04R 3/02* | (2006.01) |
| *G10L 15/26* | (2006.01) |
| *H04R 1/40* | (2006.01) |
| *G10L 15/22* | (2006.01) |
| *G10L 21/0208* | (2013.01) |
| *G10L 15/18* | (2013.01) |

(52) U.S. Cl.
CPC .......... *G06F 16/685* (2019.01); *G06F 16/904* (2019.01); *G06F 18/25* (2023.01); *G06F 21/6245* (2013.01); *G06F 40/174* (2020.01); *G06F 40/30* (2020.01); *G06F 40/40* (2020.01); *G06K 19/07762* (2013.01); *G06N 3/006* (2013.01); *G06T 7/00* (2013.01); *G06V 20/10* (2022.01); *G06V 20/52* (2022.01); *G06V 40/103* (2022.01); *G06V 40/16* (2022.01); *G06V 40/172* (2022.01); *G06V 40/23* (2022.01); *G10L 15/08* (2013.01); *G10L 17/00* (2013.01); *G10L 21/0232* (2013.01); *G11B 27/10* (2013.01); *G16B 50/00* (2019.02); *G16H 10/20* (2018.01); *G16H 15/00* (2018.01); *G16H 30/00* (2018.01); *G16H 30/20* (2018.01); *G16H 30/40* (2018.01); *G16H 40/20* (2018.01); *G16H 40/60* (2018.01); *G16H 40/63* (2018.01); *G16H 50/20* (2018.01); *G16H 50/30* (2018.01); *G16H 80/00* (2018.01); *G16Y 20/00* (2020.01); *H04L 51/02* (2013.01); *H04L 51/222* (2022.05); *H04N 7/183* (2013.01); *H04R 1/326* (2013.01); *H04R 3/005* (2013.01); *H04R 3/12* (2013.01); *G06T 2207/10024* (2013.01); *G06T 2207/10044* (2013.01); *G06T 2207/10048* (2013.01); *G06T 2207/10116* (2013.01); *G06T 2207/10132* (2013.01); *G10L 15/1815* (2013.01); *G10L 15/22* (2013.01); *G10L 15/26* (2013.01); *G10L 2021/02082* (2013.01); *H04N 7/181* (2013.01); *H04R 1/406* (2013.01); *H04R 3/02* (2013.01); *H04R 2420/07* (2013.01); *H04S 2400/15* (2013.01)

(56) References Cited

U.S. PATENT DOCUMENTS

| | | |
|---|---|---|
| 5,809,476 A | 9/1998 | Ryan |
| 5,940,118 A | 8/1999 | Van Schyndel |
| 5,970,455 A * | 10/1999 | Wilcox ............... G06F 3/0488 |
| | | 704/270 |
| 5,970,457 A | 10/1999 | Brant et al. |
| 6,004,276 A | 12/1999 | Wright |
| 6,031,526 A | 2/2000 | Shipp |
| 6,266,635 B1 | 7/2001 | Sneh |
| 6,332,122 B1 | 12/2001 | Ortega et al. |
| 6,401,063 B1 | 6/2002 | Hebert et al. |
| 6,405,165 B1 | 6/2002 | Blum et al. |
| 6,434,520 B1 | 8/2002 | Kanevsky et al. |
| 6,523,166 B1 | 2/2003 | Mishra et al. |
| 6,589,169 B1 | 7/2003 | Surwit et al. |
| 6,801,916 B2 | 10/2004 | Roberge et al. |
| 6,823,203 B2 | 11/2004 | Jordan |
| 6,847,336 B1 | 1/2005 | Lemelson et al. |
| 6,915,254 B1 | 7/2005 | Heinze et al. |
| 7,236,618 B1 | 6/2007 | Chui et al. |
| 7,298,930 B1 | 11/2007 | Erol et al. |
| 7,412,396 B1 | 8/2008 | Haq |
| 7,493,253 B1 | 2/2009 | Ceusters et al. |
| 7,496,500 B2 | 2/2009 | Reed et al. |
| 7,516,070 B2 | 4/2009 | Kahn |
| 7,558,156 B2 | 7/2009 | Vook et al. |
| 7,817,805 B1 | 10/2010 | Griffin |
| 7,830,962 B1 | 11/2010 | Fernandez |
| 8,132,104 B2 | 3/2012 | Ash et al. |
| 8,214,082 B2 | 7/2012 | Tsai et al. |
| 8,345,887 B1 | 1/2013 | Betbeder |
| 8,369,593 B2 | 2/2013 | Peng et al. |
| 8,589,177 B2 | 11/2013 | Haq |
| 8,589,372 B2 | 11/2013 | Krislov |
| 8,606,594 B2 | 12/2013 | Stern et al. |
| 8,661,012 B1 | 2/2014 | Baker et al. |
| 8,843,372 B1 | 9/2014 | Isenberg |
| 8,983,889 B1 | 3/2015 | Stoneman |
| 9,104,985 B2 | 8/2015 | Drucker et al. |
| 9,146,301 B2 | 9/2015 | Adcock et al. |
| 9,224,180 B2 | 12/2015 | Macoviak et al. |
| 9,270,964 B1 | 2/2016 | Tseytlin |
| 9,293,151 B2 | 3/2016 | Herbig et al. |
| 9,326,143 B2 | 4/2016 | McFarland |
| 9,338,493 B2 | 10/2016 | Van Os et al. |
| 9,479,931 B2 | 10/2016 | Ortiz et al. |
| 9,509,676 B1 | 11/2016 | Johnson et al. |
| 9,536,049 B2 | 1/2017 | Brown et al. |

(56) References Cited

U.S. PATENT DOCUMENTS

| | | |
|---|---|---|
| 9,536,106 B2 | 1/2017 | Fram |
| 9,569,593 B2 | 2/2017 | Casella dos Santos |
| 9,668,006 B2 | 5/2017 | Betts et al. |
| 9,668,024 B2 | 5/2017 | Os et al. |
| 9,668,066 B1 | 5/2017 | Betts et al. |
| 9,679,102 B2 | 6/2017 | Cardoza et al. |
| 9,679,107 B2 | 6/2017 | Cardoza et al. |
| 9,569,594 B2 | 10/2017 | Casella dos Santos |
| 9,779,631 B1 | 10/2017 | Miller et al. |
| 9,785,753 B2 | 10/2017 | Casella dos Santos |
| 9,799,206 B1 | 10/2017 | Wilson Van Horn et al. |
| 9,824,691 B1 | 11/2017 | Montero et al. |
| RE47,049 E | 9/2018 | Zhu |
| 10,090,068 B2 | 10/2018 | Kusens et al. |
| 10,212,588 B2 | 2/2019 | Grim et al. |
| 10,219,083 B2 | 2/2019 | Farmani et al. |
| 10,354,054 B2 | 7/2019 | Kobres et al. |
| 10,423,948 B1 | 9/2019 | Wilson et al. |
| 10,440,498 B1 | 10/2019 | Amengual Gari et al. |
| 10,491,598 B2 | 11/2019 | Leblang et al. |
| 10,546,655 B2 | 1/2020 | Owen et al. |
| 10,559,295 B1 | 2/2020 | Abel |
| 10,650,824 B1 | 5/2020 | Kesharaju et al. |
| 10,691,783 B2 | 6/2020 | Frempong et al. |
| 10,693,872 B1 | 6/2020 | Larson et al. |
| 10,701,081 B2 | 6/2020 | Grim et al. |
| 10,719,222 B1 | 7/2020 | Strader |
| 10,785,565 B2 | 9/2020 | Mate et al. |
| 10,803,436 B2 | 10/2020 | Kobres et al. |
| 10,810,574 B1 | 10/2020 | Wilson et al. |
| 10,957,428 B2 | 3/2021 | Owen et al. |
| 10,972,682 B1 | 4/2021 | Muenster |
| 10,978,187 B2 | 4/2021 | Owen et al. |
| 11,043,288 B2 | 6/2021 | Gallopyn et al. |
| 11,074,996 B2 | 7/2021 | Gallopyn et al. |
| 11,101,022 B2 | 8/2021 | Owen |
| 11,101,023 B2 | 8/2021 | Gallopyn et al. |
| 11,114,186 B2 | 9/2021 | Owen |
| 11,177,034 B2 | 11/2021 | Lyman et al. |
| 11,216,480 B2 | 1/2022 | Oz et al. |
| 11,222,103 B1 | 1/2022 | Gallopyn et al. |
| 11,222,716 B2 | 1/2022 | Vozila et al. |
| 11,227,588 B2 | 1/2022 | Wolff et al. |
| 11,227,679 B2 | 1/2022 | Owen et al. |
| 11,238,226 B2 | 2/2022 | Vozila et al. |
| 11,250,382 B2 | 2/2022 | Sharma et al. |
| 11,250,383 B2 | 2/2022 | Sharma et al. |
| 11,257,576 B2 | 2/2022 | Owen et al. |
| 11,270,261 B2 | 3/2022 | Vozila |
| 11,295,838 B2 | 4/2022 | Owen et al. |
| 11,295,839 B2 | 4/2022 | Owen et al. |
| 11,316,865 B2 | 4/2022 | Gallopyn et al. |
| 11,322,231 B2 | 5/2022 | Owen et al. |
| 11,368,454 B2 | 6/2022 | Whaley et al. |
| 11,402,976 B1 | 8/2022 | Palamadai et al. |
| 11,483,707 B2 | 10/2022 | Leblang et al. |
| 11,538,567 B2 | 12/2022 | Davies |
| 2001/0029322 A1 | 10/2001 | Iliff |
| 2001/0041992 A1 | 11/2001 | Lewis et al. |
| 2001/0042114 A1 | 11/2001 | Agraharam et al. |
| 2002/0032583 A1 | 3/2002 | Joao |
| 2002/0069056 A1 | 6/2002 | Nofsinger |
| 2002/0072896 A1 | 6/2002 | Roberge et al. |
| 2002/0082825 A1 | 6/2002 | Rowlandson et al. |
| 2002/0143533 A1 | 10/2002 | Lucas et al. |
| 2002/0170565 A1 | 11/2002 | Walker et al. |
| 2002/0178002 A1 | 11/2002 | Boguraev et al. |
| 2002/0194005 A1 | 12/2002 | Lahr |
| 2003/0028401 A1 | 2/2003 | Kaufman et al. |
| 2003/0051214 A1 | 3/2003 | Graham et al. |
| 2003/0105631 A1 | 6/2003 | Habte |
| 2003/0105638 A1 | 6/2003 | Taira |
| 2003/0125940 A1 | 7/2003 | Basson et al. |
| 2003/0154085 A1 | 8/2003 | Kelley |
| 2003/0185411 A1 | 10/2003 | Atlas et al. |
| 2003/0216937 A1 | 11/2003 | Schreiber et al. |
| 2004/0078228 A1 | 4/2004 | Fitzgerald et al. |
| 2004/0122701 A1 | 6/2004 | Dahlin et al. |
| 2004/0128323 A1 | 7/2004 | Walker |
| 2004/0162728 A1 | 8/2004 | Thomson et al. |
| 2004/0167644 A1 | 8/2004 | Swinney |
| 2004/0172070 A1 | 9/2004 | Moore et al. |
| 2004/0186712 A1 | 9/2004 | Coles et al. |
| 2004/0243545 A1 | 12/2004 | Boone et al. |
| 2004/0247016 A1 | 12/2004 | Faries, Jr. et al. |
| 2005/0055215 A1 | 3/2005 | Klotz |
| 2005/0075543 A1 | 4/2005 | Calabrese |
| 2005/0114179 A1* | 5/2005 | Brackett ................ G16H 10/60 705/2 |
| 2005/0154588 A1 | 7/2005 | Janas et al. |
| 2005/0165285 A1 | 7/2005 | Lift |
| 2005/0192848 A1 | 9/2005 | Kozminski et al. |
| 2006/0041427 A1 | 2/2006 | Yegnanarayanan et al. |
| 2006/0041428 A1 | 2/2006 | Fritsch et al. |
| 2006/0061595 A1 | 3/2006 | Goede |
| 2006/0069545 A1 | 3/2006 | Wu et al. |
| 2006/0074656 A1 | 4/2006 | Mathias et al. |
| 2006/0092978 A1 | 5/2006 | John et al. |
| 2006/0104454 A1 | 5/2006 | Guitarte Perez et al. |
| 2006/0104458 A1 | 5/2006 | Kenoyer et al. |
| 2006/0106645 A1 | 5/2006 | Bergelson et al. |
| 2006/0142739 A1 | 6/2006 | DiSilestro et al. |
| 2006/0173753 A1 | 8/2006 | Padmanabhan et al. |
| 2006/0241943 A1 | 10/2006 | Benja-Athon et al. |
| 2006/0277071 A1 | 12/2006 | Shufeldt |
| 2007/0033032 A1* | 2/2007 | Schubert ................ G06F 40/232 704/235 |
| 2007/0071206 A1* | 3/2007 | Gainsboro ............. G10L 25/63 379/168 |
| 2007/0136218 A1 | 6/2007 | Bauer et al. |
| 2007/0167709 A1 | 7/2007 | Slayton et al. |
| 2007/0169021 A1 | 7/2007 | Huynh et al. |
| 2007/0208567 A1 | 9/2007 | Amento et al. |
| 2007/0233488 A1 | 10/2007 | Carus et al. |
| 2007/0260977 A1 | 11/2007 | Allard et al. |
| 2008/0004505 A1 | 1/2008 | Kapit et al. |
| 2008/0004904 A1 | 1/2008 | Tran |
| 2008/0040162 A1 | 2/2008 | Brice |
| 2008/0059182 A1 | 3/2008 | Benja-Athon et al. |
| 2008/0062280 A1 | 3/2008 | Wang et al. |
| 2008/0071575 A1 | 3/2008 | Climax et al. |
| 2008/0177537 A1 | 7/2008 | Ash et al. |
| 2008/0222734 A1 | 9/2008 | Redlich et al. |
| 2008/0240463 A1 | 10/2008 | Florencio et al. |
| 2008/0247274 A1 | 10/2008 | Seltzer et al. |
| 2008/0263451 A1 | 10/2008 | Portele et al. |
| 2008/0285772 A1 | 11/2008 | Haulick et al. |
| 2009/0024416 A1 | 1/2009 | McLaughlin et al. |
| 2009/0055735 A1 | 2/2009 | Zaleski et al. |
| 2009/0070103 A1 | 3/2009 | Beggelman et al. |
| 2009/0076855 A1 | 3/2009 | McCord |
| 2009/0089082 A1 | 4/2009 | Heckerman et al. |
| 2009/0089100 A1 | 4/2009 | Nenov et al. |
| 2009/0132276 A1 | 5/2009 | Petera |
| 2009/0136094 A1 | 5/2009 | Driver |
| 2009/0150771 A1 | 6/2009 | Buck et al. |
| 2009/0157385 A1 | 6/2009 | Tian et al. |
| 2009/0172773 A1 | 7/2009 | Moore |
| 2009/0177477 A1 | 7/2009 | Nenov et al. |
| 2009/0177492 A1 | 7/2009 | Hasan et al. |
| 2009/0178144 A1 | 7/2009 | Redlich |
| 2009/0187407 A1 | 7/2009 | Soble et al. |
| 2009/0198520 A1 | 8/2009 | Piovanetti-Perez |
| 2009/0213123 A1 | 8/2009 | Crow |
| 2009/0248444 A1 | 10/2009 | Harnick |
| 2009/0259136 A1 | 10/2009 | Schieb |
| 2009/0270690 A1 | 10/2009 | Roos et al. |
| 2009/0304254 A1 | 12/2009 | Yoshida |
| 2010/0036676 A1 | 2/2010 | Safdi et al. |
| 2010/0039296 A1* | 2/2010 | Marggraff ........... G06F 3/03545 341/20 |
| 2010/0076760 A1 | 3/2010 | Kraenzel et al. |
| 2010/0076784 A1 | 3/2010 | Greenburg et al. |

(56) References Cited

U.S. PATENT DOCUMENTS

| | | |
|---|---|---|
| 2010/0077289 A1* | 3/2010 | Das .................. G06F 16/58 |
| | | 715/230 |
| 2010/0082657 A1 | 4/2010 | Paprizos et al. |
| 2010/0088095 A1 | 4/2010 | John |
| 2010/0094650 A1 | 4/2010 | Tran |
| 2010/0094656 A1 | 4/2010 | Conant |
| 2010/0094657 A1 | 4/2010 | Stern et al. |
| 2010/0100376 A1 | 4/2010 | Harrington |
| 2010/0131532 A1 | 5/2010 | Schultz |
| 2010/0145736 A1 | 6/2010 | Rohwer |
| 2010/0191519 A1 | 7/2010 | Morton et al. |
| 2010/0223216 A1 | 9/2010 | Eggert et al. |
| 2010/0238323 A1 | 9/2010 | Englund |
| 2010/0241662 A1 | 9/2010 | Keith, Jr. |
| 2011/0015943 A1 | 1/2011 | Keldie et al. |
| 2011/0063405 A1 | 3/2011 | Yam |
| 2011/0063429 A1 | 3/2011 | Contolini et al. |
| 2011/0066425 A1 | 3/2011 | Hudgins et al. |
| 2011/0071675 A1 | 3/2011 | Wells et al. |
| 2011/0096941 A1 | 4/2011 | Marzetta et al. |
| 2011/0119163 A1 | 5/2011 | Smith |
| 2011/0145013 A1 | 6/2011 | McLaughlin |
| 2011/0150420 A1* | 6/2011 | Cordonnier ............ G16H 30/20 |
| | | 386/241 |
| 2011/0153520 A1 | 6/2011 | Coifman |
| 2011/0161113 A1 | 6/2011 | Rumak et al. |
| 2011/0178798 A1 | 7/2011 | Flaks et al. |
| 2011/0178813 A1 | 7/2011 | Moore |
| 2011/0202370 A1 | 8/2011 | Green, III et al. |
| 2011/0166884 A1 | 9/2011 | Lesselroth |
| 2011/0238435 A1 | 9/2011 | Rapaport |
| 2011/0246216 A1 | 10/2011 | Agrawal |
| 2011/0251852 A1 | 10/2011 | Blas |
| 2011/0286584 A1 | 11/2011 | Angel et al. |
| 2011/0301982 A1 | 12/2011 | Green, Jr. et al. |
| 2012/0020485 A1 | 1/2012 | Visser et al. |
| 2012/0029918 A1 | 2/2012 | Bachtiger |
| 2012/0041949 A1 | 2/2012 | Hirasawa et al. |
| 2012/0053936 A1 | 3/2012 | Marvit |
| 2012/0076316 A1 | 3/2012 | Zhu et al. |
| 2012/0078626 A1 | 3/2012 | Tsai et al. |
| 2012/0081504 A1 | 4/2012 | Ng |
| 2012/0101847 A1 | 4/2012 | Johnson et al. |
| 2012/0134507 A1 | 5/2012 | Dimitriadis et al. |
| 2012/0155703 A1 | 6/2012 | Hernandez-Abrego et al. |
| 2012/0158432 A1* | 6/2012 | Jain .................. G16H 15/00 |
| | | 705/3 |
| 2012/0159391 A1 | 6/2012 | Berry et al. |
| 2012/0173269 A1 | 7/2012 | Omidi |
| 2012/0173278 A1 | 7/2012 | Herbst et al. |
| 2012/0173281 A1 | 7/2012 | DiLella et al. |
| 2012/0197660 A1* | 8/2012 | Prodanovich ......... G06T 11/206 |
| | | 705/2 |
| 2012/0208166 A1 | 8/2012 | Ernst et al. |
| 2012/0209625 A1 | 8/2012 | Armstrong et al. |
| 2012/0212337 A1 | 8/2012 | Montyne et al. |
| 2012/0215551 A1 | 8/2012 | Flanagan et al. |
| 2012/0215557 A1 | 8/2012 | Flanagan et al. |
| 2012/0215559 A1 | 8/2012 | Flanagan et al. |
| 2012/0239430 A1 | 9/2012 | Corfield |
| 2012/0253801 A1 | 10/2012 | Santos-Lang et al. |
| 2012/0253811 A1 | 10/2012 | Breslin et al. |
| 2012/0254917 A1 | 10/2012 | Burkitt et al. |
| 2012/0323574 A1 | 12/2012 | Wang et al. |
| 2012/0323575 A1* | 12/2012 | Gibbon ............... H04L 67/306 |
| | | 704/246 |
| 2012/0323589 A1 | 12/2012 | Udani |
| 2012/0330876 A1 | 12/2012 | Bryce |
| 2013/0017834 A1 | 1/2013 | Han et al. |
| 2013/0035961 A1 | 2/2013 | Yegnanarayanan |
| 2013/0041682 A1 | 2/2013 | Gottlieb et al. |
| 2013/0041685 A1 | 2/2013 | Yegnanarayanan |
| 2013/0064358 A1 | 3/2013 | Nusbaum |
| 2013/0073306 A1 | 3/2013 | Shlain et al. |
| 2013/0080879 A1 | 3/2013 | Darling |
| 2013/0103400 A1 | 4/2013 | Yegnanarayanan et al. |
| 2013/0138457 A1 | 5/2013 | Ragusa |
| 2013/0173287 A1 | 7/2013 | Cashman et al. |
| 2013/0188923 A1* | 7/2013 | Hartley ............ H04N 21/47217 |
| | | 386/241 |
| 2013/0238312 A1 | 9/2013 | Waibel |
| 2013/0238329 A1 | 9/2013 | Casella dos Santos |
| 2013/0238330 A1 | 9/2013 | Casella dos Santos |
| 2013/0246098 A1 | 9/2013 | Habboush et al. |
| 2013/0246329 A1 | 9/2013 | Pasquero et al. |
| 2013/0297347 A1 | 11/2013 | Cardoza et al. |
| 2013/0297348 A1 | 11/2013 | Cardoza et al. |
| 2013/0301837 A1 | 11/2013 | Kim et al. |
| 2013/0311190 A1 | 11/2013 | Reiner |
| 2013/0317838 A1 | 11/2013 | Schoenberg |
| 2013/0325488 A1 | 12/2013 | Carter |
| 2013/0332004 A1 | 12/2013 | Gompert et al. |
| 2013/0339030 A1 | 12/2013 | Ehsani et al. |
| 2014/0019128 A1 | 1/2014 | Riskin et al. |
| 2014/0035920 A1* | 2/2014 | Duwenhorst ......... G06T 11/001 |
| | | 345/440 |
| 2014/0047375 A1 | 2/2014 | Koll et al. |
| 2014/0050307 A1* | 2/2014 | Yuzefovich ........... H04M 15/68 |
| | | 379/68 |
| 2014/0073880 A1 | 3/2014 | Boucher |
| 2014/0074454 A1 | 3/2014 | Brown et al. |
| 2014/0093135 A1 | 4/2014 | Reid et al. |
| 2014/0096091 A1 | 4/2014 | Reid et al. |
| 2014/0122109 A1 | 5/2014 | Ghanbari et al. |
| 2014/0136973 A1 | 5/2014 | Kumar |
| 2014/0142944 A1 | 5/2014 | Ziv et al. |
| 2014/0164994 A1 | 6/2014 | Myslinski |
| 2014/0169767 A1 | 6/2014 | Goldberg |
| 2014/0188475 A1 | 7/2014 | Lev-Tov et al. |
| 2014/0188516 A1 | 7/2014 | Kamen et al. |
| 2014/0207491 A1 | 7/2014 | Zimmerman et al. |
| 2014/0222526 A1 | 8/2014 | Shakil et al. |
| 2014/0223467 A1 | 8/2014 | Hayton et al. |
| 2014/0249818 A1 | 9/2014 | Yegnanarayanan et al. |
| 2014/0249830 A1 | 9/2014 | Gallopyn et al. |
| 2014/0249831 A1 | 9/2014 | Gallopyn et al. |
| 2014/0249847 A1 | 9/2014 | Soon-Shiong et al. |
| 2014/0275928 A1 | 9/2014 | Acquista et al. |
| 2014/0278448 A1 | 9/2014 | Sadeghi et al. |
| 2014/0278522 A1 | 9/2014 | Ramsey et al. |
| 2014/0278536 A1* | 9/2014 | Zhang ................. G16H 10/60 |
| | | 705/3 |
| 2014/0279893 A1 | 9/2014 | Branton |
| 2014/0281974 A1* | 9/2014 | Shi .................... G06F 3/165 |
| | | 715/716 |
| 2014/0282008 A1 | 9/2014 | Verard |
| 2014/0288968 A1 | 9/2014 | Johnson |
| 2014/0306880 A1 | 10/2014 | Greif et al. |
| 2014/0324477 A1 | 10/2014 | Oez |
| 2014/0330586 A1 | 11/2014 | Riskin et al. |
| 2014/0337016 A1 | 11/2014 | Herbig et al. |
| 2014/0337048 A1 | 11/2014 | Brown et al. |
| 2014/0343939 A1 | 11/2014 | Mathias et al. |
| 2014/0358585 A1 | 12/2014 | Reiner |
| 2014/0362253 A1 | 12/2014 | Kim et al. |
| 2014/0365239 A1 | 12/2014 | Sadeghi |
| 2014/0365241 A1 | 12/2014 | Dillie et al. |
| 2014/0365242 A1 | 12/2014 | Neff |
| 2015/0046183 A1 | 2/2015 | Cireddu |
| 2015/0046189 A1 | 2/2015 | Dao |
| 2015/0052541 A1 | 2/2015 | Chen |
| 2015/0070507 A1 | 3/2015 | Kagan |
| 2015/0086038 A1 | 3/2015 | Stein et al. |
| 2015/0088514 A1 | 3/2015 | Typrin |
| 2015/0088546 A1 | 3/2015 | Balram et al. |
| 2015/0120305 A1 | 4/2015 | Buck et al. |
| 2015/0120321 A1 | 4/2015 | David et al. |
| 2015/0124277 A1 | 5/2015 | Ono et al. |
| 2015/0124975 A1 | 5/2015 | Pontoppidan |
| 2015/0149207 A1 | 5/2015 | O'keefe |
| 2015/0154358 A1 | 6/2015 | Anderson et al. |
| 2015/0158555 A1 | 6/2015 | Pasternak |
| 2015/0172262 A1 | 6/2015 | Ortiz, Jr. et al. |

(56) References Cited

U.S. PATENT DOCUMENTS

| | | |
|---|---|---|
| 2015/0172319 A1 | 6/2015 | Rodniansky |
| 2015/0182296 A1 | 7/2015 | Daon |
| 2015/0185312 A1 | 7/2015 | Gaubitch et al. |
| 2015/0187209 A1 | 7/2015 | Brandt |
| 2015/0220637 A1 | 8/2015 | Goetz |
| 2015/0248882 A1 | 9/2015 | Ganong, III et al. |
| 2015/0278449 A1 | 10/2015 | Laborde |
| 2015/0278534 A1 | 10/2015 | Thiyagarajan et al. |
| 2015/0290802 A1 | 10/2015 | Buehler et al. |
| 2015/0294079 A1 | 10/2015 | Bergougnan |
| 2015/0294089 A1 | 10/2015 | Nichols |
| 2015/0302156 A1 | 10/2015 | Parsadoust |
| 2015/0310174 A1 | 10/2015 | Coudert et al. |
| 2015/0310362 A1 | 10/2015 | Huffman |
| 2015/0356250 A1 | 12/2015 | Polimeni |
| 2015/0379200 A1 | 12/2015 | Gifford et al. |
| 2015/0379209 A1 | 12/2015 | Kusuma et al. |
| 2016/0012198 A1 | 1/2016 | Gainer, III et al. |
| 2016/0034643 A1 | 2/2016 | Zasowski et al. |
| 2016/0063191 A1 | 3/2016 | Vesto et al. |
| 2016/0063206 A1* | 3/2016 | Wilson ............... G16H 10/60 705/3 |
| 2016/0064000 A1 | 3/2016 | Mizumoto et al. |
| 2016/0098521 A1 | 4/2016 | Koziol |
| 2016/0110350 A1 | 4/2016 | Waibel |
| 2016/0119338 A1 | 4/2016 | Cheyer |
| 2016/0148077 A1 | 5/2016 | Cox et al. |
| 2016/0163331 A1* | 6/2016 | Yamaguchi .......... G11B 27/105 704/235 |
| 2016/0165350 A1 | 6/2016 | Benattar |
| 2016/0174903 A1 | 6/2016 | Cutaia |
| 2016/0176375 A1 | 6/2016 | Bolton et al. |
| 2016/0179770 A1 | 6/2016 | Koll et al. |
| 2016/0188809 A1 | 6/2016 | Legorburn |
| 2016/0191357 A1 | 6/2016 | Omer et al. |
| 2016/0196821 A1 | 7/2016 | Yegnanarayanan et al. |
| 2016/0203327 A1 | 7/2016 | Akkiraju et al. |
| 2016/0210429 A1 | 7/2016 | Ortiz et al. |
| 2016/0217807 A1 | 7/2016 | Gainsboro et al. |
| 2016/0234034 A1 | 8/2016 | Mahar et al. |
| 2016/0261930 A1* | 9/2016 | Kim .................... H04N 21/845 |
| 2016/0275187 A1 | 9/2016 | Chowdhury et al. |
| 2016/0300020 A1 | 10/2016 | Wetta et al. |
| 2016/0342845 A1 | 11/2016 | Tien-Spalding et al. |
| 2016/0350950 A1 | 12/2016 | Ritchie et al. |
| 2016/0357538 A1 | 12/2016 | Lewallen et al. |
| 2016/0358632 A1 | 12/2016 | Lakhani et al. |
| 2016/0360336 A1 | 12/2016 | Gross et al. |
| 2016/0364526 A1 | 12/2016 | Reicher et al. |
| 2016/0364606 A1 | 12/2016 | Conway et al. |
| 2016/0366299 A1 | 12/2016 | Sato |
| 2017/0004260 A1 | 1/2017 | Moturu et al. |
| 2017/0006135 A1 | 1/2017 | Siebel et al. |
| 2017/0011194 A1 | 1/2017 | Arshad et al. |
| 2017/0011740 A1 | 1/2017 | Gauci |
| 2017/0017834 A1 | 1/2017 | Sabitov et al. |
| 2017/0019744 A1 | 1/2017 | Matsumoto et al. |
| 2017/0046326 A1 | 2/2017 | Waibel |
| 2017/0069226 A1 | 3/2017 | Spinelli et al. |
| 2017/0076619 A1 | 3/2017 | Wallach et al. |
| 2017/0083214 A1 | 3/2017 | Furesjo et al. |
| 2017/0091246 A1 | 3/2017 | Risvik et al. |
| 2017/0093848 A1 | 3/2017 | Poisner et al. |
| 2017/0116384 A1 | 4/2017 | Ghani |
| 2017/0116392 A1 | 4/2017 | Casella dos Santos |
| 2017/0131384 A1 | 5/2017 | Davis et al. |
| 2017/0178664 A1 | 6/2017 | Wingate et al. |
| 2017/0185716 A1 | 6/2017 | Rodriguez et al. |
| 2017/0197636 A1 | 7/2017 | Beauvais |
| 2017/0228500 A1 | 8/2017 | Massengale |
| 2017/0242840 A1 | 8/2017 | Lu et al. |
| 2017/0287031 A1 | 10/2017 | Barday |
| 2017/0295075 A1 | 10/2017 | Roebuck |
| 2017/0300648 A1 | 10/2017 | Charlap |
| 2017/0316775 A1 | 11/2017 | Le et al. |
| 2017/0334069 A1 | 11/2017 | Wang et al. |
| 2018/0004915 A1 | 1/2018 | Talbot et al. |
| 2018/0025093 A1 | 1/2018 | Xia et al. |
| 2018/0032702 A1 | 2/2018 | Casella dos Santos |
| 2018/0060282 A1 | 3/2018 | Kaljurand |
| 2018/0075845 A1 | 3/2018 | Kochura |
| 2018/0081859 A1 | 3/2018 | Snider et al. |
| 2018/0107815 A1 | 4/2018 | Wu et al. |
| 2018/0122506 A1 | 5/2018 | Grantcharov et al. |
| 2018/0130554 A1 | 5/2018 | Cheng |
| 2018/0144120 A1 | 5/2018 | Fram |
| 2018/0144747 A1 | 5/2018 | Skarbovsky et al. |
| 2018/0156887 A1 | 6/2018 | Qiu et al. |
| 2018/0158461 A1 | 6/2018 | Wolff et al. |
| 2018/0158555 A1 | 6/2018 | Cashman et al. |
| 2018/0167243 A1 | 6/2018 | Gerdes |
| 2018/0181716 A1 | 6/2018 | Mander et al. |
| 2018/0197544 A1 | 7/2018 | Brooksby et al. |
| 2018/0197548 A1 | 7/2018 | Palakodety et al. |
| 2018/0218731 A1 | 8/2018 | Gustafson |
| 2018/0225277 A1 | 8/2018 | Alba |
| 2018/0232591 A1 | 8/2018 | Hicks et al. |
| 2018/0240538 A1 | 8/2018 | Koll et al. |
| 2018/0261307 A1 | 9/2018 | Couse et al. |
| 2018/0277017 A1 | 9/2018 | Cheung |
| 2018/0289291 A1 | 10/2018 | Richie |
| 2018/0310114 A1 | 10/2018 | Eronen et al. |
| 2018/0314689 A1 | 11/2018 | Wang et al. |
| 2018/0315428 A1 | 11/2018 | Johnson et al. |
| 2018/0336275 A1 | 11/2018 | Graham |
| 2019/0005959 A1 | 1/2019 | Cameron et al. |
| 2019/0012449 A1 | 1/2019 | Cheyer |
| 2019/0034604 A1 | 1/2019 | Zheng |
| 2019/0042606 A1 | 2/2019 | Griffith et al. |
| 2019/0051374 A1 | 2/2019 | Vozila et al. |
| 2019/0051375 A1 | 2/2019 | Owen et al. |
| 2019/0051376 A1 | 2/2019 | Gallopyn et al. |
| 2019/0051378 A1 | 2/2019 | Gallopyn et al. |
| 2019/0051379 A1 | 2/2019 | Owen et al. |
| 2019/0051380 A1 | 2/2019 | Owen et al. |
| 2019/0051386 A1 | 2/2019 | Yamamoto |
| 2019/0051394 A1 | 2/2019 | Owen et al. |
| 2019/0051395 A1 | 2/2019 | Owen et al. |
| 2019/0051415 A1 | 2/2019 | Owen |
| 2019/0066823 A1 | 2/2019 | Owen et al. |
| 2019/0096534 A1 | 3/2019 | Joao |
| 2019/0121532 A1 | 4/2019 | Strader et al. |
| 2019/0122766 A1 | 4/2019 | Strader et al. |
| 2019/0130073 A1 | 5/2019 | Sun et al. |
| 2019/0141031 A1 | 5/2019 | Devdas et al. |
| 2019/0172493 A1 | 6/2019 | Khan et al. |
| 2019/0182124 A1 | 6/2019 | Jeuk et al. |
| 2019/0214121 A1 | 7/2019 | O'Keeffe et al. |
| 2019/0246075 A1 | 8/2019 | Khadloya et al. |
| 2019/0251156 A1 | 8/2019 | Waibel |
| 2019/0265345 A1 | 8/2019 | Jungmaier et al. |
| 2019/0272145 A1 | 9/2019 | Sharma et al. |
| 2019/0272147 A1 | 9/2019 | Vozila et al. |
| 2019/0272827 A1 | 9/2019 | Vozila |
| 2019/0272844 A1 | 9/2019 | Sharma et al. |
| 2019/0272895 A1 | 9/2019 | Vozila et al. |
| 2019/0272896 A1 | 9/2019 | Vozila et al. |
| 2019/0272897 A1 | 9/2019 | Öz et al. |
| 2019/0272899 A1 | 9/2019 | Drexel et al. |
| 2019/0272900 A1 | 9/2019 | Jancsary et al. |
| 2019/0272901 A1 | 9/2019 | Almendro Barreda et al. |
| 2019/0272902 A1 | 9/2019 | Vozila et al. |
| 2019/0272905 A1 | 9/2019 | Almendro Barreda et al. |
| 2019/0272906 A1 | 9/2019 | Vozila et al. |
| 2019/0313903 A1 | 10/2019 | McKinnon |
| 2020/0005939 A1 | 1/2020 | Stevens et al. |
| 2020/0005949 A1 | 1/2020 | Warkentine |
| 2020/0034753 A1 | 1/2020 | Hammad |
| 2020/0160951 A1 | 5/2020 | Owen et al. |
| 2020/0265842 A1 | 8/2020 | Singh |
| 2020/0279107 A1 | 9/2020 | Staar et al. |
| 2020/0342966 A1 | 10/2020 | Stern |
| 2020/0372140 A1 | 11/2020 | Jaber et al. |
| 2021/0099433 A1 | 4/2021 | Soryal |

(56) References Cited

U.S. PATENT DOCUMENTS

| | | |
|---|---|---|
| 2021/0119802 A1 | 4/2021 | Shetty |
| 2021/0210181 A1 | 7/2021 | Owen et al. |
| 2021/0210200 A1 | 7/2021 | Gallopyn |
| 2021/0233634 A1 | 7/2021 | Owen et al. |
| 2021/0233652 A1 | 7/2021 | Owen et al. |
| 2021/0243412 A1 | 8/2021 | Owen et al. |
| 2021/0407635 A1 | 12/2021 | Owen |
| 2022/0051772 A1 | 2/2022 | Gallopyn et al. |
| 2022/0130502 A1 | 4/2022 | Vozila et al. |
| 2022/0180318 A1 | 6/2022 | Barreda et al. |
| 2022/0208322 A1 | 6/2022 | Owen et al. |
| 2022/0210161 A1 | 6/2022 | Gallopyn et al. |
| 2022/0319653 A1 | 10/2022 | Owen et al. |
| 2023/0014971 A1 | 1/2023 | Drexel et al. |
| 2023/0021529 A1 | 1/2023 | Bhattacherjee et al. |
| 2023/0092558 A1 | 3/2023 | Vozila et al. |
| 2023/0290023 A1 | 9/2023 | Tsunomori et al. |

FOREIGN PATENT DOCUMENTS

| | | |
|---|---|---|
| WO | 9844484 A1 | 10/1998 |
| WO | 2005093716 A1 | 10/2005 |
| WO | 2013082087 A1 | 6/2013 |
| WO | 2013118510 A1 | 8/2013 |
| WO | 2014134089 A1 | 9/2014 |
| WO | 2015021208 A1 | 2/2015 |
| WO | 2016125053 A1 | 8/2016 |
| WO | 20160126813 A2 | 8/2016 |
| WO | 20160149794 A1 | 9/2016 |
| WO | 2017100334 A1 | 6/2017 |
| WO | 2018132336 A1 | 7/2018 |
| WO | 2019032778 A1 | 2/2019 |

OTHER PUBLICATIONS

International Search Report and Written Opinion issued in counterpart International Application Serial No. PCT/US2018/045923 dated Oct. 2, 2018.

International Search Report and Written Opinion dated Oct. 3, 2018 in counterpart International Application Serial No. PCT/US2018/046024.

International Search Report and Written Opinion dated Oct. 3, 2018 in counterpart International Application Serial No. PCT/US2018/045982.

International Search Report and Written Opinion dated Oct. 3, 2018 in counterpart International Application Serial No. PCT/US2018/046008.

International Search Report and Written Opinion dated Oct. 2, 2018 in counterpart International Application Serial No. PCT/US2018/046034.

International Search Report and Written Opinion dated Oct. 3, 2018 in counterpart International Application Serial No. PC/US2018/045926.

International Search Report and Written Opinion dated Sep. 21, 2018 in counterpart International Application Serial No. PCT/US2018/046002.

Non-Final Office Action issued in U.S. Appl. No. 16/059,818 dated Nov. 2, 2018.

International Search Report and Written Opinion dated Oct. 24, 2018 in counterpart International Application Serial No. PCT/US2018/046041.

International Search Report and Written Opinion dated Oct. 16, 2018 in counterpart International Application Serial No. PCT/US2018/046029.

International Search Report and Written Opinion dated Oct. 11, 2018 in counterpart International Application Serial No. PCT/US2018/045994.

International Search Report and Written Opinion dated Oct. 22, 2018 in counterpart International Application Serial No. PCT/US2018/045903.

International Search Report and Written Opinion dated Oct. 22, 2018 in PCT Application Serial No. PCT/US2018/045917.

Jeffrey Klann et el., "An Intelligent Listening Framework for Capturing Encounter Notes from a Doctor-Patient Dialog", BMC Med Inform Decis Mak. 2009; 9(Suppl 1): S3, Published online Nov. 3, 2009. doi: 10.1186/1472-6947-9-S1-S3, 5 pages.

Non-Final Office Action issued in U.S. Appl. No. 16/058,871 dated Dec. 3, 2018.

International Search Report issued in PCT Application Serial No. PCT/US2018/045971 dated Oct. 30, 2018.

International Search Report issued in PCT Application Serial No. PCT/US2018/046049 dated Nov. 2, 2018.

International Search Report issued in PCT Application Serial No. PCT/US2018/045921 dated Oct. 16, 2018.

International Search Report issued in PCT Application Serial No. PCT/US2018/045896 dated Oct. 17, 2018.

Non-Final Office Action issued in U.S. Appl. No. 16/059,967 dated Jan. 2, 2019.

Non-Final Office Action issued in U.S. Appl. No. 16/058,951 dated Oct. 5, 2018.

A Study of Vision based Human Motion Recognition and Analysis to Kale et al., Dec. 2016.

International Search Report issued in PCT Application Serial No. PCT/US2018/045908 dated Oct. 19, 2018.

International Search Report issued in PCT Application Serial No. PCT/US2018/045936 dated Oct. 18, 2018.

International Search Report issued in PCT Application Serial No. PCT/US2018/045987 dated Oct. 12, 2018.

International Search Report issued in PCT Application Serial No. PCT/US2018/046006 dated Oct. 15, 2018.

Invitation to Pay Additional Fees and, Where Applicable, Protest Fee issued in PCT Application Serial No. PCT/US2012/072041 dated Jun. 6, 2013.

International Search Report issued in PCT Application Serial No. PCT/US2012/072041 dated Aug. 2, 2013.

Alapetite et al., "Introducing vocal modality into electronics anaesthesia record systems: possible effects on work practices in the operating room", EACE '05 Proceedings of the 2005 Annual Conference on European Association of Cognitive Ergonomics, Jan. 1, 2005, 197-204.

Alapetite, "Speech recognition for the anaesthesia record during crisis scenarios", 2008, International Journal of Medical Informatics, 2008, 77(1), 448-460.

Cimiano et al., "Learning concept hierarchies from text with a guided hierarchical clustering algorithm", in C. Biemann and G. Paas (eds.), Proceedings of the ICML 2005 Workshop on Learning and Extending Lexical Ontologies with Machine Learning Methods, Bonn Germany, 2005.

Fan et al., "Prismatic: Inducing Knowledge from a Large Scale Lexicalized Relation Resource", Proceedings of the NAACL HLT 2010 First International Workshop on Formalisms and Methodology for Learning by Reading, pp. 122-127, Los Angeles, California, Jun. 2010.

Florian et al., "A Statistical Model for Multilingual Entity Detection and Tracking", Proceedings of the Human Language Technologies Conference 2004.

Gomez-Perez et al., "An overview of methods and tools for ontology learning from texts", Knowledge Engineering Review 19:3, pp. 187-212, 2004.

Grasso et al., "Automated Speech Recognition in Medical Applications", MD Computing, 1995, pp. 16-23.

Harris, "Building a Large-scale Commerical NLG System for an EMR", Proceedings of the Fifth International Natural Language Generation Conference, pp. 157-160, 2008.

Jungk et al., "A Case Study in Designing Speech Interaction with a Patient Monitor", J Clinical Monitoring and Computing, 2000, 295-307.

Klann et al., "An intelligent listening framework for capturing encounter notes from a doctor-patient dialog", BMC Medical Informatics and Decision Making 2009, published Nov. 3, 2009.

Meng et al., Generating Models of Surgical Procedures using UMLS Concepts and Multiple Sequence Alignment, AMIA Annual Symposium Proceedings, 2005, pp. 520-524.

(56) References Cited

OTHER PUBLICATIONS

MIT Computer Science and Artificial Intelligence Laboratory (CSAIL) Clinical Decision Making Group, "Fair Witness: Capturing Patient-Provider Encounter through Text, Speech, and Dialogue Processing", Last updated on Apr. 9, 2010, http://groups.csail.mit.edu/medg/projects/fw/.
Welty et al., "Large Scale Relation Detection", Proceedings of the NAACL HLT 2010 First International Workshop on Formalisms and Methodology for Learning by Reading, pp. 24-33, Jun. 2010.
Zafar et., "Continuous Speech Recognition for Clinicials", J Am Med Infor Assoc, 1999, pp. 195-204.
Final Office Action issued in U.S. Appl. No. 16/059,818 dated Feb. 28, 2019.
Non-Final Office Action issued in U.S. Appl. No. 16/100,030 dated Feb. 28, 2019.
Non-Final Office Action issued in U.S. Appl. No. 16/058,912 dated Mar. 6, 2019.
Final Office Action issued in U.S. Appl. No. 16/058,951 dated Apr. 4, 2019.
Final Office Action issued in U.S. Appl. No. 16/058,871 dated Apr. 8, 2019.
Non-Final Office Action issued in U.S. Appl. No. 16/059,944 dated Apr. 15, 2019.
International Search Report issued in PCT Application Serial No. PCT/US2019/020746 dated May 14, 2019.
Notice of Allowance issued in related U.S. Appl. No. 16/100,030 dated Jan. 28, 2021.
Non-Final Office Action issued in related U.S. Appl. No. 16/441,777 dated Feb. 4, 2021.
Final Office Action issued in related U.S. Appl. No. 16/292,877 dated Feb. 8, 2021.
Non-Final Office Action issued in related U.S. Appl. No. 17/084,448 dated Feb. 10, 2021.
Non-Final Office Action issued in related U.S. Appl. No. 16/292,973 dated Feb. 12, 2021.
Final Office Action issued in related U.S. Appl. No. 16/192,427 dated Feb. 22, 2021.
International Search Report and Written Opinion issued dated Jan. 11, 2021 in PCT Application Serial No. PCT/US2020/053504.
International Search Report and Written Opinion dated Nov. 15, 2019 in PCT Application Serial No. PCT/US2019/047689.
Final Office Action issued in related U.S. Appl. No. 16/293,032 dated Mar. 1, 2021.
Non-Final Office Action issued in related U.S. Appl. No. 16/270,888 dated Mar. 2, 2021.
Notice of Allowance issued in related U.S. Appl. No. 16/058,856 dated Mar. 9, 2021.
Final Office Action issued in related U.S. Appl. No. 16/058,871, dated Mar. 18, 2021.
Non-Final Office Action issued in related U.S. Appl. No. 16/059,818 dated Mar. 18, 2021.
Zhou et al., "Applying the Narve Bayes Classifier to Assist Users in Detecting Speech Recognition Errors," Proceedings of the 38th Annual Hawaii International Conference on System Sciences, Big Island, HI, USA, 2005, pp. 183b-183b, doi: 10.1109/HICSS .2005. 99.
Abdulkader et al., "Low Cost Correction of OCR Errors Using Learning in a Multi-Engine Environment," 2009 10th International Conference on Document Analysis and Recognition, Barcelona, 2009, pp. 576-580, doi: 10.1109/ICDAR.2009.242.
Final Office Action issued in related U.S. Appl. No. 16/059,895 dated Mar. 24, 2021.
Final Office Action issued in related U.S. Appl. No. 16/059,974 dated Mar. 24, 2021.
Final Office Action issued in related U.S. Appl. No. 16/059,986 dated Mar. 24, 2021.
Non-Final Office Action issued in related U.S. Appl. No. 16/292,895 dated Mar. 25, 2021.
Non-Final Office Action issued in related U.S. Appl. No. 16/292,920 dated Mar. 26, 2021.
Non-Final Office Action issued in related U.S. Appl. No. 16/270,888 dated Mar. 26, 2021.
Non-Final Office Action issued in related U.S. Appl. No. 16/271,329 dated Mar. 26, 2021.
HU et al., "Deep Multimodel Speaker Naming", Computing Research Repository, vol. abs/1507.04831, 2015 (Year: 2015).
Final Office Action issued in related U.S. Appl. No. 16/271,029 dated Apr. 1, 2021.
Non-Final Office Action issued in related U.S. Appl. No. 16/058,826 dated Apr. 6, 2021.
Notice of Allowance issued in related U.S. Appl. No. 16/058,871 dated Apr. 9, 2021.
Final Office Action issued in related U.S. Appl. No. 17/084,310 dated Apr. 12, 2021.
Non-Final Office Action issued in related U.S. Appl. No. 16/441,740 dated Apr. 14, 2021.
Non-Final Office Action issued in related U.S. Appl. No. 16/442,247 dated Apr. 15, 2021.
Non-Final Office Action issued in related U.S. Appl. No. 16/058,925 dated Apr. 16, 2021.
Non-Final Office Action issued in related U.S. Appl. No. 16/058,914 dated Apr. 16, 2021.
Non-Final Office Action issued in related U.S. Appl. No. 16/058,894 dated Apr. 16, 2021.
Supplementary European Search Report issued in counterpart Application Serial No. 188344752.8 dated Mar. 3, 2021.
Non-Final Office Action issued in related U.S. Appl. No. 16/058,883 dated Apr. 28, 2021.
Notice of Allowance issued in related U.S. Appl. No. 16/059,944 dated Apr. 30, 2021.
Final Office Action issued in related U.S. Appl. No. 16/270,782 dated May 7, 2021.
Notice of Allowance issued in related U.S. Appl. No. 16/441,777 dated May 14, 2021.
Final Office Action issued in related U.S. Appl. No. 17/084,448 dated Jun. 1, 2021.
Non-Final Office Action issued in related U.S. Appl. No. 16/292,893 dated Jun. 9, 2021.
Notice of Allowance issued in related U.S. Appl. No. 16/058,871 dated Jun. 14, 2021.
Non-Final Office Action issued in related U.S. Appl. No. 16/293,032 dated Jun. 24, 2021.
Non-Final Office Action issued in related U.S. Appl. No. 16/058,803 dated Jun. 24, 2021.
Non-Final Office Action issued in related U.S. Appl. No. 16/058,829 dated Jun. 25, 2021.
Final Office Action issued in related U.S. Appl. No. 16/192,358 dated Jun. 25, 2021.
Notice of Allowance issued in related U.S. Appl. No. 16/059,818 dated Jul. 2, 2021.
Notice of Allowance issued in related U.S. Appl. No. 16/058,936 dated Jul. 7, 2021.
Notice of Allowance issued in related U.S. Appl. No. 17/084,310 dated Jul. 9, 2021.
Notice of Allowance issued in related U.S. Appl. No. 16/058,941 dated Jul. 14, 2021.
Notice of Allowance issued in related U.S. Appl. No. 16/292,920 dated Jul. 15, 2021.
Non-Final Office Action issued in related U.S. Appl. No. 16/773,447 dated Jul. 20, 2021.
Non-Final Office Action issued in related U.S. Appl. No. 17/210,052 dated Nov. 19, 2021.
Notice of Allowance issued in related U.S. Appl. No. 16/192,427 dated Dec. 3, 2021.
International Search Report and Written Opinion dated Dec. 1, 2021 in PCT Application Serial No. PCT/US2021/056265.
Notice of Allowance issued in U.S. Appl. No. 16/192,427 dated Dec. 8, 2021.
Notice of Allowance issued in U.S. Appl. No. 16/271,329 dated Dec. 13, 2021.
Notice of Allowance issued in U.S. Appl. No. 16/773,447 dated Dec. 15, 2021.

(56) References Cited

OTHER PUBLICATIONS

Notice of Allowance issued in U.S. Appl. No. 16/059,986 dated Dec. 15, 2021.
Notice of Allowance issued in U.S. Appl. No. 16/270,782 dated Dec. 16, 2021.
Non-Final Office Action issued in U.S. Appl. No. 16/588,475 dated Jan. 10, 2022.
Notice of Allowance issued in U.S. Appl. No. 16/059,895 dated Jan. 18, 2022.
Non-Final Office Action issued in U.S. Appl. No. 16/270,888 dated Jan. 20, 2022.
Final Office Action issued in U.S. Appl. No. 16/271,029 dated Jan. 31, 2022.
Notice of Allowance issued in U.S. Appl. No. 17/084,448 dated Jan. 26, 2022.
Notice of Allowance issued in U.S. Appl. No. 17/210,120 dated Mar. 1, 2022.
Notice of Allowance issued in U.S. Appl. No. 16/059,974 dated Feb. 4, 2022.
International Search Report issued in International Application No. PCT/US2021/056274 dated Dec. 7, 2021.
Notice of Allowance issued in U.S. Appl. No. 16/058,883 dated Mar. 25, 2022.
Non-Final Office Action issued in U.S. Appl. No. 16/058,826 dated Mar. 29, 2022.
Notice of Allowance issued in U.S. Appl. No. 16/058,914 dated Mar. 30, 2022.
Non-Final Office Action issued in U.S. Appl. No. 16/058,925 dated Mar. 30, 2022.
Van Hoff et al., Ageing-in-Place with the use of Ambient Intelligence Technology: Perspectives of Older Users, International Journal of Medical Informatics, vol. 80, Issue 5, May 2011, pp. 310-331.
Non-Final Office Action issued in U.S. Appl. No. 16/058,9894 dated Mar. 31, 2022.
Non-Final Office Action issued in U.S. Appl. No. 16/588,897 dated Mar. 31, 2022.
Non-Final Office Action issued in U.S. Appl. No. 16/292,893 dated Mar. 29, 2022.
Final Office Action issued in U.S. Appl. No. 16/059,967 dated Apr. 1, 2022.
Non-Final Office Action issued in U.S. Appl. No. 16/292,973 dated Apr. 1, 2022.
Non-Final Office Action issued in U.S. Appl. No. 16/293,032 dated Apr. 5, 2022.
Non-Final Office Action issued in U.S. Appl. No. 16/292,877 dated May 2, 2022.
Final Office Action issued in U.S. Appl. No. 16/059,974, dated Jul. 6, 2020.
Final Office Action issued in U.S. Appl. No. 16/059,895, dated Jul. 6, 2020.
Non-Final Office Action issued in related U.S. Appl. No. 16/059,944, dated Jul. 13, 2020.
Notice of Allowance issued in related U.S. Appl. No. 16/271,616 dated Jul. 13, 2020.
Non-Final Office Action issued in related U.S. Appl. No. 16/058,826, dated Jul. 17, 2020.
Non-Final Office Action issued in related U.S. Appl. No. 16/058,914, dated Jul. 17, 2020.
Non-Final Office Action issued in related U.S. Appl. No. 16/058,925 dated Jul. 20, 2020.
Non-Final Office Action issued in related U.S. Appl. No. 16/058,894 dated Jul. 30, 2020.
Non-Final Office Action issued in related U.S. Appl. No. 16/292,877 dated Jul. 23, 2020.
Non-Final Office Action issued in related U.S. Appl. No. 16/058,883 dated Jul. 31, 2020.
Non-Final Office Action issued in related U.S. Appl. No. 16/058,829 dated Aug. 5, 2020.
Inal Office Action issued in related U.S. Appl. No. 16/058,856 dated Aug. 12, 2020.
Final Office Action issued in related U.S. Appl. No. 16/292,920 dated Aug. 11, 2020.
Non-Final Office Action issued in related U.S. Appl. No. 16/058,912 dated Aug. 20, 2020.
Non-Final Office Action issued in related U.S. Appl. No. 16/100,030 dated Aug. 25, 2020.
Non-Final Office Action issued in related U.S. Appl. No. 16/059,818 dated Aug. 25, 2020.
Non-Final Office Action issued in related U.S. Appl. No. 16/058,803 dated Sep. 3, 2020.
YouTube video clip entitled "Nuance PowerMic Mobile gives clinicians greater mobility", retrieved from Internet: https://www.youtube.com/watch?v=OjqiePRFtl@feature=emb-logo (Year: 2015), 3 pages.
Non-Final Office Action issued in related U.S. Appl. No. 16/271,029 dated Sep. 8, 2020.
Non-Final Office Action issued in related U.S. Appl. No. 16/293,032 dated Sep. 16, 2020.
Non-Final Office Action issued in related U.S. Appl. No. 16/192,427 dated Sep. 21, 2020.
Non-Final Office Action issued in related U.S. Appl. No. 16/292,893 dated Oct. 2, 2020.
David, G. C. et al., "Listening to what is said-transcribing what is heard: the impact of speech recognition technology (SRT) on the practice of medical transcription (MT)", Sociology of Heath and Illness, vol. 31, No. 6, pp. 924-938, (2009).
Non-Final Office Action issued in related U.S. Appl. No. 16/058,871 dated Oct. 5, 2020.
Non-Final Office Action issued in related U.S. Appl. No. 16/058,941 dated Oct. 26, 2020.
International Search Report and Written Opinion dated Aug. 19, 2020 in PCT Application Serial No. PCT/US2020/037284.
Final Office Action issued in related U.S. Appl. No. 16/058,826, dated Nov. 30, 2020.
Final Office Action issued in related U.S. Appl. No. 16/058,803 dated Nov. 30, 2020.
Final Office Action issued in related U.S. Appl. No. 16/058,883 dated Nov. 30, 2020.
Final Office Action issued in related U.S. Appl. No. 16/058,925 dated Nov. 30, 2020.
Final Office Action issued in related U.S. Appl. No. 16/058,914, dated Nov. 30, 2020.
Final Office Action issued in related U.S. Appl. No. 16/292,895, dated Nov. 30, 2020.
Non-Final Office Action issued in related U.S. Appl. No. 16/192,358, dated Nov. 27, 2020.
Final Office Action issued in related U.S. Appl. No. 16/059,818 dated Dec. 4, 2020.
Non-Final Office Action issued in related U.S. Appl. No. 16/059,895, dated Dec. 9, 2020.
Final Office Action issued in related U.S. Appl. No. 17/084,310 dated Dec. 22, 2020.
Non-Final Office Action issued in related U.S. Appl. No. 16/059,974, dated Dec. 18, 2020.
Non-Final Office Action issued in related U.S. Appl. No. 16/059,986, dated Dec. 18, 2020.
International Search Report and Written Opinion dated Aug. 31, 2020 in PCT Application Serial No. PCT/US2020/037226.
Final Office Action issued in related U.S. Appl. No. 16/058,829 dated Jan. 11, 2021.
Non-Final Office Action issued in related U.S. Appl. No. 17/084,310, dated Dec. 21, 2020.
Notice of Allowance issued in related U.S. Appl. No. 16/100,030 dated Jan. 11, 2021.
Angles, R., "A Comparison of Current Graph Database Models", In: 2012 IEEE 28th International Conference on Data Engineering Workshops, Apr. 5, 2012 (Apr. 5, 2012) Retrieved on Aug. 5, 2020 (Aug. 5, 2020) from URL:https://ieeexplore.ieee.org/document/6313676 entire document, 7 pages.
Final Office Action issued in related U.S. Appl. No. 16/059,944 dated Dec. 28, 2020.
Final Office Action issued in related U.S. Appl. No. 16/058,894 dated Dec. 1, 2020.

(56) References Cited

OTHER PUBLICATIONS

Final Office Action issued in related U.S. Appl. No. 16/058,941 dated Dec. 22, 2020.
Notice of Allowance issued in related U.S. Appl. No. 16/058,856 dated Jan. 19, 2021.
Non-Final Office Action issued in related U.S. Appl. No. 16/270,782 dated Jan. 19, 2021.
Notice of Allowance issued in related U.S. Appl. No. 16/058,912 dated Jan. 22, 2021.
Final Office Action issued in related U.S. Appl. No. 16/292,893 dated Jan. 28, 2021.
Lenert et al., "Design and Evaluation of a Wireless Electronic Health Records System for Field Care in Mass Casualty Settings", Journal of the American Medical Informatics Association, Nov.-Dec. 2011; 18(6); pp. 842-852. https://www.ncbi.nlm.nih.gov/pmc/articles/PMC3198000/.
International Search Report issued in PCT Application Serial No. PCT/US2019/020742 dated May 14, 2019.
International Search Report issued in PCT Application Serial No. PCT/US2019/020739 dated May 17, 2019.
International Search Report issued in PCT Application Serial No. PCT/US2019/020763 dated May 23, 2019.
International Search Report issued in PCT Application Serial No. PCT/US2019/020765 dated May 23, 2019.
International Search Report issued in PCT Application Serial No. PCT/US2019/020778 dated May 23, 2019.
International Search Report issued in PCT Application Serial No. PCT/US2019/020771 dated May 30, 2019.
Non-Final Office Action issued in U.S. Appl. No. 16/059,818 dated Jun. 10, 2019.
International Search Report issued in PCT Application Serial No. PCT/US2019/020721 dated Jun. 6, 2019.
International Search Report issued in PCT Application Serial No. PCT/US2019/020755 dated Jun. 6, 2019.
Final Office Action issued in U.S. Appl. No. 16/059,967 dated Jul. 11, 2019.
Final Office Action issued in U.S. Appl. No. 16/100,030 dated Jul. 18, 2019.
Non-Final Office Action issued in U.S. Appl. No. 16/058,951 dated Jul. 25, 2019.
International Search Report issued in International App. No. PCT/US2019/020788 dated Jul. 17, 2019.
Final Office Action issued in U.S. Appl. No. 16/058,912 dated Jul. 31, 2019.
Final Office Action issued in U.S. Appl. No. 16/059,944 dated Aug. 22, 2019.
Non-Final Office Action issued in U.S. Appl. No. 16/058,871 dated Sep. 23, 2019.
Final Office Action issued in U.S. Appl. No. 16/059,818 dated Sep. 25, 2019.
Notice of Allowance issued in U.S. Appl. No. 16/100,030 dated Oct. 9, 2019.
Non-Final Office Action issued in U.S. Appl. No. 16/192,427 dated Oct. 3, 2019.
Non-Final Office Action issued in U.S. Appl. No. 16/271,616 dated Nov. 15, 2019.
Non-Final Office Action issued in U.S. Appl. No. 16/192,358 dated Nov. 19, 2019.
Non-Final Office Action issued in U.S. Appl. No. 16/059,944 dated Dec. 23, 2019.
Non-Final Office Action issued in U.S. Appl. No. 16/059,818 dated Jan. 9, 2020.
Non-Final Office Action issued in related U.S. Appl. No. 16/058,912 dated Jan. 27, 2020.
Non-Final Office Action issued in U.S. Appl. No. 16/292,920 dated Feb. 28, 2020.
Non-Final Office Action issued in related U.S. Appl. No. 16/100,030 dated Mar. 4, 2020.
Notice of Allowance issued in related U.S. Appl. No. 16/271,616 dated Mar. 17, 2020.

Dibiase, J. H. et al., "Robust Localization in Reverberant Rooms," in Microphone Arrays—Signal Processing Techniques and Applications, Ch. 8, pp. 157-180.
Valin, Jean-Marc et al., "Robust Sound Source Localization Using a Microphone Array on a Mobile Robot," Proceedings of the 2003 IEEE/RSJ International Conference on Intelligent Robots and Systems, vol. 2, 2003, pp. 1228-1233.
Wang, L. et al., "Over-determined Source Separation and Localization Using Distributed Microphone," IEEE/ACM Transactions on Audio, Speech, and Language Processing, vol. 24, No. 9, Sep. 2016, pp. 1573-1588.
Notice of Allowance issued in U.S. Appl. No. 16/108,959 dated Nov. 6, 2019.
Bahdanau, D. et al., "Neural Machine Translation by Jointly Learning to Align and Translate", Published as a Conference Paper at ICLR 2015, May 19, 2016, 15 pages.
Final Office Action issued in related U.S. Appl. No. 16/192,427 dated Mar. 6, 2020.
Final Office Action issued in related U.S. Appl. No. 16/058,871 dated Mar. 19, 2020.
Final Office Action issued in U.S. Appl. No. 16/059,944 dated Mar. 26, 2020.
Non-Final Office Action issued in U.S. Appl. No. 16/058,936 dated Apr. 15, 2020.
Non-Final Office Action issued in U.S. Appl. No. 16/058,941 dated Apr. 15, 2020.
Non-Final Office Action issued in U.S. Appl. No. 16/059,895 dated Apr. 24, 2020.
Non-Final Office Action issued in U.S. Appl. No. 16/059,974 dated Apr. 24, 2020.
Non-Final Office Action issued in U.S. Appl. No. 16/059,986 dated Apr. 24, 2020.
Final Office Action issued in U.S. Appl. No. 16/100,310 dated May 8, 2020.
Final Office Action issued in related U.S. Appl. No. 16/058,912 dated May 26, 2020.
Non-Final Office Action issued in related U.S. Appl. No. 16/271,616 dated May 29, 2020.
Final Office Action issued in related U.S. Appl. No. 16/192,358 dated Jun. 2, 2020.
Non-Final Office Action issued in related U.S. Appl. No. 16/292,895 dated Jun. 5, 2020.
Final Office Action issued in related U.S. Appl. No. 16/058,941 dated Jun. 23, 2020.
Final Office Action issued in U.S. Appl. No. 16/058,936 dated Jun. 23, 2020.
Non-Final Office Action issued in related U.S. Appl. No. 16/058,856 dated Jul. 2, 2020.
Final Office Action issued in U.S. Appl. No. 16/059,986 dated Jul. 6, 2020.
Notice of Allowance issued in related U.S. Appl. No. 16/442,247 dated Jul. 22, 2021.
Communication issuing supplementary European Search Report of May 14, 2021 and Extended European Search Report dated Apr. 16, 2021 in counterpart Application Serial No. EP 18844226.3.
Communication issuing supplementary European Search Report of Apr. 8, 2021 and Extended European Search Report dated Mar. 10, 2021 in counterpart Application Serial No. EP 18845046.4.
Gross R, et al: "Towards a multimodal meeting record", Multimedia and Expo, 2000. ICME 2000. 2000 IEEE International Conference in New York, NY, USA Jul. 30-Aug. 2, 2000, Piscataway, NJ, USA, IEEE, US, vol. 3, Jul. 30, 2000 (Jul. 30, 2000, pp. 1593-1596, XP010512812, DOI: 10.1109/ICME.2000.871074 ISBN 978-0-7803-6536-0 *the whole document*.
Communication issuing supplementary European Search Report of Apr. 8, 2021 and Extended European Search Report dated in Mar. 10, 2021 counterpart Application Serial No. EP 18842996.3.
Communication issuing supplementary European Search Report of May 19, 2021 and Extended European Search Report dated Apr. 19, 2021 in counterpart Application Serial No. EP 18844530.8.
Communication issuing supplementary European Search Report of May 19, 2021 and Extended Europe Search Report dated Apr. 19, 2021 in counterpart Application Serial No. EP 18843844.1.

(56) References Cited

OTHER PUBLICATIONS

Nadir, Weibel, et al.: "LAB-IN-A-BOX: semi-automatic tracking of activity in the medical office", Personal and Ubiqitous Computing, Springer Verlag, Lond, GB, vol. 19, No. 2, Sep. 28, 2014 (Sep. 28, 2014) pp. 317-334, XP058066121, ISSN: 1617-4909, DOI: 10.1007/S00779-014-0821-0 *abstract* *Section 4, The LAB-IN-A-BOX; pp. 321-327* *Section 5.2, "Data collection and analysis"; pp. 330-331* *table 1* *figures 7,8*.
Communication issuing supplementary European Search Report of May 28, 2021 and Extended European Search Report dated May 3, 2021 in counterpart Application Serial No. EP 18843648.9.
Communication issuing supplementary European Search Report of May 28, 2021 and Extended European Search Report dated Apr. 16, 2021 in counterpart Application Serial No. EP 18843945.9.
Communication issuing supplementary European Search Report of May 19, 2021 and Extended European Search Report dated Apr. 19, 2021 in counterpart Application Serial No. EP 18844669.4.
Yang, et al., "The Design and Implementation of a Smart e-Receptionist", IEE Potentials, IEEE, New York, NY, US, vo. 32, No. 4, Jul. 22, 2013 (Jul. 22, 2013), pp. 22-27, XP011522905, ISSN: 0278-6648, DOI: 10.1109/MPOT.2012.2213851 *the whole document*.
Communication issuing supplementary European Search Report of May 14, 2021 and Extended European Search Report dated Apr. 16, 2021 in counterpart Application Serial No. EP 18843175.3.
Communication issuing supplementary European Search Report of May 28, 2021 and Extended European Search Report dated Apr. 29, 2021 in counterpart Application Serial No. EP 18845144.7.
Non-Final Office Action dated Aug. 6, 2021 in counterpart U.S. Appl. No. 16/270,782.
Final Office Action dated Aug. 19, 2021 in counterpart U.S. Appl. No. 16/292,973.
Communication issuing supplementary European Search Report dated Apr. 12, 2021 and Extended European Search Report dated Mar. 12, 2021 in counterpart Application Serial No. EP 18843255.3.
Communication issuing supplementary European Search Report dated May 26, 2021 and Extended European Search Report dated Apr. 30, 2021 in counterpart Application Serial No. EP 18844675.1.
Communication issuing supplementary European Search Report dated Mar. 30, 2021 and Extended European Search Report dated Mar. 3, 2021 in counterpart Application Serial No. EP 18844752.8.
Shivappa, S. et al., "Role of Head PSE Estimation in Speech Acquisition from Distant Microphones," Acoustics, Speech and Signal Processing, ICASSP 2009, IEEE International Conference on IEEE, pp. 3557-3560, Apr. 19, 2009.
Communication issuing supplementary European Search Report dated Apr. 6, 2021 and Extended European Search Report dated Mar. 8, 2021 in counterpart Application Serial No. EP 18844407.9.
Communication issuing supplementary European Search Report dated Apr. 12, 2021 and Extended European Search Report dated Apr. 19, 2021 in counterpart Application Serial No. EP 18843873.3.
Communication issuing supplementary European Search Report dated Apr. 12, 2021 and Extended European Search Report dated Mar. 11, 2021 in counterpart Application Serial No. EP 18843329.6.
Communication issuing supplementary European Search Report dated Apr. 13, 2021 and Extended European Search Report dated Apr. 19, 2021 in counterpart Application Serial No. EP 18843586.1.
Communication issuing supplementary European Search Report dated Apr. 16, 2021 and Extended European Search Report dated Mar. 22, 2021 in counterpart Application Serial No. EP 18843254.6.
Communication issuing supplementary European Search Report dated May 26, 2021 and Extended European Search Report dated Apr. 30, 2021 in counterpart Application Serial No. EP 18844406.1.
Non-Final Office Action issued in counterpart U.S. Appl. No. 16/271,029 dated Sep. 15, 2021.
Notice of Allowance issued in counterpart U.S. Appl. No. 16/059,895 dated Sep. 13, 2021.
Final Office Action issued in counterpart U.S. Appl. No. 16/270,888 dated Sep. 9, 2021.
Notice of Allowance issued in counterpart U.S. Appl. No. 17/084,448 dated Sep. 22, 2021.
Non-Final Office Action issued in counterpart U.S. Appl. No. 16/059,967 dated Sep. 20, 2021.
Klaan et al. , "An Intelligent listening framework for capturing encounter notes from a doctor-patient dialog," BMC Medical Informatics and Decision Making, vol. 9, Suppl, Suppl 1, S3. Nov. 2009.
Final Office Action issued in counterpart U.S. Appl. No. 16/292,895 dated Sep. 30, 2021.
Notice of Allowance issued in counterpart U.S. Appl. No. 16/059,974 dated Oct. 5, 2021.
Notice of Allowance issued in counterpart U.S. Appl. No. 16/059,986 dated Oct. 12, 2021.
Final Office Action issued in counterpart U.S. Appl. No. 16/058,826 dated Oct. 21, 2021.
Final Office Action issued in counterpart U.S. Appl. No. 16/058,894 dated Oct. 29, 2021.
Final Office Action issued in counterpart U.S. Appl. No. 16/058,883 dated Oct. 29, 2021.
Final Office Action issued in counterpart U.S. Appl. No. 16/058,925 dated Oct. 29, 2021.
Final Office Action issued in counterpart U.S. Appl. No. 16/058,914 dated Oct. 29, 2021.
Unknown, You Tube video clip entitled "Nuance Healthcare Florence Workflow Concept with Samsung Smartwatch Demo English," retrieved from Internet: https://www.youtube.com/watch?v=l-NVD60oyn) (Year: 2015).
Final Office Action issued in counterpart U.S. Appl. No. 16/292,893 dated Nov. 15, 2021.
Notice of Allowance issued counterpart U.S. Appl. No. 16/292,920 dated Nov. 10, 2021.
Notice of Allowance issued in counterpart U.S. Appl. No. 17/084,310 dated Nov. 12, 2021.
Notice of Allowance issued in counterpart U.S. Appl. No. 16/442,247 dated Nov. 15, 2021.
Notice of Allowance issued in counterpart U.S. Appl. No. 16/441,740 dated Nov. 15, 2021.
Luck, J. et al., Using standardized patients to measure physicians' practice: validation study using audio recordings. Bmj, 325(7366), 679 (2002).
Final Office Action issued in related U.S. Appl. No. 16/293,032 dated Nov. 19, 2021.
Final Office Action issued in related U.S. Appl. No. 16/292,973 dated Oct. 28, 2022.
Final Office Action issued in related U.S. Appl. No. 16/058,925 dated Oct. 20, 2022.
Final Office Action issued in related U.S. Appl. No. 16/058,803 dated May 18, 2022.
Final Office Action issued in related U.S. Appl. No. 16/058,894 dated Aug. 17, 2022.
Non-Final Office Action issued in related U.S. Appl. No. 17/571,819 dated Nov. 7, 2022.
Non-Final Office Action issued in related U.S. Appl. No. 16/271,029 dated Jun. 21, 2022.
Non-Final Office Action issued in related U.S. Appl. No. 16/058,803 dated Sep. 21, 2022.
Non-Final Office Action issued in related U.S. Appl. No. 16/588,475 dated Sep. 16, 2022.
Notice of Allowance issued in U.S. Appl. No. 17/467,688 dated Oct. 6, 2022.
Notice of Allowance issued in U.S. Appl. No. 17/210,120 dated Jun. 10, 2022.
Notice of Allowance issued in U.S. Appl. No. 16/293,032 dated Jul. 25, 2022.
Notice of Allowance issued in U.S. Appl. No. 16/058,914 dated Sep. 14, 2022.
Notice of Allowance issued in U.S. Appl. No. 16/270,888 dated Jul. 13, 2022.
Final Office Action issued in related U.S. Appl. No. 16/058,826 dated Aug. 19, 2022.
Final Office Action issued in related U.S. Appl. No. 16/292,893 dated Jul. 28, 2022.

(56) References Cited

OTHER PUBLICATIONS

International Search Report and Written Opinion dated Sep. 2, 2022 in PCT Application Serial No. PCT/US2022/21393.
International Search Report and Written Opinion dated Sep. 2, 2022 in PCT Application Serial No. PCT/US2022/21412.
International Search Report and Written Opinion dated Sep. 2, 2022 in PCT Application Serial No. PCT/US2022/21422.
International Search Report and Written Opinion dated Jul. 26, 2022 in PCT Application Serial No. PCT/US2022/021375.
International Search Report and Written Opinion dated Sep. 23, 2022 in PCT Application Serial No. PCT/US2022/21419.
U.S. Appl. No. 16/058,803, filed May 18, 2022.
U.S. Appl. No. 16/058,894, filed Aug. 17, 2022.
U.S. Appl. No. 17.571,819, filed Nov. 7, 2022.
U.S. Appl. No. 16/271,029, filed Jun. 21, 2022.
U.S. Appl. No. 16/058,803, filed Sep. 21, 2022.
U.S. Appl. No. 16/588,475, filed Sep. 16, 2022.
U.S. Appl. No. 17/467,688, filed Oct. 6, 2022.
U.S. Appl. No. 17/210,120, filed Jun. 10, 2022.
U.S. Appl. No. 16/293,032, filed Jul. 25, 2022.
U.S. Appl. No. 16/058,914, filed Sep. 14, 2022.
U.S. Appl. No. 16/270,888, filed Jul. 13, 2022.
U.S. Appl. No. 16/058,826, filed Aug. 19, 2022.
U.S. Appl. No. 16/292,893, filed Jul. 28, 2022.
"Notice of Allowance Issued in U.S. Appl. No. 16/058,829", dated Jun. 3, 2022, 9 Pages.
"Notice of Allowance Issued in U.S. Appl. No. 16/058,883", dated Jun. 2, 2022, 2 Pages.
"Non Final Office Action Issued in U.S. Appl. No. 16/058,914", dated May 24, 2022, 9 Pages.
"Advisory Action Issued in U.S. Appl. No. 16/058,936", dated Aug. 19, 2020, 5 Pages.
"Advisory Action Issued in U.S. Appl. No. 16/058,936", dated Mar. 22, 2021, 5 Pages.
"Notice of Allowance Issued in U.S. Appl. No. 16/058,951", dated Nov. 15, 2019, 11 Pages.
"Final Office Action Issued in U.S. Appl. No. 16/059,818", dated Apr. 7, 2020, 7 Pages.
"Advisory Action Issued in U.S. Appl. No. 16/059,895", dated Sep. 10, 2020, 5 Pages.
"Advisory Action Issued in U.S. Appl. No. 16/059,974", dated Jun. 11, 2021, 5 Pages.
"Advisory Action Issued in U.S. Appl. No. 16/059,974", dated Sep. 15, 2020, 5 Pages.
"Advisory Action Issued in U.S. Appl. No. 16/059,986", dated Sep. 15, 2020, 5 Pages.
"Final Office Action Issued in related U.S. Appl. No. 16/058,829", dated May 8, 2020, 10 Pages.
"Notice of Allowance Issued in U.S. Appl. No. 16/192,358", dated Dec. 8, 2021, 8 Pages.
"Final Office Action Issued in U.S. Appl. No. 16/292,877", dated Nov. 14, 2022, 10 Pages.
"Non Final Office Action Issued in U.S. Appl. No. 16/292,895", dated May 17, 2022, 17 Pages.
"Notice of Allowance Issued in U.S. Appl. No. 16/588,897", dated Sep. 2, 2022, 8 Pages.
"Non Final Office Action Issued in U.S. Appl. No. 16/210,120", dated Nov. 1, 2021, 14 Pages.
"Non Final Office Action Issued in U.S. Appl. No. 17/571,799", dated Dec. 6, 2022, 26 Pages.
"Non Final Office Action Issued in U.S. Appl. No. 17/696,165", dated Nov. 25, 2022, 7 Pages.
"Office Action Issued in European Patent Application No. 18844675.1", dated Mar. 4, 2022, 6 Pages.
"Extended European Search Report Issued in European Patent Application No. 18844829.4", dated Apr. 30, 2021, 9 Pages.
"Extended European Search Report Issued in Application No. 19763338.1", dated Apr. 4, 2022, 8 Pages.
"Extended European Search Report for Application No. 1976347.4", dated Apr. 8, 2021, 8 Pages.
"Extended European Search Report Issued in Application No. 19763475.1", dated Apr. 12, 2022, 10 Pages.
"Search Report Issued in European Patent Application No. 19763477.7", dated Mar. 28, 2022, 10 Pages.
"Search Report Issued in European Patent Application No. 19763600.4", dated Mar. 31, 2022, 9 Pages.
"Search Report Issued in European Patent Application No. 19763678.0", dated Mar. 25, 2022, 8 Pages.
"Search Report Issued in European Patent Application No. 19763834.9", dated Dec. 10 2021, 9 Pages.
"Search Report Issued in European Patent Application No. 19764329.9", dated Dec. 14, 2021, 13 Pages.
"Invitaton To Pay Additional Fees Issued in PCT Application No. PCT/US22/021393", dated Jun. 24, 2022, 2 Pages.
"Invitaton To Pay Additional Fees Issued in PCT Application No. PCT/US22/021412", dated Jun. 24, 2022, 2 Pages.
"Invitaton To Pay Additional Fees Issued in PCT Application No. PCT/US22/021419", dated Jul. 5, 2022, 2 Pages.
"Invitaton To Pay Additional Fees Issued in PCT Application No. PCT/US22/021422", dated Jun. 24, 2022, 2 Pages.
Pusateri at al., "A Mostly Data-Driven Approach to Inverse Text Normalization", In Proceedings of Interspeech, Aug. 26, 2017, pp. 2784-2788.
Shen, et al., "Auto-encoding twin-bottleneck Hashing", Ins Proceeding of the IEEE/CVF Conference on Computer Vision and Pattern Recognition, Jun. 13, 2020, pp. 2818-2827.
"Notice of Allowance Issued in U.S. Appl. No. 16/058,914", dated Jan. 5, 2023, 11 Pages.
"Final Office Action Issued in U.S. Appl. No. 16/058,803", dated Mar. 20, 2023, 12 Pages.
"Final Office Action Issued in U.S. Appl. No. 16/292,895", dated Jan. 5, 2023, 17 Pages.
"Office Action Issued in European Patent Application No. 18843329.6", dated Feb. 24, 2023, 5 Pages.
Shivappa, et al., "Person Tracking With Audio-visual Cues Using The Iterative Decoding Framework", In Proceedings of the IEEE Fifth International Conference on Advanced Video and Signal Based Surveillance, Sep. 1, 2008, pp. 260-267.
"Non Final Office Action Issued in U.S. Appl. No. 17/991,234", dated Mar. 14, 2023, 42 Pages.
Watanabe, et al., "Hybrid CTC/Attention Architecture for End-to-End Speech Recognition", In Journal of IEEE Selected Topics in Signal Processing, Vol. 11, Issue 8, Dec. 2017, pp. 1240-1253.
"Final Office Action Issued in U.S. Appl. No. 17/991,234", dated Jul. 11, 2023, 35 Pages.
"Notice of Allowance Issued in European Patent Application No. 18843586.1", dated Jun. 9, 2023, 2 Pages.
"Notice of Allowance Issued in European Patent Application No. 1884386.1", dated Mar. 14, 2023, 8 Pages.
"Final Office Action Issued in U.S. Appl. No. 17/571,799", dated Apr. 25, 2023, 31 Pages.
"Notice of Allowance Issued in U.S. Appl. No. 17/696,165", dated Apr. 26, 2023, 7 Pages.
"Non-Final Office Action Issued in U.S. Appl. No. 17/571,799", dated Jul. 27, 2023, 29 Pages.
"Non Final Office Action issued in U.S. Appl. No. 17/210,233", dated Oct. 23, 2023, 47 Pages.
"Non Final Office Action issued in U.S. Appl. No. 17/846,355", dated Sep. 27, 2023, 16 Pages.

\* cited by examiner

FIG. 13A

BRIAN CONNOR
22 YO, DOB 11/4/1995
FEVER, COUGH

HI BRIAN. I AM DOCTOR JONES.

HI DOCTOR JONES.

WHAT BRINGS YOU TO US TODAY? I SAW YOU HAVE HAD SOME FEVER?

YES, IT'S BEEN GOING ON FOR A FEW DAYS NOW. THIS MORNING I HAD 101 AND COULDN'T EVEN GO UP A FLIGHT OF STAIRS. SO I CAME HERE IN A HURRY.

HOW LONG HAS THIS BEEN GOING ON? YOU SAID A FEW DAYS. SINCE FRIDAY?

IT STARTED EARLY SATURDAY. I STARTED TO COUGH, BUT NOT MUCH. BY SUNDAY IT GOT REALLY BAD. THAT'S WHEN I NOTICED I MAY HAVE FEVER.

234

EXAM & ROS

SYSTEMIC
FEVER
TEMP
CHILLS
HEADACHE
ACHING MUSCLES
AND JOINT
STIFFNESS
WEAKNESS

RESPIRATORY
COUGH
SHORTNESS OF BREATH
CHEST
THORACIC PAIN
WHEN BREATHING
RETROSTERNAL
TRACHEAL PAIN
PLEURITIC PAIN
CHEST SOUNDS
RALES
LIQUID IN LUNGS
INFLAMMATION
LATERALITY
LEFT
RIGHT
CENTRAL

OTHER
BR
RR
PULSE
SMOKING STATUS
SKIN COLOR
PREVIOUS HISTORY
OTHER HISTORY
CURRENT MEDS

DIFFERENTIAL DIAGNOSIS
COMMON COLD
BRONCHITIS
INFLUENZA
PNEUMONIA
...
VIRAL/BACTERIAL

PROCEDURES
CHEST X-RAY
BLOOD PANEL

MEDICATIONS
TYLENOL/ACETIMENOPHEN
IBUPRUFEN
DECONGESTANTS
ROBUTUSSIN
VENTOLIN
CODEIN
ANTI-VIRAL THERAPY
ANTI-BACTERIAL THERAPY
INHALER
COUGH SYRUP
...

EENT
THYROID
NECK
SORE THROAT
STUFFY OR RUNNY
NOSE
HOARSENESS
EYES
REDNESS
WATERY

NEURO
CONFUSION
DROWSINESS
CONVULSIONS
MENINGITIS

INSTRUCTIONS
FLUIDS
BED-REST
HOT LIQUIDS
SEEK HELP IF SYMPTOMS WORSEN
FOLLOW-UP AFTER 2 DAYS

240

| BRIAN CONNOR | |
|---|---|
| 22 YO, DOB 11/4/1995 | FEVER, COUGH |

| SUBJECTIVE | |
|---|---|
| COUGH, WORSE AT NIGHT | GETS BETTER DURING THE DAY |
| STARTED 3 DAYS AGO | COULDN'T GO UP A FLIGHT OF STAIRS |
| DIFFICULTY BREATHING AT NIGHT | NON-SMOKER |
| NO CHILLS | YELLOWISH GREEN PHLEGM |
| FEVER 101 | NO FLUIDS IN THE FLUIDS |
| TOOK ROBUTUSSIN | OTHERWISE HEALTHY |

OBJECTIVE:
BLOOD PRESSURE IS 120/80, PULSE IS 90 AND REGULAR, TEMPERATURE IS 101° ORALLY, RESPIRATORY RATE IS 18

HEENT ARE NEGATIVE, NECK IS SUPPLE, THYROID IS NOT ENLARGED.

LUNGS SHOW INSPIRATORY AND EXPIRATORY WHEEZES OVER THE MIDDLE LUNG FIELDS. THERE ARE SCATTERED RALES. THERE IS NO DULLNESS, EGOPHONY, OR DECREASED FREMITUS.

REMAINDER OF EXAM IS NEGATIVE.

IMPRESSION/ASSESSMENT:
PROBABLE ACUTE BRONCHITIS. IT IS MOST LIKELY VIRAL.

PLAN:
WILL PRESCRIBE CODEINE COUGH SYRUP FOR BEDTIME, AND A VENTOLIN INHALER TO USE 4 TIMES A DAY. PATIENT IS INSTRUCTED TO CALL OR RETURN IMMEDIATELY IF HIS TEMPERATURE WORSENS OR IF HIS SYMPTOMS DO NOT RESOLVE.

*FIG. 14A*

BRIAN CONNOR  FEVER, COUGH
22 YO, DOB 11/4/1995

SUBJECTIVE:
THE PATIENT COMES IN TODAY WITH A COMPLAINT OF COUGH AND MILD DYSPNEA. 3 DAYS AGO THE PATIENT NOTED THE FAIRLY ABRUPT ONSET OF COUGHING. INITIALLY THE COUGH WAS DRY, BUT 2 DAYS AGO BEGAN TO BE PRODUCTIVE OF PHLEGM. THE PHLEGM WAS INITIALLY CLEAR, AND THEN BECAME YELLOW TO YELLOW-GREEN. THE PATIENT NOTES THAT THE COUGH WAS WORSE WHEN HE LAY DOWN IN THE EVENING AND MADE SLEEP DIFFICULT, AND SEEMED TO IMPROVE SOMEWHAT IN THE MIDDLE OF THE DAY. YESTERDAY THE COUGH BECAME MORE FREQUENT, THE PHLEGM BECAME THICKER, HE DEVELOPED A TEMPERATURE TO 101° ORALLY, AND HE TRIED TO TAKE AN OVER-THE-COUNTER COUGH REMEDY (ROBITUSSIN-DM). TODAY THE PATIENT BECAME MODESTLY SHORT OF BREATH AFTER CLIMBING A FLIGHT OF STAIRS AND REQUESTED AN URGENT OFFICE VISIT. THE PATIENT DENIES ANY SHAKING CHILLS, IS NOT A CIGARETTE SMOKER, HAS NOT BEEN SHORT OF BREATH AT REST, AND DOES NOT REMEMBER ANY PREVIOUS SUCH EPISODES.

OBJECTIVE:
BLOOD PRESSURE IS 120/80, PULSE IS 90 AND REGULAR, TEMPERATURE IS 101° ORALLY, RESPIRATORY RATE IS 18

HEENT ARE NEGATIVE. NECK IS SUPPLE, THYROID IS NOT ENLARGED.

LUNGS SHOW INSPIRATORY AND EXPIRATORY WHEEZES OVER THE MIDDLE LUNG FIELDS. THERE ARE SCATTERED RALES. THERE IS NO DULLNESS, EGOPHONY, OR DECREASED FREMITUS.

REMAINDER OF EXAM IS NEGATIVE.

IMPRESSION/ASSESSMENT:
PROBABLE ACUTE BRONCHITIS. IT IS MOST LIKELY VIRAL.

PLAN:
WILL PRESCRIBE CODEINE COUGH SYRUP FOR BEDTIME, AND A VENTOLIN INHALER TO USE 4 TIMES A DAY. PATIENT IS INSTRUCTED TO CALL OR RETURN IMMEDIATELY IF HIS TEMPERATURE WORSENS OR IF HIS SYMPTOMS DO NOT RESOLVE.

*FIG. 14B*

AUTOMATED CLINICAL DOCUMENTATION SYSTEM AND METHOD

RELATED APPLICATION(S)

This application is a continuation of U.S. Non-Provisional application Ser. No. 16/058,912, filed on Aug. 8, 2018, which claims the benefit of the following U.S. Provisional Application Nos. 62/543,762, filed on Aug. 10, 2017; and 62/638,809, filed on Mar. 5, 2018; their entire contents of which are incorporated herein by reference.

TECHNICAL FIELD

This disclosure relates to documentation systems and methods and, more particularly, to automated clinical documentation systems and methods.

BACKGROUND

As is known in the art, clinical documentation is the creation of medical records and documentation that details the medical history of medical patients. As would be expected, traditional clinical documentation includes various types of data, examples of which may include but are not limited to paper-based documents and transcripts, as well as various images and diagrams.

As the world moved from paper-based content to digital content, clinical documentation also moved in that direction, where medical records and documentation were gradually transitioned from stacks of paper geographically-dispersed across multiple locations/institutions to consolidated and readily accessible digital content.

SUMMARY OF DISCLOSURE

In one implementation, a computer-implemented method for synchronizing machine vision and audio is executed on a computing device and includes obtaining encounter information of a patient encounter, wherein the encounter information includes machine vision encounter information and audio encounter information. The machine vision encounter information and the audio encounter information are temporally-aligned to produce a temporarily-aligned encounter recording.

One or more of the following features may be included. The temporarily-aligned encounter recording may be rendered. The machine vision encounter information may be obtained via one or more machine vision systems. The one or more machine vision systems may include one or more of: a visible energy imaging system (e.g., an RGB imaging system); an invisible energy imaging system (e.g., infrared, ultraviolet, laser imaging system); an X-ray imaging system; a SONAR imaging .system; a RADAR imaging system; and a thermal imaging system. The audio encounter information may be obtained via one or more audio sensors. Obtaining encounter information may include utilizing a virtual assistant to prompt the patient to provide at least a portion of the encounter information during a pre-visit portion of the patient encounter. Obtaining encounter information may include utilizing a virtual assistant to prompt the patient to provide at least a portion of the encounter information during a post-visit portion of the patient encounter.

In another implementation, a computer program product resides on a computer readable medium and has a plurality of instructions stored on it. When executed by a processor, the instructions cause the processor to perform operations including obtaining encounter information of a patient encounter, wherein the encounter information includes machine vision encounter information and audio encounter information. The machine vision encounter information and the audio encounter information are temporally-aligned to produce a temporarily-aligned encounter recording.

One or more of the following features may be included. The temporarily-aligned encounter recording may be rendered. The machine vision encounter information may be obtained via one or more machine vision systems. The one or more machine vision systems may include one or more of: a visible energy imaging system (e.g., an RGB imaging system); an invisible energy imaging system (e.g., infrared, ultraviolet, laser imaging system); an X-ray imaging system; a SONAR imaging .system; a RADAR imaging system; and a thermal imaging system. The audio encounter information may be obtained via one or more audio sensors. Obtaining encounter information may include utilizing a virtual assistant to prompt the patient to provide at least a portion of the encounter information during a pre-visit portion of the patient encounter. Obtaining encounter information may include utilizing a virtual assistant to prompt the patient to provide at least a portion of the encounter information during a post-visit portion of the patient encounter.

In another implementation, a computing system includes a processor and memory is configured to perform operations including obtaining encounter information of a patient encounter, wherein the encounter information includes machine vision encounter information and audio encounter information. The machine vision encounter information and the audio encounter information are temporally-aligned to produce a temporarily-aligned encounter recording.

One or more of the following features may be included. The temporarily-aligned encounter recording may be rendered. The machine vision encounter information may be obtained via one or more machine vision systems. The one or more machine vision systems may include one or more of: a visible energy imaging system (e.g., an RGB imaging system); an invisible energy imaging system (e.g., infrared, ultraviolet, laser imaging system); an X-ray imaging system; a SONAR imaging .system; a RADAR imaging system; and a thermal imaging system. The audio encounter information may be obtained via one or more audio sensors. Obtaining encounter information may include utilizing a virtual assistant to prompt the patient to provide at least a portion of the encounter information during a pre-visit portion of the patient encounter. Obtaining encounter information may include utilizing a virtual assistant to prompt the patient to provide at least a portion of the encounter information during a post-visit portion of the patient encounter.

The details of one or more implementations are set forth in the accompanying drawings and the description below. Other features and advantages will become apparent from the description, the drawings, and the claims.

BRIEF DESCRIPTION OF THE DRAWINGS

FIGS. 13A-13E are diagrammatic views of the encounter transcript and semantic frames as generated by the automated clinical documentation process of FIG. 1;

FIGS. 14A-14B are diagrammatic views of a medical record as populated by the automated clinical documentation process of FIG. 1;

Like reference symbols in the various drawings indicate like elements.

DETAILED DESCRIPTION OF THE PREFERRED EMBODIMENTS

Figure 1:
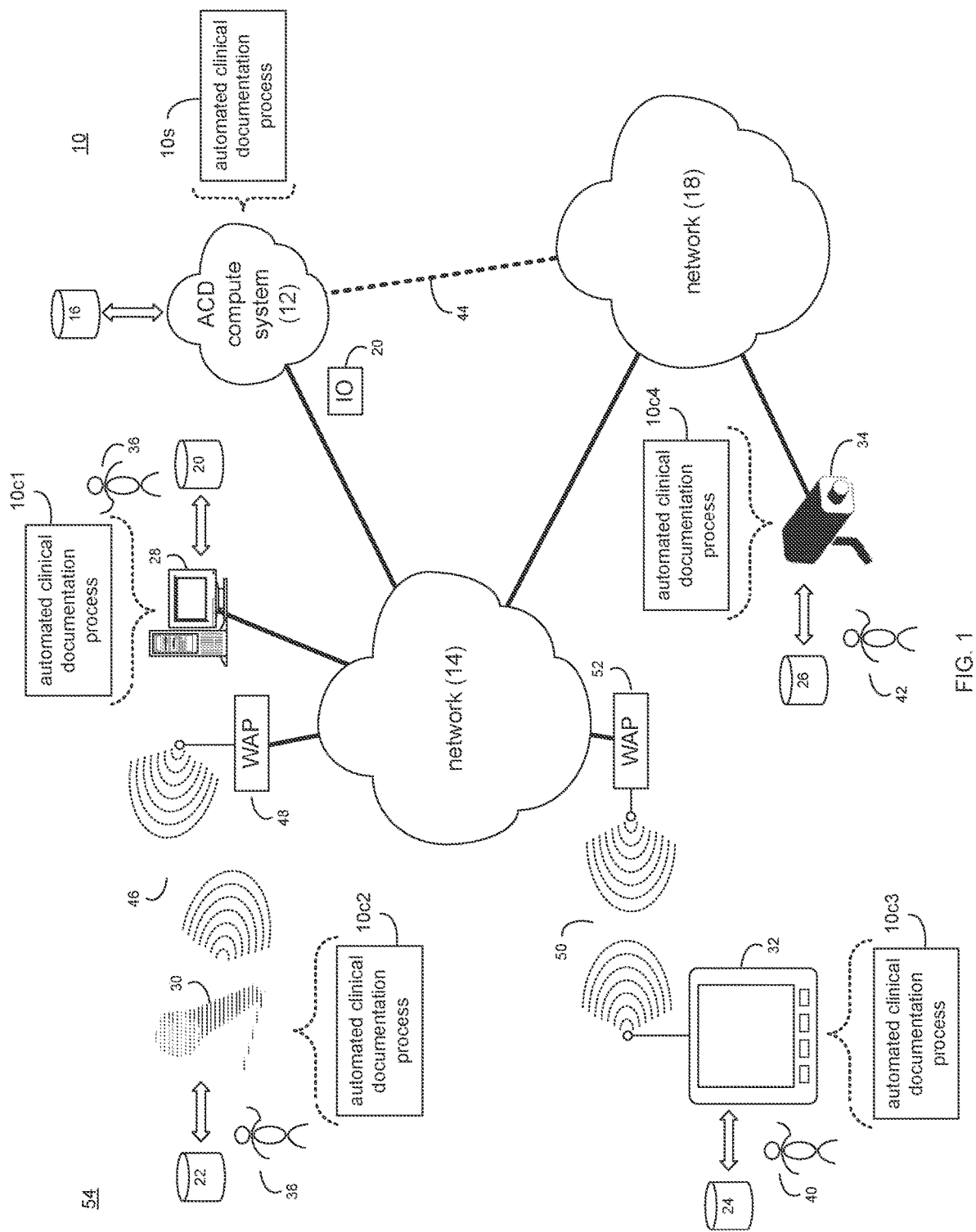
FIG. 1 is a diagrammatic view of an automated clinical documentation compute system and an automated clinical documentation process coupled to a distributed computing network.

System Overview:

Referring to FIG. 1, there is shown automated clinical documentation process 10. As will be discussed below in greater detail, automated clinical documentation process 10 may be configured to automate the collection and processing of clinical encounter information to generate/store/distribute medical records.

Automated clinical documentation process 10 may be implemented as a server-side process, a client-side process, or a hybrid server-side/client-side process. For example, automated clinical documentation process 10 may be implemented as a purely server-side process via automated clinical documentation process 10s. Alternatively, automated clinical documentation process 10 may be implemented as a purely client-side process via one or more of automated clinical documentation process 10c1, automated clinical documentation process 10c2, automated clinical documentation process 10c3, and automated clinical documentation process 10c4. Alternatively still, automated clinical documentation process 10 may be implemented as a hybrid server-side/client-side process via automated clinical documentation process 10s in combination with one or more of automated clinical documentation process 10c1, automated clinical documentation process 10c2, automated clinical documentation process 10c3, and automated clinical documentation process 10c4.

Accordingly, automated clinical documentation process 10 as used in this disclosure may include any combination of automated clinical documentation process 10s, automated clinical documentation process 10c1, automated clinical documentation process 10c2, automated clinical documentation process 10c3, and automated clinical documentation process 10c4.

Automated clinical documentation process 10s may be a server application and may reside on and may be executed by automated clinical documentation (ACD) compute system 12, which may be connected to network 14 (e.g., the Internet or a local area network). ACD compute system 12 may include various components, examples of which may include but are not limited to: a personal computer, a server computer, a series of server computers, a mini computer, a mainframe computer, one or more Network Attached Storage (NAS) systems, one or more Storage Area Network (SAN) systems, one or more Platform as a Service (PaaS) systems, one or more Infrastructure as a Service (IaaS) systems, one or more Software as a Service (SaaS) systems, a cloud-based computational system, and a cloud-based storage platform.

As is known in the art, a SAN may include one or more of a personal computer, a server computer, a series of server computers, a mini computer, a mainframe computer, a RAID device and a NAS system. The various components of ACD compute system 12 may execute one or more operating systems, examples of which may include but are not limited to: Microsoft Windows Server™; Redhat Linux™, Unix, or a custom operating system, for example.

The instruction sets and subroutines of automated clinical documentation process 10s, which may be stored on storage device 16 coupled to ACD compute system 12, may be executed by one or more processors (not shown) and one or more memory architectures (not shown) included within ACD compute system 12. Examples of storage device 16 may include but are not limited to: a hard disk drive; a RAID device; a random access memory (RAM); a read-only memory (ROM); and all forms of flash memory storage devices.

Network 14 may be connected to one or more secondary networks (e.g., network 18), examples of which may include but are not limited to: a local area network; a wide area network; or an intranet, for example.

Various IO requests (e.g. IO request 20) may be sent from automated clinical documentation process 10s, automated clinical documentation process 10c1, automated clinical documentation process 10c2, automated clinical documentation process 10c3 and/or automated clinical documentation process 10c4 to ACD compute system 12. Examples of IO request 20 may include but are not limited to data write requests (i.e. a request that content be written to ACD compute system 12) and data read requests (i.e. a request that content be read from ACD compute system 12).

The instruction sets and subroutines of automated clinical documentation process 10c1, automated clinical documentation process 10c2, automated clinical documentation process 10c3 and/or automated clinical documentation process 10c4, which may be stored on storage devices 20, 22, 24, 26 (respectively) coupled to ACD client electronic devices 28, 30, 32, 34 (respectively), may be executed by one or more processors (not shown) and one or more memory architectures (not shown) incorporated into ACD client electronic devices 28, 30, 32, 34 (respectively). Storage devices 20, 22, 24, 26 may include but are not limited to: hard disk drives; optical drives; RAID devices; random access memories (RAM); read-only memories (ROM), and all forms of flash memory storage devices. Examples of ACD client electronic devices 28, 30, 32, 34 may include, but are not limited to, personal computing device 28 (e.g., a smart phone, a personal digital assistant, a laptop computer, a notebook computer, and a desktop computer), audio input device 30 (e.g., a handheld microphone, a lapel microphone, an embedded microphone (such as those embedded within eyeglasses, smart phones, tablet computers and/or watches) and an audio recording device), display device 32 (e.g., a tablet computer, a computer monitor, and a smart television), machine vision input device 34 (e.g., an RGB imaging system, an infrared imaging system, an ultraviolet imaging system, a laser imaging system, a SONAR imaging system, a RADAR imaging system, and a thermal imaging system), a hybrid device (e.g., a single device that includes the functionality of one or more of the above-references devices; not shown), an audio rendering device (e.g., a speaker system, a headphone system, or an earbud system; not shown), various medical devices (e.g., medical imaging equipment, heart monitoring machines, body weight scales, body temperature thermometers, and blood pressure machines; not shown), and a dedicated network device (not shown).

Users 36, 38, 40, 42 may access ACD compute system 12 directly through network 14 or through secondary network 18. Further, ACD compute system 12 may be connected to network 14 through secondary network 18, as illustrated with link line 44.

The various ACD client electronic devices (e.g., ACD client electronic devices 28, 30, 32, 34) may be directly or indirectly coupled to network 14 (or network 18). For example, personal computing device 28 is shown directly coupled to network 14 via a hardwired network connection. Further, machine vision input device 34 is shown directly coupled to network 18 via a hardwired network connection. Audio input device 30 is shown wirelessly coupled to network 14 via wireless communication channel 46 established between audio input device 30 and wireless access point (i.e., WAP) 48, which is shown directly coupled to network 14. WAP 48 may be, for example, an IEEE 802.11a, 802.11b, 802.11g, 802.11n, Wi-Fi, and/or Bluetooth device that is capable of establishing wireless communication channel 46 between audio input device 30 and WAP 48. Display device 32 is shown wirelessly coupled to network 14 via wireless communication channel 50 established between display device 32 and WAP 52, which is shown directly coupled to network 14.

The various ACD client electronic devices (e.g., ACD client electronic devices 28, 30, 32, 34) may each execute an operating system, examples of which may include but are not limited to Microsoft Windows™, Apple Macintosh™, Redhat Linux™, or a custom operating system, wherein the combination of the various ACD client electronic devices (e.g., ACD client electronic devices 28, 30, 32, 34) and ACD compute system 12 may form modular ACD system 54.

Figure 2:
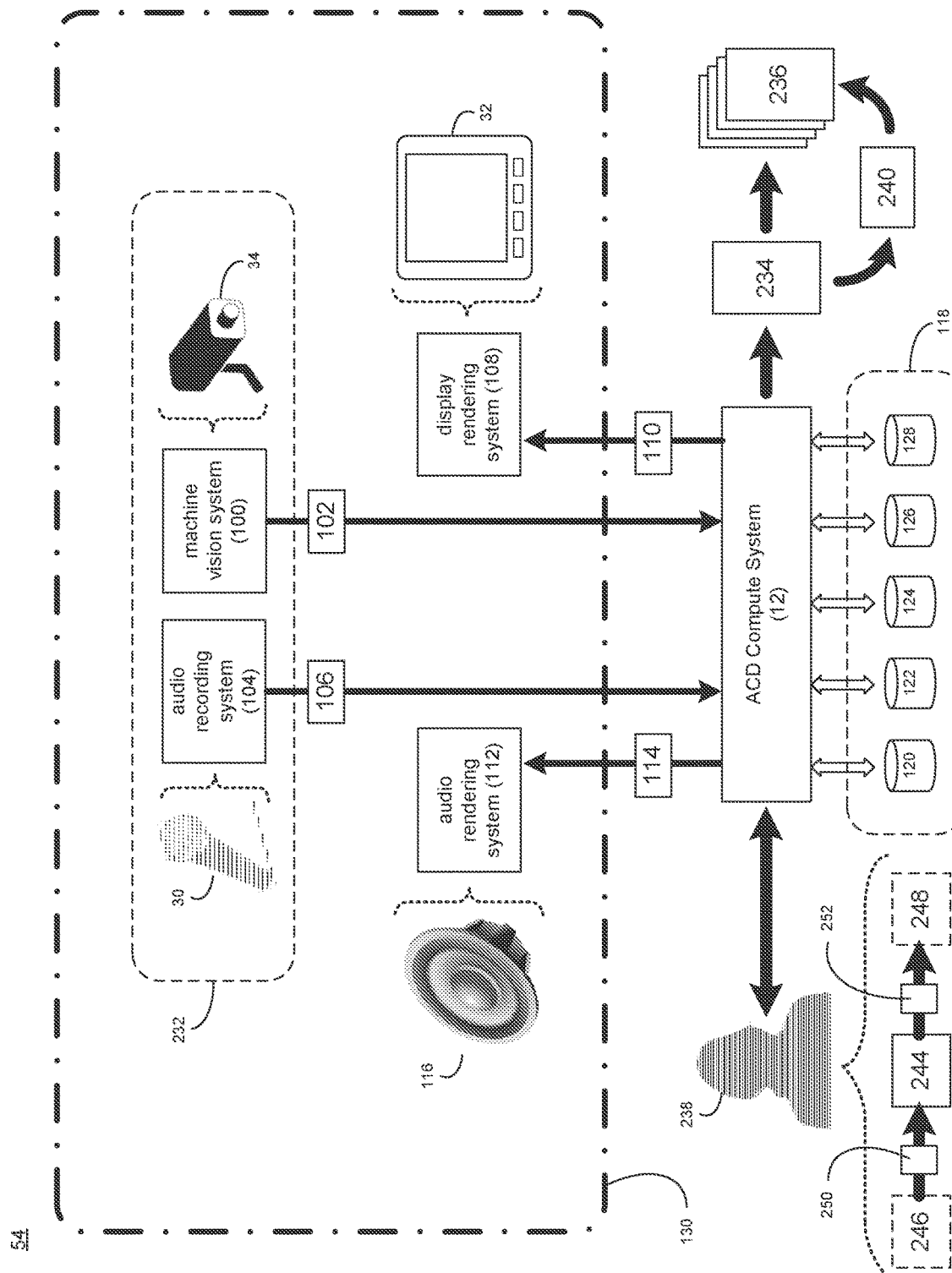
FIG. 2 is a diagrammatic view of a modular ACD system incorporating the automated clinical documentation compute system of FIG. 1.

The Automated Clinical Documentation System:

Referring also to FIG. 2, there is shown a simplified exemplary embodiment of modular ACD system 54 that is configured to automate clinical documentation. Modular ACD system 54 may include: machine vision system 100 configured to obtain machine vision encounter information 102 concerning a patient encounter; audio recording system 104 configured to obtain audio encounter information 106 concerning the patient encounter; and a compute system (e.g., ACD compute system 12) configured to receive machine vision encounter information 102 and audio encounter information 106 from machine vision system 100 and audio recording system 104 (respectively). Modular ACD system 54 may also include: display rendering system 108 configured to render visual information 110; and audio rendering system 112 configured to render audio information 114, wherein ACD compute system 12 may be configured to provide visual information 110 and audio information 114 to display rendering system 108 and audio rendering system 112 (respectively).

Example of machine vision system 100 may include but are not limited to: one or more ACD client electronic devices (e.g., ACD client electronic device 34, examples of which may include but are not limited to an RGB imaging system, an infrared imaging system, a ultraviolet imaging system, a laser imaging system, a SONAR imaging system, a RADAR imaging system, and a thermal imaging system). Examples of audio recording system 104 may include but are not limited to: one or more ACD client electronic devices (e.g., ACD client electronic device 30, examples of which may include but are not limited to a handheld microphone, a lapel microphone, an embedded microphone (such as those embedded within eyeglasses, smart phones, tablet computers and/or watches) and an audio recording device). Examples of display rendering system 108 may include but are not limited to: one or more ACD client electronic devices (e.g., ACD client electronic device 32, examples of which may include but are not limited to a tablet computer, a computer monitor, and a smart television). Examples of audio rendering system 112 may include but are not limited to: one or more ACD client electronic devices (e.g., audio rendering device 116, examples of which may include but are not limited to a speaker system, a headphone system, and an earbud system).

As will be discussed below in greater detail, ACD compute system 12 may be configured to access one or more datasources 118 (e.g., plurality of individual datasources 120, 122, 124, 126, 128), examples of which may include but are not limited to one or more of a user profile datasource, a voice print datasource, a voice characteristics datasource (e.g., for adapting the automated speech recognition models), a face print datasource, a humanoid shape datasource, an utterance identifier datasource, a wearable token identifier datasource, an interaction identifier datasource, a medical conditions symptoms datasource, a prescriptions compatibility datasource, a medical insurance coverage datasource, and a home healthcare datasource. While in this particular example, five different examples of datasources 118, are shown, this is for illustrative purposes only and is not intended to be a limitation of this disclosure, as other configurations are possible and are considered to be within the scope of this disclosure.

As will be discussed below in greater detail, modular ACD system 54 may be configured to monitor a monitored space (e.g., monitored space 130) in a clinical environment, wherein examples of this clinical environment may include but are not limited to: a doctor's office, a medical facility, a medical practice, a medical lab, an urgent care facility, a medical clinic, an emergency room, an operating room, a hospital, a long term care facility, a rehabilitation facility, a nursing home, and a hospice facility. Accordingly, an example of the above-referenced patient encounter may include but is not limited to a patient visiting one or more of the above-described clinical environments (e.g., a doctor's office, a medical facility, a medical practice, a medical lab, an urgent care facility, a medical clinic, an emergency room, an operating room, a hospital, a long term care facility, a rehabilitation facility, a nursing home, and a hospice facility).

Machine vision system 100 may include a plurality of discrete machine vision systems when the above-described clinical environment is larger or a higher level of resolution is desired. As discussed above, examples of machine vision system 100 may include but are not limited to: one or more ACD client electronic devices (e.g., ACD client electronic device 34, examples of which may include but are not limited to an RGB imaging system, an infrared imaging system, an ultraviolet imaging system, a laser imaging system, a SONAR imaging system, a RADAR imaging system, and a thermal imaging system). Accordingly, machine vision system 100 may include one or more of each of an RGB imaging system, an infrared imaging systems, an ultraviolet imaging systems, a laser imaging system, a SONAR imaging system, a RADAR imaging system, and a thermal imaging system.

Audio recording system 104 may include a plurality of discrete audio recording systems when the above-described clinical environment is larger or a higher level of resolution is desired. As discussed above, examples of audio recording system 104 may include but are not limited to: one or more ACD client electronic devices (e.g., ACD client electronic device 30, examples of which may include but are not limited to a handheld microphone, a lapel microphone, an embedded microphone (such as those embedded within eyeglasses, smart phones, tablet computers and/or watches) and an audio recording device). Accordingly, audio recording system 104 may include one or more of each of a handheld microphone, a lapel microphone, an embedded microphone (such as those embedded within eyeglasses, smart phones, tablet computers and/or watches) and an audio recording device.

Display rendering system 108 may include a plurality of discrete display rendering systems when the above-described clinical environment is larger or a higher level of resolution is desired. As discussed above, examples of display rendering system 108 may include but are not limited to: one or more ACD client electronic devices (e.g., ACD client electronic device 32, examples of which may include but are not limited to a tablet computer, a computer monitor, and a smart television). Accordingly, display rendering system 108 may include one or more of each of a tablet computer, a computer monitor, and a smart television.

Audio rendering system 112 may include a plurality of discrete audio rendering systems when the above-described clinical environment is larger or a higher level of resolution is desired. As discussed above, examples of audio rendering system 112 may include but are not limited to: one or more ACD client electronic devices (e.g., audio rendering device 116, examples of which may include but are not limited to a speaker system, a headphone system, or an earbud system). Accordingly, audio rendering system 112 may include one or more of each of a speaker system, a headphone system, or an earbud system.

ACD compute system 12 may include a plurality of discrete compute systems. As discussed above, ACD compute system 12 may include various components, examples of which may include but are not limited to: a personal computer, a server computer, a series of server computers, a mini computer, a mainframe computer, one or more Network Attached Storage (NAS) systems, one or more Storage Area Network (SAN) systems, one or more Platform as a Service (PaaS) systems, one or more Infrastructure as a Service (IaaS) systems, one or more Software as a Service (SaaS) systems, a cloud-based computational system, and a cloud-based storage platform. Accordingly, ACD compute system 12 may include one or more of each of a personal computer, a server computer, a series of server computers, a mini computer, a mainframe computer, one or more Network Attached Storage (NAS) systems, one or more Storage Area Network (SAN) systems, one or more Platform as a Service (PaaS) systems, one or more Infrastructure as a Service (IaaS) systems, one or more Software as a Service (SaaS) systems, a cloud-based computational system, and a cloud-based storage platform.

Figure 3:
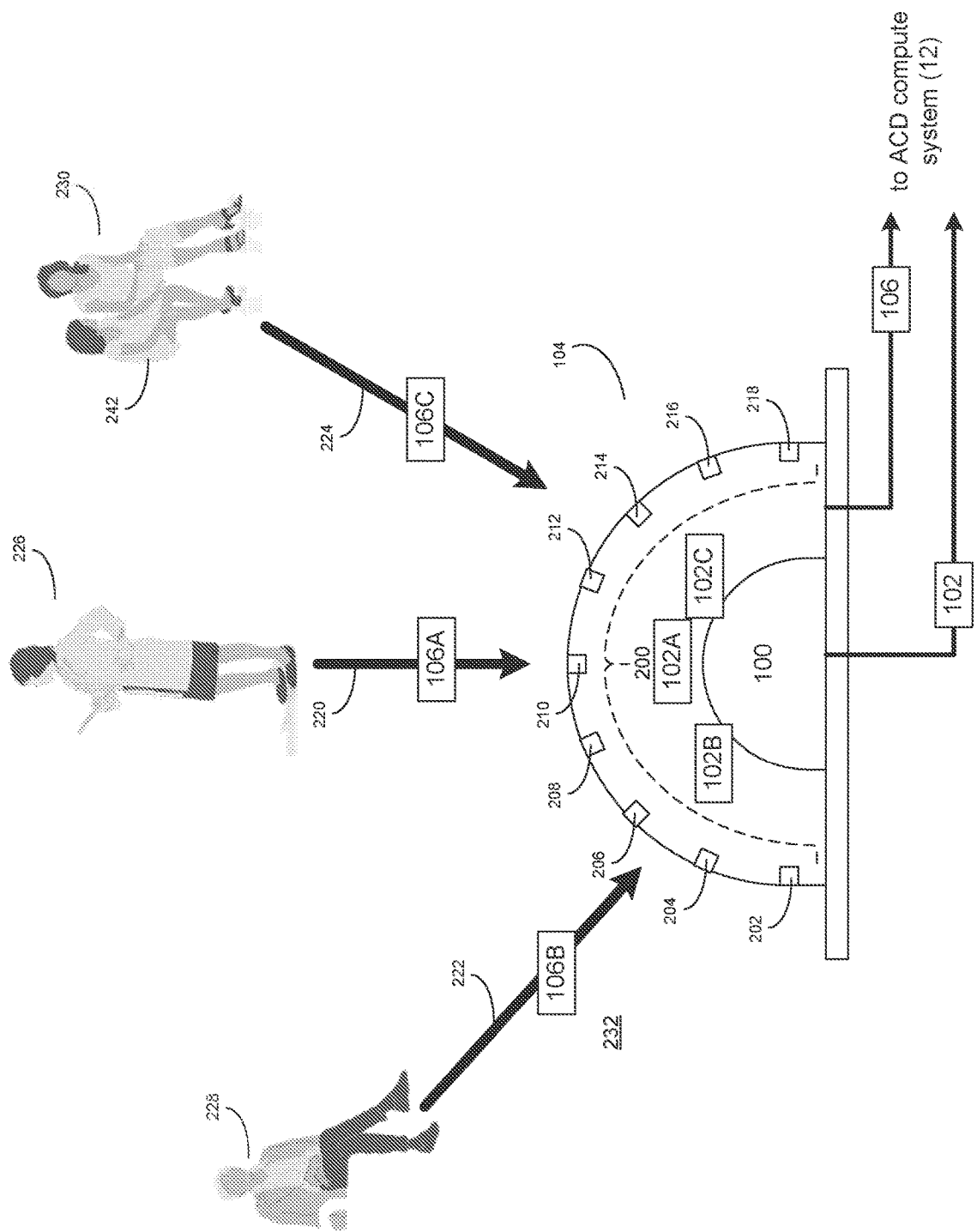
FIG. 3 is a diagrammatic view of a mixed-media ACD device included within the modular ACD system of FIG. 2.

Referring also to FIG. 3, audio recording system 104 may include directional microphone array 200 having a plurality of discrete microphone assemblies. For example, audio recording system 104 may include a plurality of discrete audio acquisition devices (e.g., audio acquisition devices 202, 204, 206, 208, 210, 212, 214, 216, 218) that may form microphone array 200. As will be discussed below in greater detail, modular ACD system 54 may be configured to form one or more audio recording beams (e.g., audio recording beams 220, 222, 224) via the discrete audio acquisition devices (e.g., audio acquisition devices 202, 204, 206, 208, 210, 212, 214, 216, 218) included within audio recording system 104.

For example, modular ACD system 54 may be further configured to steer the one or more audio recording beams (e.g., audio recording beams 220, 222, 224) toward one or more encounter participants (e.g., encounter participants 226, 228, 230) of the above-described patient encounter. Examples of the encounter participants (e.g., encounter participants 226, 228, 230) may include but are not limited to: medical professionals (e.g., doctors, nurses, physician's assistants, lab technicians, physical therapists, scribes (e.g., a transcriptionist) and/or staff members involved in the patient encounter), patients (e.g., people that are visiting the above-described clinical environments for the patient encounter), and third parties (e.g., friends of the patient, relatives of the patient and/or acquaintances of the patient that are involved in the patient encounter).

Accordingly, modular ACD system 54 and/or audio recording system 104 may be configured to utilize one or more of the discrete audio acquisition devices (e.g., audio acquisition devices 202, 204, 206, 208, 210, 212, 214, 216, 218) to form an audio recording beam. For example, modular ACD system 54 and/or audio recording system 104 may be configured to utilize audio acquisition device 210 to form audio recording beam 220, thus enabling the capturing of audio (e.g., speech) produced by encounter participant 226 (as audio acquisition device 210 is pointed to (i.e., directed toward) encounter participant 226). Additionally, modular ACD system 54 and/or audio recording system 104 may be configured to utilize audio acquisition devices 204, 206 to form audio recording beam 222, thus enabling the capturing of audio (e.g., speech) produced by encounter participant 228 (as audio acquisition devices 204, 206 are pointed to (i.e., directed toward) encounter participant 228). Additionally, modular ACD system 54 and/or audio recording system 104 may be configured to utilize audio acquisition devices 212, 214 to form audio recording beam 224, thus enabling the capturing of audio (e.g., speech) produced by encounter participant 230 (as audio acquisition devices 212, 214 are pointed to (i.e., directed toward) encounter participant 230). Further, modular ACD system 54 and/or audio recording system 104 may be configured to utilize null-steering precoding to cancel interference between speakers and/or noise.

As is known in the art, null-steering precoding is a method of spatial signal processing by which a multiple antenna transmitter may null multiuser interference signals in wireless communications, wherein null-steering precoding may mitigate the impact off background noise and unknown user interference.

In particular, null-steering precoding may be a method of beamforming for narrowband signals that may compensate for delays of receiving signals from a specific source at different elements of an antenna array. In general and to improve performance of the antenna array, in incoming signals may be summed and averaged, wherein certain signals may be weighted and compensation may be made for signal delays.

Machine vision system 100 and audio recording system 104 may be stand-alone devices (as shown in FIG. 2). Additionally/alternatively, machine vision system 100 and audio recording system 104 may be combined into one package to form mixed-media ACD device 232. For example, mixed-media ACD device 232 may be configured to be mounted to a structure (e.g., a wall, a ceiling, a beam, a column) within the above-described clinical environments (e.g., a doctor's office, a medical facility, a medical practice, a medical lab, an urgent care facility, a medical clinic, an emergency room, an operating room, a hospital, a long term care facility, a rehabilitation facility, a nursing home, and a hospice facility), thus allowing for easy installation of the same. Further, modular ACD system 54 may be configured to include a plurality of mixed-media ACD devices (e.g., mixed-media ACD device 232) when the above-described clinical environment is larger or a higher level of resolution is desired.

The Mixed-Media Automated Clinical Documentation Device:

Modular ACD system 54 may be further configured to steer the one or more audio recording beams (e.g., audio recording beams 220, 222, 224) toward one or more encounter participants (e.g., encounter participants 226, 228, 230) of the patient encounter based, at least in part, upon machine vision encounter information 102. As discussed above, mixed-media ACD device 232 (and machine vision system 100/audio recording system 104 included therein) may be configured to monitor one or more encounter participants (e.g., encounter participants 226, 228, 230) of a patient encounter.

Specifically and as will be discussed below in greater detail, machine vision system 100 (either as a stand-alone system or as a component of mixed-media ACD device 232) may be configured to detect humanoid shapes within the above-described clinical environments (e.g., a doctor's office, a medical facility, a medical practice, a medical lab, an urgent care facility, a medical clinic, an emergency room, an operating room, a hospital, a long term care facility, a rehabilitation facility, a nursing home, and a hospice facility). And when these humanoid shapes are detected by machine vision system 100, modular ACD system 54 and/or audio recording system 104 may be configured to utilize one or more of the discrete audio acquisition devices (e.g., audio acquisition devices 202, 204, 206, 208, 210, 212, 214, 216, 218) to form an audio recording beam (e.g., audio recording beams 220, 222, 224) that is directed toward each of the detected humanoid shapes (e.g., encounter participants 226, 228, 230).

As discussed above, ACD compute system 12 may be configured to receive machine vision encounter information 102 and audio encounter information 106 from machine vision system 100 and audio recording system 104 (respectively); and may be configured to provide visual information 110 and audio information 114 to display rendering system 108 and audio rendering system 112 (respectively). Depending upon the manner in which modular ACD system 54 (and/or mixed-media ACD device 232) is configured, ACD compute system 12 may be included within mixed-media ACD device 232 or external to mixed-media ACD device 232.

The Automated Clinical Documentation Process:

As discussed above, ACD compute system 12 may execute all or a portion of automated clinical documentation process 10, wherein the instruction sets and subroutines of automated clinical documentation process 10 (which may be stored on one or more of e.g., storage devices 16, 20, 22, 24, 26) may be executed by ACD compute system 12 and/or one or more of ACD client electronic devices 28, 30, 32, 34.

Figure 4:
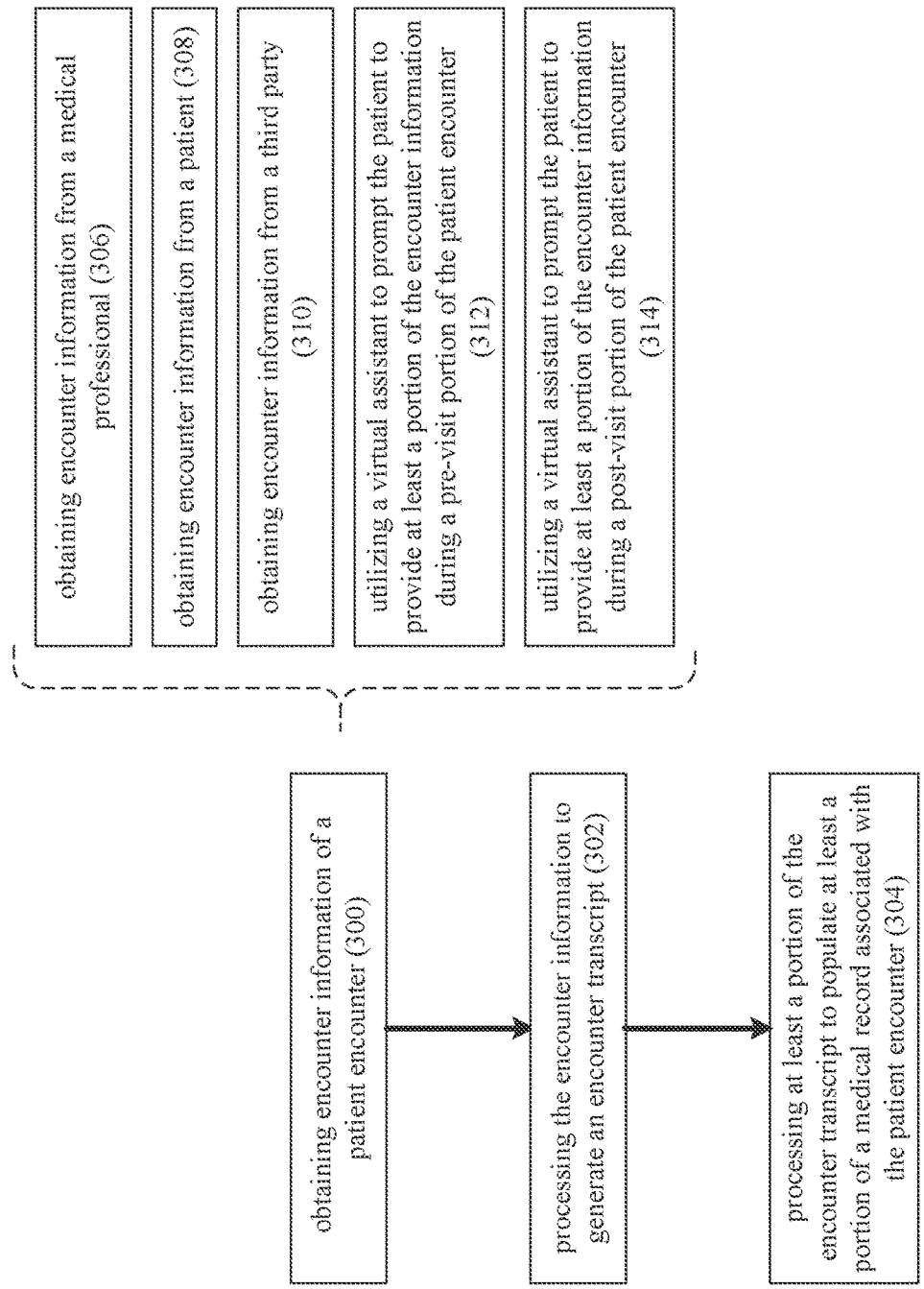
FIG. 4 is a flow chart of one implementation of the automated clinical documentation process of FIG. 1.

As discussed above, automated clinical documentation process 10 may be configured to automate the collection and processing of clinical encounter information to generate/store/distribute medical records. Accordingly and referring also to FIG. 4, automated clinical documentation process 10 may be configured to obtain 300 encounter information (e.g., machine vision encounter information 102 and/or audio encounter information 106) of a patient encounter (e.g., a visit to a doctor's office). Automated clinical documentation process 10 may further be configured to process 302 the encounter information (e.g., machine vision encounter information 102 and/or audio encounter information 106) to generate an encounter transcript (e.g., encounter transcript 234), wherein automated clinical documentation process 10 may then process 304 at least a portion of the encounter transcript (e.g., encounter transcript 234) to populate at least a portion of a medical record (e.g., medical record 236) associated with the patient encounter (e.g., the visit to the doctor's office). Encounter transcript 234 and/or medical record 236 may be reviewed by a medical professional involved with the patient encounter (e.g., a visit to a doctor's office) to determine the accuracy of the same and/or make corrections to the same.

For example, a scribe involved with (or assigned to) the patient encounter (e.g., a visit to a doctor's office) may review encounter transcript 234 and/or medical record 236 to confirm that the same was accurate and/or make corrections to the same. In the event that corrections are made to encounter transcript 234 and/or medical record 236, automated clinical documentation process 10 may utilize these corrections for training/tuning purposes (e.g., to adjust the various profiles associated the participants of the patient encounter) to enhance the future accuracy/efficiency/performance of automated clinical documentation process 10.

Alternatively/additionally, a doctor involved with the patient encounter (e.g., a visit to a doctor's office) may review encounter transcript 234 and/or medical record 236 to confirm that the same was accurate and/or make corrections to the same. In the event that corrections are made to encounter transcript 234 and/or medical record 236, automated clinical documentation process 10 may utilize these corrections for training/tuning purposes (e.g., to adjust the various profiles associated the participants of the patient encounter) to enhance the future accuracy/efficiency/performance of automated clinical documentation process 10.

For example, assume that a patient (e.g., encounter participant 228) visits a clinical environment (e.g., a doctor's office) because they do not feel well. They have a headache, fever, chills, a cough, and some difficulty breathing. In this particular example, a monitored space (e.g., monitored space 130) within the clinical environment (e.g., the doctor's office) may be outfitted with machine vision system 100 configured to obtain machine vision encounter information 102 concerning the patient encounter (e.g., encounter participant 228 visiting the doctor's office) and audio recording system 104 configured to obtain audio encounter information 106 concerning the patient encounter (e.g., encounter participant 228 visiting the doctor's office) via one or more audio sensors (e.g., audio acquisition devices 202, 204, 206, 208, 210, 212, 214, 216, 218).

As discussed above, machine vision system 100 may include a plurality of discrete machine vision systems if the monitored space (e.g., monitored space 130) within the clinical environment (e.g., the doctor's office) is larger or a higher level of resolution is desired, wherein examples of machine vision system 100 may include but are not limited to: an RGB imaging system, an infrared imaging system, an ultraviolet imaging system, a laser imaging system, a SONAR imaging system, a RADAR imaging system, and a thermal imaging system. Accordingly and in certain instances/embodiments, machine vision system 100 may include one or more of each of an RGB imaging system, an infrared imaging system, an ultraviolet imaging system, a laser imaging system, a SONAR imaging system, a RADAR imaging system, and a thermal imaging system positioned throughout monitored space 130, wherein each of these systems may be configured to provide data (e.g., machine vision encounter information 102) to ACD compute system 12 and/or modular ACD system 54.

As also discussed above, audio recording system 104 may include a plurality of discrete audio recording systems if the monitored space (e.g., monitored space 130) within the clinical environment (e.g., the doctor's office) is larger or a higher level of resolution is desired, wherein examples of audio recording system 104 may include but are not limited to: a handheld microphone, a lapel microphone, an embedded microphone (such as those embedded within eyeglasses, smart phones, tablet computers and/or watches) and an audio recording device. Accordingly and in certain instances/embodiments, audio recording system 104 may include one or more of each of a handheld microphone, a lapel microphone, an embedded microphone (such as those embedded within eyeglasses, smart phones, tablet computers and/or watches) and an audio recording device positioned throughout monitored space 130, wherein each of these microphones/devices may be configured to provide data (e.g., audio encounter information 106) to ACD compute system 12 and/or modular ACD system 54.

Since machine vision system 100 and audio recording system 104 may be positioned throughout monitored space 130, all of the interactions between medical professionals (e.g., encounter participant 226), patients (e.g., encounter participant 228) and third parties (e.g., encounter participant 230) that occur during the patient encounter (e.g., encounter participant 228 visiting the doctor's office) within the monitored space (e.g., monitored space 130) of the clinical environment (e.g., the doctor's office) may be monitored/recorded/processed. Accordingly, a patient "check-in" area within monitored space 130 may be monitored to obtain encounter information (e.g., machine vision encounter information 102 and/or audio encounter information 106) during this pre-visit portion of the patient encounter (e.g., encounter participant 228 visiting the doctor's office). Further, various rooms within monitored space 130 may be monitored to obtain encounter information (e.g., machine vision encounter information 102 and/or audio encounter information 106) during these various portions of the patient encounter (e.g., while meeting with the doctor, while vital signs and statistics are obtained, and while imaging is performed). Further, a patient "check-out" area within monitored space 130 may be monitored to obtain encounter information (e.g., machine vision encounter information 102 and/or audio encounter information 106) during this post-visit portion of the patient encounter (e.g., encounter participant 228 visiting the doctor's office). Additionally and via machine vision encounter information 102, visual speech recognition (via visual lip reading functionality) may be utilized by automated clinical documentation process 10 to further effectuate the gathering of audio encounter information 106.

Accordingly and when obtaining 300 encounter information (e.g., machine vision encounter information 102 and/or audio encounter information 106), automated clinical documentation process 10 may: obtain 306 encounter information (e.g., machine vision encounter information 102 and/or audio encounter information 106) from a medical professional (e.g., encounter participant 226); obtain 308 encounter information (e.g., machine vision encounter information 102 and/or audio encounter information 106) from a patient (e.g., encounter participant 228); and/or obtain 310 encounter information (e.g., machine vision encounter information 102 and/or audio encounter information 106) from a third party (e.g., encounter participant 230). Further and when obtaining 300 encounter information (e.g., machine vision encounter information 102 and/or audio encounter information 106), automated clinical documentation process 10 may obtain 300 the encounter information (e.g., machine vision encounter information 102 and/or audio encounter information 106) from previous (related or unrelated) patient encounters. For example, if the current patient encounter is actually the third visit that the patient is making concerning e.g., shortness of breath, the encounter information from the previous two visits (i.e., the previous two patient encounters) may be highly-related and may be obtained 300 by automated clinical documentation process 10.

As will be discussed below in greater detail, when automated clinical documentation process 10 obtains 300 the encounter information, automated clinical documentation process 10 may utilize 312 a virtual assistant (e.g., virtual assistant 238) to prompt the patient (e.g., encounter participant 228) to provide at least a portion of the encounter information (e.g., machine vision encounter information 102 and/or audio encounter information 106) during a pre-visit portion (e.g., a patient intake portion) of the patient encounter (e.g., encounter participant 228 visiting the doctor's office).

Further and as will be discussed below in greater detail, when automated clinical documentation process 10 obtains 300 encounter information, automated clinical documentation process 10 may utilize 314 a virtual assistant (e.g., virtual assistant 238) to prompt the patient (e.g., encounter participant 228) to provide at least a portion of the encounter information (e.g., machine vision encounter information 102 and/or audio encounter information 106) during a post-visit portion (e.g., a patient follow-up portion) of the patient encounter (e.g., encounter participant 228 visiting the doctor's office).

As discussed above, when automated clinical documentation process 10 obtains 300 encounter information, automated clinical documentation process 10 may utilize 312 a virtual assistant (e.g., virtual assistant 238) to prompt the patient (e.g., encounter participant 228) to provide at least a portion of the encounter information (e.g., machine vision encounter information 102 and/or audio encounter information 106) during a pre-visit portion (e.g., a patient intake portion) of the patient encounter (e.g., encounter participant 228 visiting the doctor's office).

As will be discussed below in greater detail, virtual assistant 238 may be configured to aid medical professionals (e.g., doctors, nurses, physician's assistants, lab technicians, physical therapists, scribes (e.g., a transcriptionist) and/or staff members involved in the patient encounter) with the gathering of encounter information (e.g., machine vision encounter information 102 and/or audio encounter information 106) during various portions of the patient encounter (e.g., encounter participant 228 visiting the doctor's office).

Figure 5:
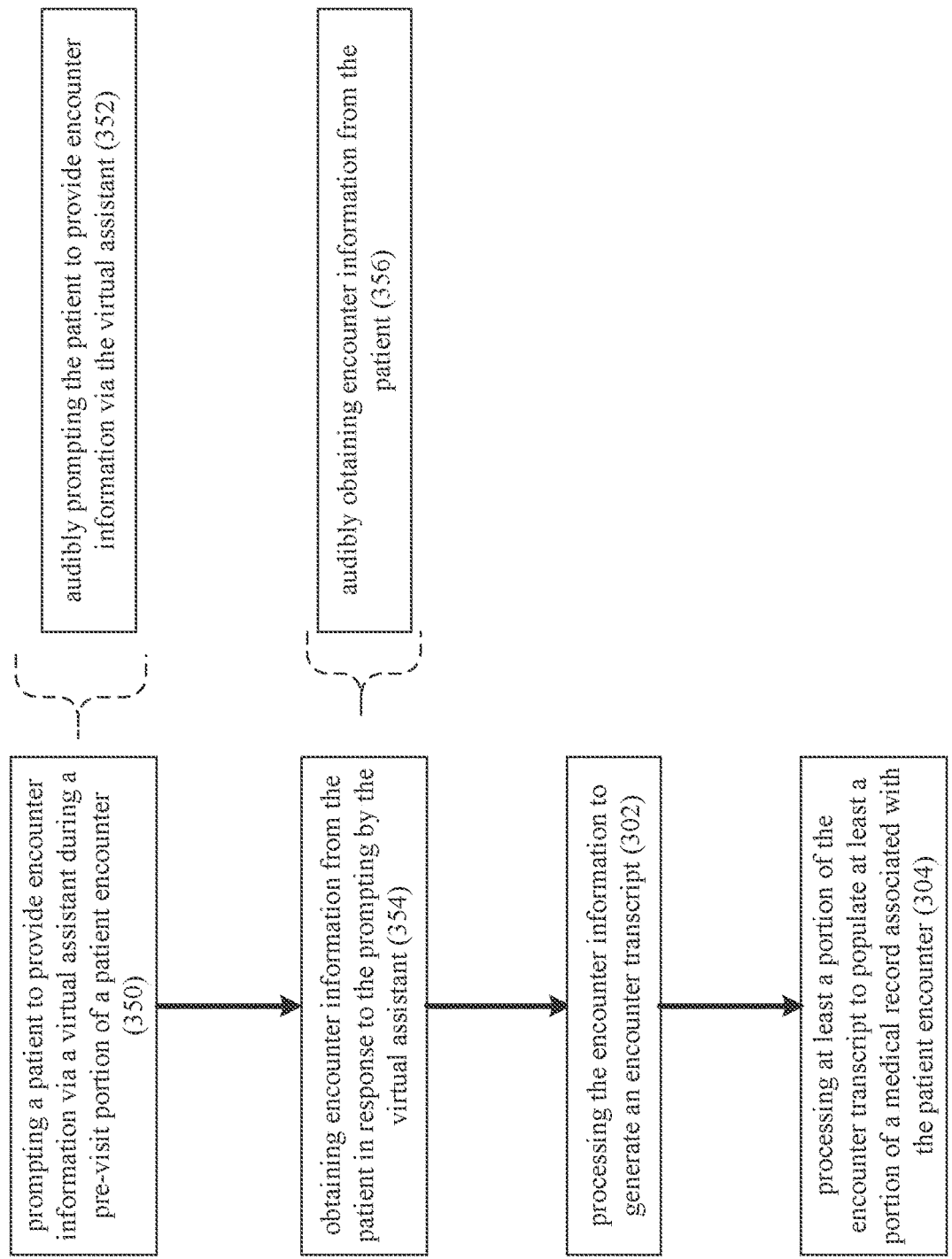
FIG. 5 is a flow chart of another implementation of the automated clinical documentation process of FIG. 1.

Accordingly and referring also to FIG. 5, automated clinical documentation process 10 may be configured to prompt 350 a patient (e.g., encounter participant 228) to provide encounter information (e.g., machine vision encounter information 102 and/or audio encounter information 106) via a virtual assistant (e.g., virtual assistant 238) during a pre-visit portion of a patient encounter (e.g., encounter participant 228 visiting the doctor's office).

For example and upon arriving for the patient encounter (e.g., encounter participant 228 visiting the doctor's office), the patient (e.g., encounter participant 228) may be directed to a "check-in" area within the monitored space (e.g., monitored space 130) of the clinical environment. An example of this "check-in" area may include a booth into which the patient (e.g., encounter participant 228) enters. Upon entering this "check-in" area, the pre-visit portion (e.g., the patient intake portion) of the patient encounter (e.g., encounter participant 228 visiting the doctor's office) may begin.

When prompting 350 the patient (e.g., encounter participant 228) to provide encounter information (e.g., machine vision encounter information 102 and/or audio encounter information 106) via the virtual assistant (e.g., virtual assistant 238), automated clinical documentation process 10 may audibly prompt 352 the patient (e.g., encounter participant 228) to provide encounter information (e.g., machine vision encounter information 102 and/or audio encounter information 106) via the virtual assistant (e.g., virtual assistant 238). For example, virtual assistant 238 may provide (via audio rendering device 116) a cordial greeting to the patient (e.g., encounter participant 228) and ask them if they are checking in for a visit. If the patient (e.g., encounter participant 228) responds affirmatively, virtual assistant 238 may audibly prompt 352 the patient (e.g., encounter participant 228) to provide encounter information (e.g., machine vision encounter information 102 and/or audio encounter information 106), examples of which may include but are not limited to: patient background information; patient current-prescription information; patient insurance information; and patient symptom information.

Therefore, virtual assistant 238 may ask the patient (e.g., encounter participant 228) to provide various pieces of identifying information, examples of which may include but are not limited to: patient name, patient social security number, and patient date of birth, Depending upon the manner in which automated clinical documentation process 10 is configured, machine vision encounter information 102 may be utilized to further enhance/expedite the check-in process. For example and via machine vision encounter information 102, facial recognition functionality may be utilized to positively identify the patient (e.g., encounter participant 228). Additionally and via machine vision encounter information 102, visual speech recognition (via visual lip reading functionality) may be utilized by automated clinical documentation process 10 to further effectuate the gathering of audio encounter information 106. Virtual assistant 238 may ask the patient (e.g., encounter participant 228) to provide additional pieces of information, examples of which may include but are not limited to patient current-prescription information; patient insurance information; and patient symptom information.

While the pre-visit portion of the patient encounter (e.g., encounter participant 228 visiting the doctor's office) is described above as being the point of the patient encounter (e.g., encounter participant 228 visiting the doctor's office) where the patient (e.g., encounter participant 228) is entering the monitored space (e.g., monitored space 130) in a clinical environment, this is for illustrative purposes only and is not intended to be a limitation of this disclosure, as other configurations are possible and are considered to be within the scope of this disclosure. For example, this pre-visit portion of the patient encounter (e.g., encounter participant 228 visiting the doctor's office) may include: automated wellness phone calls, automated wellness text messages, and automated wellness video conferences initiated by virtual assistant 238 and directed toward the patient (e.g., encounter participant 228) or a third party; and/or phone calls, text messages, and video conferences initiated by the patient (e.g., encounter participant 228) or a third party and automatically processed by virtual assistant 238.

During this pre-visit portion (e.g., the patient intake portion) of the patient encounter (e.g., encounter participant 228 visiting the doctor's office), automated clinical documentation process 10 may obtain 354 encounter information (e.g., machine vision encounter information 102 and/or audio encounter information 106) from the patient (e.g., encounter participant 228) in response to the prompting by the virtual assistant (e.g., virtual assistant 238). When obtaining 354 the encounter information (e.g., machine vision encounter information 102 and/or audio encounter information 106) from the patient (e.g., encounter participant 228), automated clinical documentation process 10 may audibly obtain 356 the encounter information (e.g., machine vision encounter information 102 and/or audio encounter information 106) from the patient (e.g., encounter participant 228), thus allowing encounter participant 228 to simply verbalize their answers, wherein this information (e.g., audio encounter information 106) may be received via audio input device 30.

Automated clinical documentation process 10 may then process 302 the encounter information (e.g., machine vision encounter information 102 and/or audio encounter information 106) to generate an encounter transcript (e.g., encounter transcript 234), wherein at least a portion of the encounter transcript (e.g., encounter transcript 234) may be processed 304 to populate at least a portion of a medical record (e.g., medical record 236) associated with the patient encounter (e.g., a visit to a doctor's office).

As discussed above, when automated clinical documentation process 10 obtains 300 encounter information, automated clinical documentation process 10 may utilize 314 a virtual assistant (e.g., virtual assistant 238) to prompt the patient (e.g., encounter participant 228) to provide at least a portion of the encounter information (e.g., machine vision encounter information 102 and/or audio encounter information 106) during a post-visit portion (e.g., a patient follow-up portion) of the patient encounter (e.g., encounter participant 228 visiting the doctor's office.

As discussed above and as will be discussed below in greater detail, virtual assistant 238 may be configured to aid medical professionals (e.g., doctors, nurses, physician's assistants, lab technicians, physical therapists, scribes (e.g., a transcriptionist) and/or staff members involved in the patient encounter) with the gathering of encounter information (e.g., machine vision encounter information 102 and/or audio encounter information 106) during various portions of the patient encounter (e.g., encounter participant 228 visiting the doctor's office).

Figure 6:
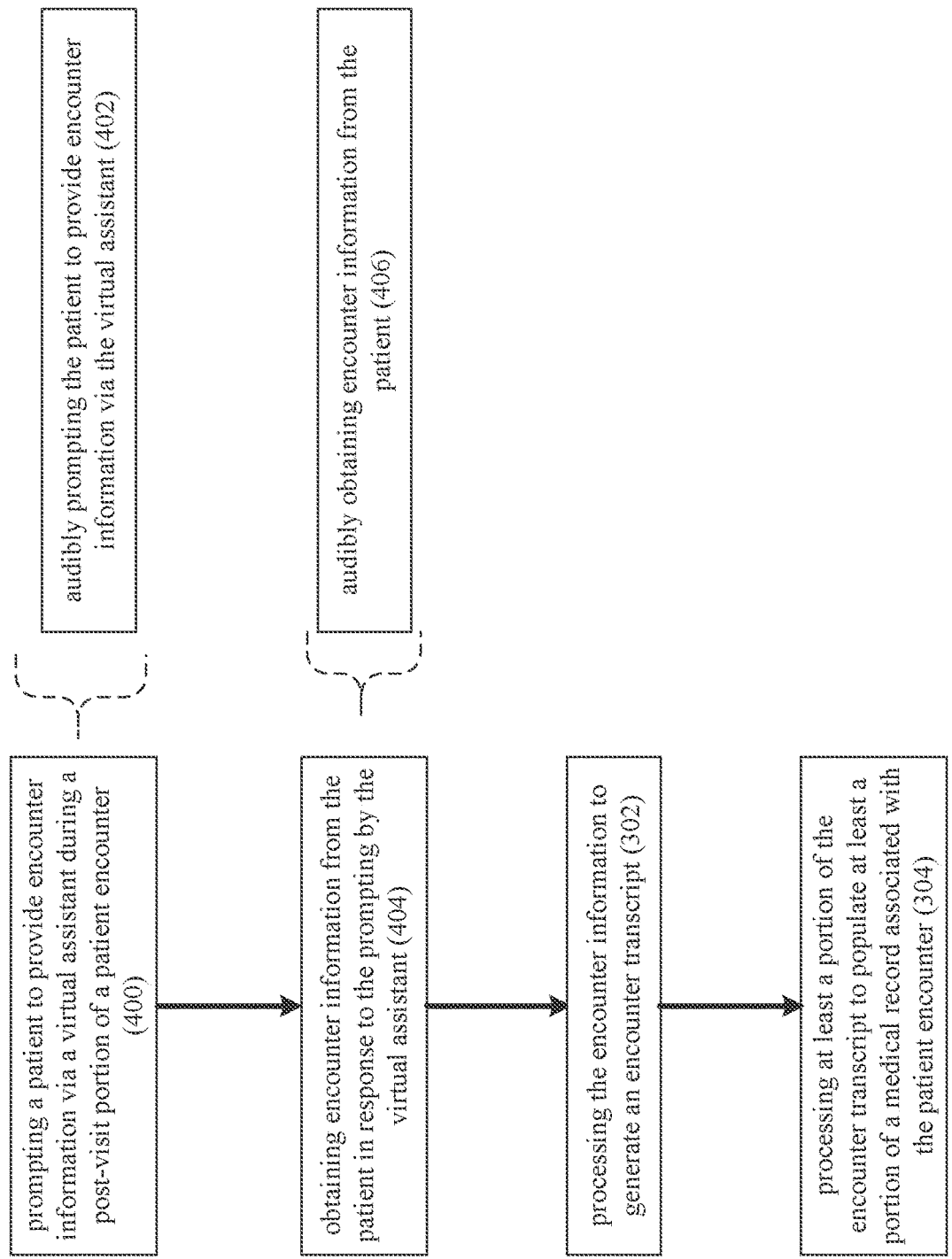
FIG. 6 is a flow chart of another implementation of the automated clinical documentation process of FIG. 1.

Accordingly and referring also to FIG. 6, automated clinical documentation process 10 may be configured to prompt 400 a patient (e.g., encounter participant 228) to provide encounter information (e.g., machine vision encounter information 102 and/or audio encounter information 106) via a virtual assistant (e.g., virtual assistant 238) during a post-visit portion of a patient encounter (e.g., encounter participant 228 visiting the doctor's office).

For example and upon completing the patient encounter (e.g., encounter participant 228 visiting the doctor's office), the patient (e.g., encounter participant 228) may be directed to a "check-out" area within the monitored space (e.g., monitored space 130) of the clinical environment. An example of this "check-out" area may include a booth into which the patient (e.g., encounter participant 228) enters. Upon entering this "check-out" area, the post-visit portion (e.g., the patient follow-up portion) of the patient encounter (e.g., encounter participant 228 visiting the doctor's office) may begin.

When prompting 400 the patient (e.g., encounter participant 228) to provide encounter information (e.g., machine vision encounter information 102 and/or audio encounter information 106) via the virtual assistant (e.g., virtual assistant 238), automated clinical documentation process 10 may audibly prompt 402 the patient (e.g., encounter participant 228) to provide encounter information (e.g., machine vision encounter information 102 and/or audio encounter information 106) via the virtual assistant (e.g., virtual assistant 238). For example, virtual assistant 238 may provide (via audio rendering device 116) a cordial greeting to the patient (e.g., encounter participant 228) and ask them if they are checking out. If the patient (e.g., encounter participant 228) responds affirmatively, virtual assistant 238 may audibly prompt 402 the patient (e.g., encounter participant 228) to provide encounter information (e.g., machine vision encounter information 102 and/or audio encounter information 106), examples of which may include but are not limited to: patient status information; patient medication information; and patient follow-up information.

Therefore, virtual assistant 238 may ask the patient (e.g., encounter participant 228) to provide various pieces of identifying information, examples of which may include but are not limited to: patient status information; patient medication information; and patient follow-up information, Depending upon the manner in which automated clinical documentation process 10 is configured, machine vision encounter information 102 may be utilized to further enhance/expedite the check-out process. For example and via machine vision encounter information 102, facial recognition functionality may be utilized to positively identify the patient (e.g., encounter participant 228). Additionally and via machine vision encounter information 102, visual speech recognition (via visual lip reading functionality) may be utilized by automated clinical documentation process 10 to further effectuate the gathering of audio encounter information 106.

While the post-visit portion of the patient encounter (e.g., encounter participant 228 visiting the doctor's office) is described above as being the point of the patient encounter (e.g., encounter participant 228 visiting the doctor's office) where the patient (e.g., encounter participant 228) is leaving the monitored space (e.g., monitored space 130) in a clinical environment, this is for illustrative purposes only and is not intended to be a limitation of this disclosure, as other configurations are possible and are considered to be within the scope of this disclosure. For example, this post-visit portion of the patient encounter (e.g., encounter participant 228 visiting the doctor's office) may include: automated wellness phone calls, automated wellness text messages, and automated wellness video conferences initiated by virtual assistant 238 and directed toward the patient (e.g., encounter participant 228) or a third party; and/or phone calls, text messages, and video conferences initiated by the patient (e.g., encounter participant 228) or a third party and automatically processed by virtual assistant 238.

During this post-visit portion (e.g., the patient follow-up portion) of the patient encounter (e.g., encounter participant 228 visiting the doctor's office), automated clinical documentation process 10 may obtain 404 encounter information (e.g., machine vision encounter information 102 and/or audio encounter information 106) from the patient (e.g., encounter participant 228) in response to the prompting by the virtual assistant (e.g., virtual assistant 238). When obtaining 404 encounter information (e.g., machine vision encounter information 102 and/or audio encounter information 106) from the patient (e.g., encounter participant 228), automated clinical documentation process 10 may audibly obtain 406 encounter information (e.g., machine vision encounter information 102 and/or audio encounter information 106) from the patient (e.g., encounter participant 228), thus allowing encounter participant 228 to simply verbalize their answers, wherein this information (e.g., audio encounter information 106) may be received via audio input device 30.

Automated clinical documentation process 10 may then process 302 the encounter information (e.g., machine vision encounter information 102 and/or audio encounter information 106) to generate an encounter transcript (e.g., encounter transcript 234), wherein at least a portion of the encounter transcript (e.g., encounter transcript 234) may be processed 304 to populate at least a portion of a medical record (e.g., medical record 236) associated with the patient encounter (e.g., a visit to a doctor's office).

Automated clinical documentation process 10 may be configured to monitor the interaction between the patient (e.g., encounter participant 228) and the medical professionals (e.g., a doctor, a nurse, a physician's assistant, a lab technician, a physical therapist and/or a staff member involved in the patient encounter) during the patient encounter (e.g., encounter participant 228 visiting the doctor's office) to determine if any potential medical situations are missed.

Figure 7:
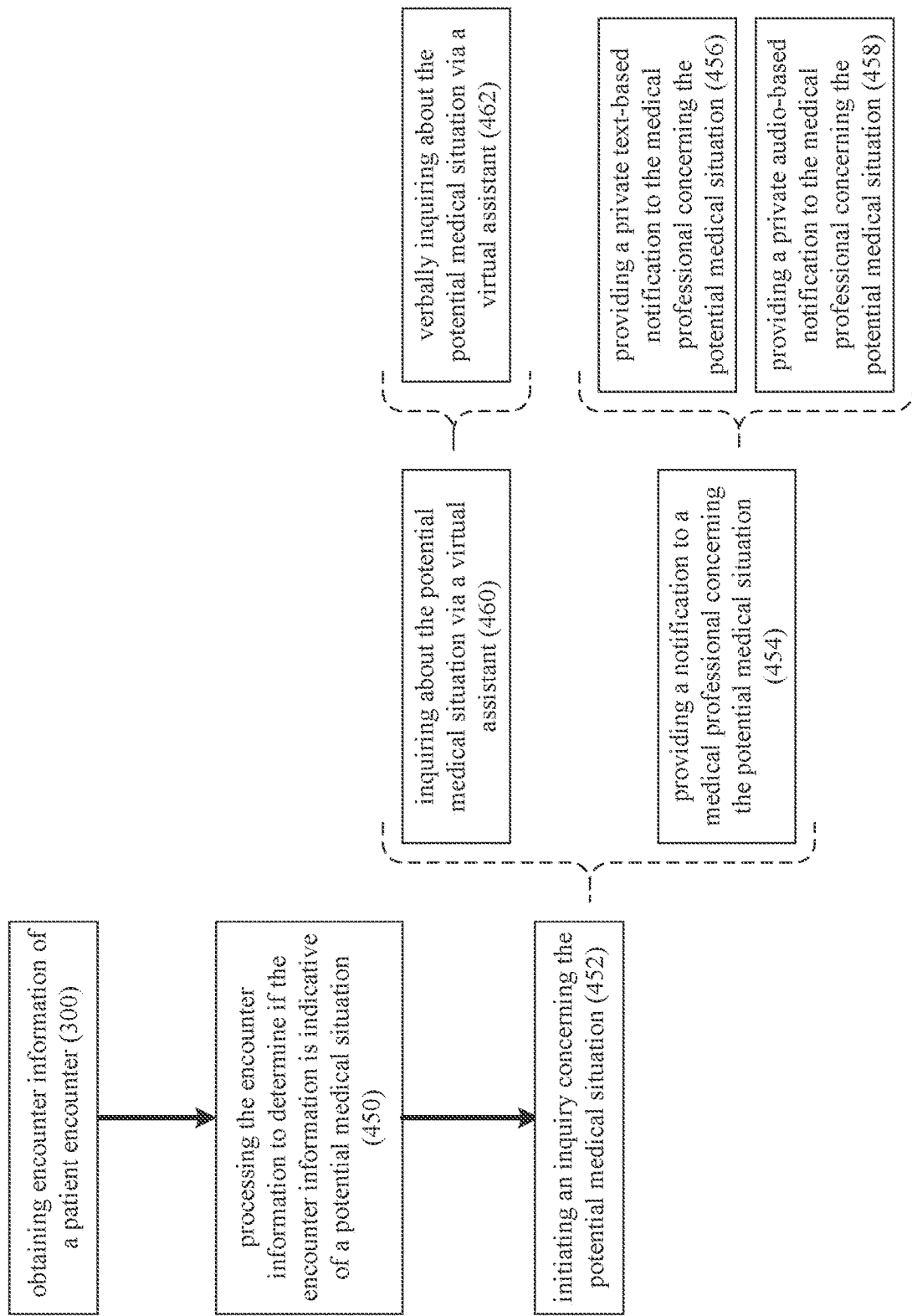
FIG. 7 is a flow chart of another implementation of the automated clinical documentation process of FIG. 1.

Accordingly and referring also to FIG. 7, automated clinical documentation process 10 may obtain 300 encounter information (e.g., machine vision encounter information 102 and/or audio encounter information 106) of a patient encounter (e.g., a visit to a doctor's office).

As discussed above, since machine vision system 100 and audio recording system 104 may be positioned throughout monitored space 130, all of the interactions between medical professionals (e.g., encounter participant 226), patients (e.g., encounter participant 228) and third parties (e.g., encounter participant 230) that occur during the patient encounter (e.g., encounter participant 228 visiting the doctor's office) within the monitored space (e.g., monitored space 130) of the clinical environment (e.g., the doctor's office) may be monitored/recorded/processed. Accordingly, a patient "check-in" area within monitored space 130 may be monitored to obtain encounter information (e.g., machine vision encounter information 102 and/or audio encounter information 106) during this pre-visit portion of the patient encounter (e.g., encounter participant 228 visiting the doctor's office). Additionally and as discussed above, this pre-visit encounter information may be obtained via e.g., virtual assistant 238 before the patient (e.g., encounter participant 228) has entered monitored space 130. Further, various rooms within monitored space 130 may be monitored to obtain encounter information (e.g., machine vision encounter information 102 and/or audio encounter information 106) during these various portions of the patient encounter (e.g., while meeting with the doctor, while vital signs and statistics are obtained, and while imaging is performed). Further, a patient "check-out" area within monitored space 130 may be monitored to obtain encounter information (e.g., machine vision encounter information 102 and/or audio encounter information 106) during this post-visit portion of the patient encounter (e.g., encounter participant 228 visiting the doctor's office). Additionally and as discussed above, this post-visit encounter information may be obtained via e.g., virtual assistant 238 after the patient (e.g., encounter participant 228) has left monitored space 130. Further and via machine vision encounter information 102, visual speech recognition (via visual lip reading functionality) may be utilized by automated clinical documentation process 10 to further effectuate the gathering of audio encounter information 106.

Accordingly, a complete recording of the patient encounter (e.g., encounter participant 228 visiting the doctor's office) may be generated, wherein this encounter information (e.g., machine vision encounter information 102 and/or audio encounter information 106) may be processed 302 to generate an encounter transcript (e.g., encounter transcript 234) and at least a portion of this encounter transcript (e.g., encounter transcript 234) may be processed 304 to populate at least a portion of a medical record (e.g., medical record 236) associated with the patient encounter (e.g., the visit to the doctor's office).

Automated clinical documentation process 10 may process 450 the encounter information (e.g., machine vision encounter information 102 and/or audio encounter information 106) to determine if the encounter information (e.g., machine vision encounter information 102 and/or audio encounter information 106) is indicative of a potential medical situation, wherein examples of these potential medical situations may include but are not limited to one or more of: a potential medical condition; a potential medication issue; a potential home healthcare issue; and a potential follow-up issue.

As discussed above, ACD compute system 12 may be configured to access one or more datasources (e.g., datasources 118), wherein examples of datasources 118 may include a medical conditions symptoms datasource (e.g., that defines the symptoms for various diseases and medical conditions), a prescriptions compatibility datasource (e.g., that defines groups of prescriptions that are substitutable for (or compatible with) each other), a medical insurance coverage datasource (e.g., that defines what prescriptions are covered by various medical insurance providers), and a home healthcare datasource (e.g., that defines best practices concerning when home healthcare is advisable). Accordingly, automated clinical documentation process 10 may process 450 the data included within the encounter information (e.g., machine vision encounter information 102 and/or audio encounter information 106) to compare this data to data defined within the datasources (e.g., datasources 118) to determine if the encounter information (e.g., machine vision encounter information 102 and/or audio encounter information 106) is indicative of a potential medical situation.

For example, assume that the encounter information (e.g., machine vision encounter information 102 and/or audio encounter information 106) indicates that the patient (e.g., encounter participant 228) mentioned during the patient encounter (e.g., encounter participant 228 visiting the doctor's office) that their wound was healing slowly. Can that be indicative of high blood sugar? Further suppose that the encounter information (e.g., machine vision encounter information 102 and/or audio encounter information 106) indicates that the patient (e.g., encounter participant 228) is quite elderly, lives alone and now needs to take injectable medication every day for the next week. Should home health care be arranged to medicate this patient? Additionally, suppose the encounter information (e.g., machine vision encounter information 102 and/or audio encounter information 106) indicates that the doctor (e.g., encounter participant 226) prescribed medication X. Does the patient's medical insurance cover Medication X (or do they only cover Medication Y)?

If a potential medical situation is identified, automated clinical documentation process 10 may initiate 452 an inquiry concerning the potential medical situation. When initiating 452 an inquiry concerning the potential medical situation, automated clinical documentation process 10 may provide 454 a notification (e.g., as visual information 110 and/or audio information 114) to a medical professional (e.g., a doctor, a nurse, a physician's assistant, a lab technician, a physical therapist and/or a staff member involved in the patient encounter) concerning the potential medical situation. Example of such an inquiry may be asking one or more questions, such as "Does this patient have diabetes?", "Should we arrange home healthcare for this patient?" of "Would you like to substitute Medication Y for Medication X?"

When providing 454 a notification (e.g., as visual information 110 and/or audio information 114) to a medical professional (e.g., a doctor, a nurse, a physician's assistant, a lab technician, a physical therapist and/or a staff member involved in the patient encounter) concerning the potential medical situation, automated clinical documentation process 10 may provide 456 a private text-based notification (e.g., as visual information 110) to the medical professional (e.g., a doctor, a nurse, a physician's assistant, a lab technician, a physical therapist and/or a staff member involved in the patient encounter) concerning the potential medical situation. This private text-based notification (e.g., as visual information 110) may be provided to the medical professional on e.g., a private display device, examples of which may include but are not limited to a smart phone, a table computer, a notebook computer, or a desktop computer.

When providing 454 a notification (e.g., as visual information 110 and/or audio information 114) to a medical professional (e.g., a doctor, a nurse, a physician's assistant, a lab technician, a physical therapist and/or a staff member involved in the patient encounter) concerning the potential medical situation, automated clinical documentation process 10 may provide 458 a private audio-based notification (e.g., as audio information 114) to the medical professional (e.g., a doctor, a nurse, a physician's assistant, a lab technician, a physical therapist and/or a staff member involved in the patient encounter) concerning the potential medical situation. This private audio-based notification (e.g., as audio information 114) may be provided to the medical professional on e.g., a private audio device, examples of which may include but are not limited to a smart phone, or an earbud.

Alternatively, when initiating 452 an inquiry concerning the potential medical situation, automated clinical documentation process 10 may inquire 460 about the potential medical situation via a virtual assistant (e.g., virtual assistant 238), wherein inquiring 460 about the potential medical situation via a virtual assistant (e.g., virtual assistant 238) may include verbally inquiring 462 about the potential medical situation via a virtual assistant (e.g., virtual assistant 238). For example and in such a configuration, when initiating 452 the inquiry, automated clinical documentation process 10 may inquire 460 about the potential medical situation by having virtual assistant 238 verbally (and publically) inquire 462 by asking one or more questions, such as "Does this patient have diabetes?", "Should we arrange home healthcare for this patient?" of "Would you like to substitute Medication Y for Medication X?"

Automated clinical documentation process 10 may be configured to simultaneously render content to multiple output devices at varying levels of detail, as it may be desirable to not broadcast certain "sensitive" content within the examination room.

Figure 8:
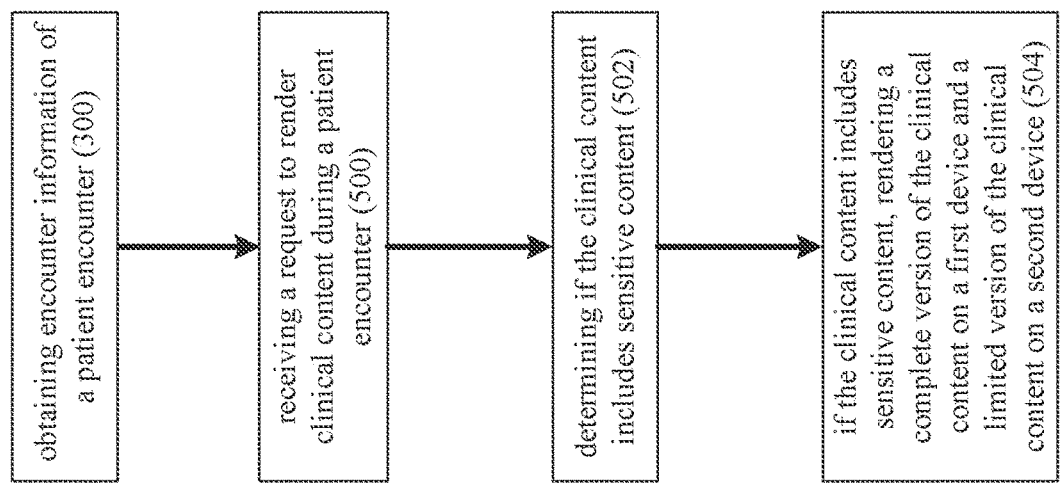
FIG. 8 is a flow chart of another implementation of the automated clinical documentation process of FIG. 1.

Accordingly and referring also to FIG. 8, automated clinical documentation process 10 may obtain 300 encounter information (e.g., machine vision encounter information 102 and/or audio encounter information 106) of a patient encounter (e.g., a visit to a doctor's office). Assume that during the course of the patient encounter (e.g., a visit to a doctor's office), a medical professional (e.g., a doctor, a nurse, a physician's assistant, a lab technician, a physical therapist and/or a staff member involved in the patient encounter) wishes to render a piece of content for viewing. For example and as discussed above, during the various portions of the patient encounter (e.g., a visit to a doctor's office), various procedures may occur, an example of which includes but is not limited to an imaging procedure. Accordingly, assume that the medical professional would like to display one or more images for viewing within the monitored space (e.g., monitored space 130). Accordingly, automated clinical documentation process 10 may be configured to receive 500 a request to render clinical content (e.g., an x-ray image) during a patient encounter (e.g., a visit to a doctor's office). This rendering request may be in the form of a verbal request (e.g., audio encounter information 106) that is spoken by e.g., a medical professional or a computer-based request that is initiated by the medical processional via ACD client electronic devices 28, 32.

Upon receiving 500 such a request, automated clinical documentation process 10 may determine 502 if the clinical content (e.g., the x-ray image) includes sensitive content. Examples of such sensitive content may include but are not limited to one or more of: sensitive image-based content; sensitive text-based content; sensitive prognosis-based content; sensitive diagnosis-based content; and sensitive complication-based content.

If the clinical content includes sensitive content, automated clinical documentation process 10 may render 504: a complete version of the clinical content (e.g., an x-ray image) on a first device (wherein the complete version of the clinical content includes the sensitive content) and a limited version of the clinical content (e.g., an x-ray image) on a second device (wherein the limited version of the clinical content excludes the sensitive content).

For this example, the first device may be a private device available only to one or more medical professionals of the patient encounter (e.g., a visit to a doctor's office). Examples of such private devices may include but are not limited to a visual private device and an audible private device. For this example, the second device may be a public device available to all encounter participants of the patient encounter (e.g., a visit to a doctor's office). Examples of such public devices may include but are not limited to a visual public device.

For example, assume that upon receiving 500 a request to render the clinical content (e.g., the x-ray image), automated clinical documentation process 10 determines 502 that the clinical content (e.g., the x-ray image) does include sensitive content (e.g., a strange mass). Accordingly, automated clinical documentation process 10 may render 504 a complete version of the x-ray image (that includes annotations highlighting the strange mass) on a first device e.g., a private tablet computer only accessible to the medical professional (e.g., a doctor, a nurse, a physician's assistant, a lab technician, a physical therapist and/or a staff member involved in the patient encounter). Further, automated clinical documentation process 10 may render 504 a limited version of the x-ray image (that excludes annotations highlighting the strange mass) on a second device (e.g., a wall-mounted television within monitored space 130).

As another example, automated clinical documentation process 10 may render 504 a complete version of the patient's symptoms on a second device (e.g., a wall-mounted television within monitored space 130), wherein some of these symptoms may be indicative of diabetes. Accordingly, automated clinical documentation process 10 may render 504 a private message as a text-based message or an audio-based message) on a first device (e.g., a private tablet computer accessible to the doctor or a private earbud worn by the doctor) indicating that some of these symptoms may be indicative of diabetes and, therefore, the doctor may wish to order an A1C test.

Automated clinical documentation process 10 may be configured to process the encounter information (e.g., machine vision encounter information 102 and/or audio encounter information 106) to generate encounter transcript 234 that may be automatically formatted and punctuated.

Figure 9:
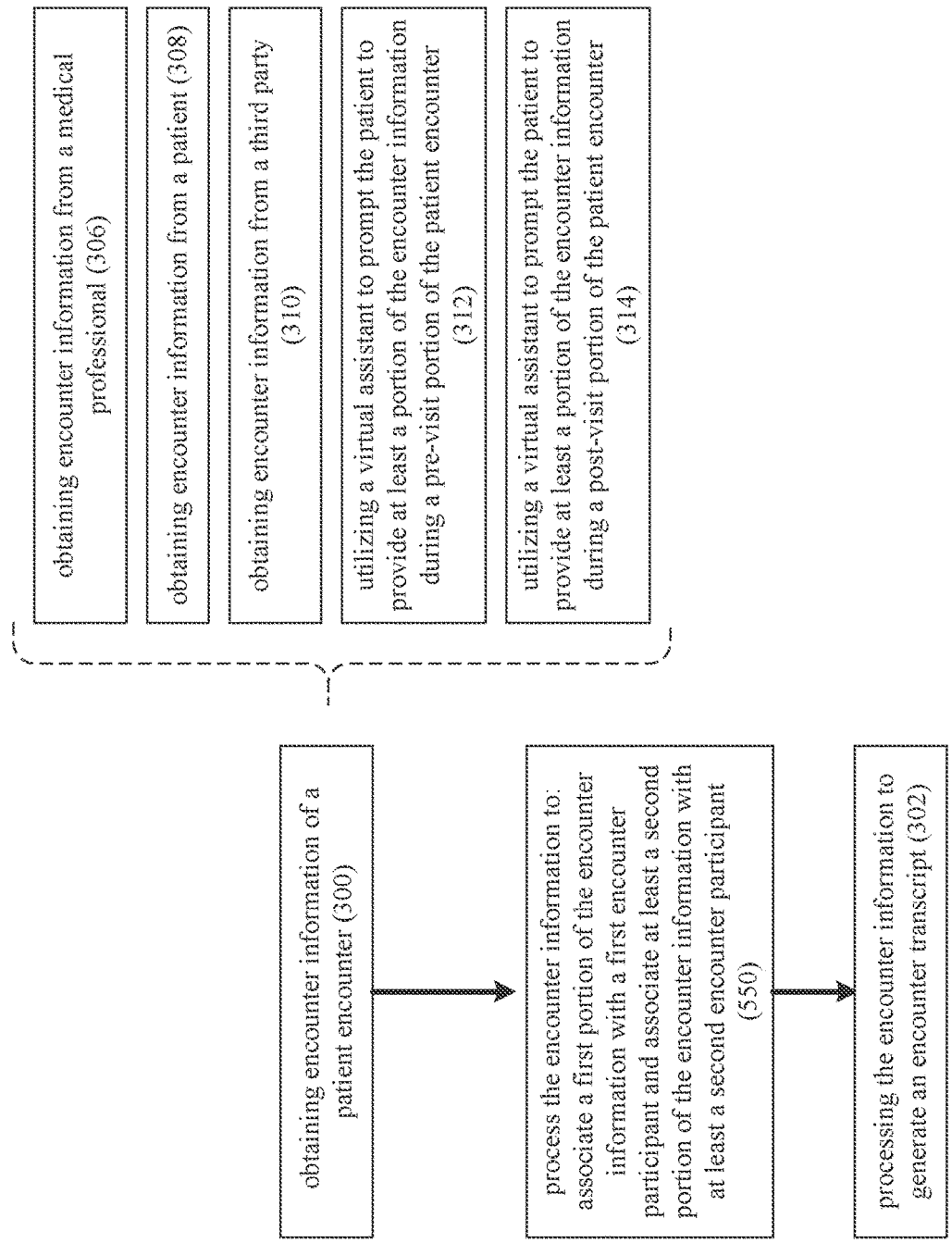
FIG. 9 is a flow chart of another implementation of the automated clinical documentation process of FIG. 1.

Accordingly and referring also to FIG. 9, automated clinical documentation process 10 may be configured to obtain 300 encounter information (e.g., machine vision encounter information 102 and/or audio encounter information 106) of a patient encounter (e.g., a visit to a doctor's office).

When obtaining 300 encounter information (e.g., machine vision encounter information 102 and/or audio encounter information 106), automated clinical documentation process 10 may obtain 306 the encounter information (e.g., machine vision encounter information 102 and/or audio encounter information 106) from a medical professional; obtain 308 the encounter information (e.g., machine vision encounter information 102 and/or audio encounter information 106) from a patient; and/or obtain 310 the encounter information (e.g., machine vision encounter information 102 and/or audio encounter information 106) from a third party. Further and when obtaining 300 encounter information (e.g., machine vision encounter information 102 and/or audio encounter information 106), automated clinical documentation process 10 may obtain 300 the encounter information (e.g., machine vision encounter information 102 and/or audio encounter information 106) from previous (related or unrelated) patient encounters. For example, if the current patient encounter is actually the third visit that the patient is making concerning e.g., shortness of breath, the encounter information from the previous two visits (i.e., the previous two patient encounters) may be highly-related and may be obtained 300 by automated clinical documentation process 10.

As discussed above, virtual assistant 238 may be configured to aid medical professionals (e.g., doctors, nurses, physician's assistants, lab technicians, physical therapists, scribes (e.g., a transcriptionist) and/or staff members involved in the patient encounter) with the gathering of encounter information (e.g., machine vision encounter information 102 and/or audio encounter information 106) during various portions of the patient encounter (e.g., encounter participant 228 visiting the doctor's office).

Accordingly and when obtaining 300 encounter information (e.g., machine vision encounter information 102 and/or audio encounter information 106), automated clinical documentation process 10 may utilize 312 a virtual assistant (e.g., virtual assistant 238) to prompt the patient to provide at least a portion of the encounter information (e.g., machine vision encounter information 102 and/or audio encounter information 106) during a pre-visit portion of the patient encounter (e.g., a visit to a doctor's office).

Further and when obtaining 300 encounter information (e.g., machine vision encounter information 102 and/or audio encounter information 106), automated clinical documentation process 10 may utilize 314 a virtual assistant (e.g., virtual assistant 238) to prompt the patient to provide at least a portion of the encounter information (e.g., machine vision encounter information 102 and/or audio encounter information 106) during a post-visit portion of the patient encounter (e.g., a visit to a doctor's office).

Automated clinical documentation process 10 may process 550 the encounter information (e.g., machine vision encounter information 102 and/or audio encounter information 106) to: associate a first portion of the encounter information (e.g., machine vision encounter information 102 and/or audio encounter information 106) with a first encounter participant, and associate at least a second portion of the encounter information (e.g., machine vision encounter information 102 and/or audio encounter information 106) with at least a second encounter participant.

As discussed above, modular ACD system 54 may be configured to form one or more audio recording beams (e.g., audio recording beams 220, 222, 224) via the discrete audio acquisition devices (e.g., discrete audio acquisition devices 202, 204, 206, 208, 210, 212, 214, 216, 218) included within audio recording system 104, wherein modular ACD system 54 may be further configured to steer the one or more audio recording beams (e.g., audio recording beams 220, 222, 224) toward one or more encounter participants (e.g., encounter participants 226, 228, 230) of the above-described patient encounter.

Accordingly and continuing with the above-stated example, modular ACD system 54 may steer audio recording beam 220 toward encounter participant 226, may steer audio recording beam 222 toward encounter participant 228, and may steer audio recording beam 224 toward encounter participant 230. Accordingly and due to the directionality of audio recording beams 220, 222, 224, audio encounter information 106 may include three components, namely audio encounter information 106A (which is obtained via audio recording beam 220), audio encounter information 106B (which is obtained via audio recording beam 222) and audio encounter information 106C (which is obtained via audio recording beam 220).

Further and as discussed above, ACD compute system 12 may be configured to access one or more datasources 118 (e.g., plurality of individual datasources 120, 122, 124, 126, 128), examples of which may include but are not limited to one or more of a user profile datasource, a voice print datasource, a voice characteristics datasource (e.g., for adapting the automated speech recognition models), a face print datasource, a humanoid shape datasource, an utterance identifier datasource, a wearable token identifier datasource, an interaction identifier datasource, a medical conditions symptoms datasource, a prescriptions compatibility datasource, a medical insurance coverage datasource, and a home healthcare datasource.

Accordingly, automated clinical documentation process 10 may process 550 the encounter information (e.g., machine vision encounter information 102 and/or audio encounter information 106) to: associate a first portion (e.g., encounter information 106A) of the encounter information (e.g., audio encounter information 106) with a first encounter participant (e.g., encounter participant 226), and associate at least a second portion (e.g., encounter information 106B, 106C) of the encounter information (e.g., audio encounter information 106) with at least a second encounter participant (e.g., encounter participants 228, 230; respectively).

Further and when processing 550 the encounter information (e.g., audio encounter information 106A, 106B, 106C), automated clinical documentation process 10 may compare each of audio encounter information 106A, 106B, 106C to the voice prints defined within the above-referenced voice print datasource so that the identity of encounter participants 226, 228, 230 (respectively) may be determined. Accordingly, if the voice print datasource includes a voice print that corresponds to one or more of the voice of encounter participant 226 (as heard within audio encounter information 106A), the voice of encounter participant 228 (as heard within audio encounter information 106B) or the voice of encounter participant 230 (as heard within audio encounter information 106C), the identity of one or more of encounter participants 226, 228, 230 may be defined. And in the event that a voice heard within one or more of audio encounter information 106A, audio encounter information 106B or audio encounter information 106C is unidentifiable, that one or more particular encounter participant may be defined as "Unknown Participant".

Once the voices of encounter participants 226, 228, 230 are processed 550, automated clinical documentation process 10 may generate 302 an encounter transcript (e.g., encounter transcript 234) based, at least in part, upon the first portion of the encounter information (e.g., audio encounter information 106A) and the at least a second portion of the encounter information (e.g., audio encounter information 106B. 106C).

Automated clinical documentation process 10 may be configured to automatically define roles for the encounter participants (e.g., encounter participants 226, 228, 230) in the patient encounter (e.g., a visit to a doctor's office).

Figure 10:
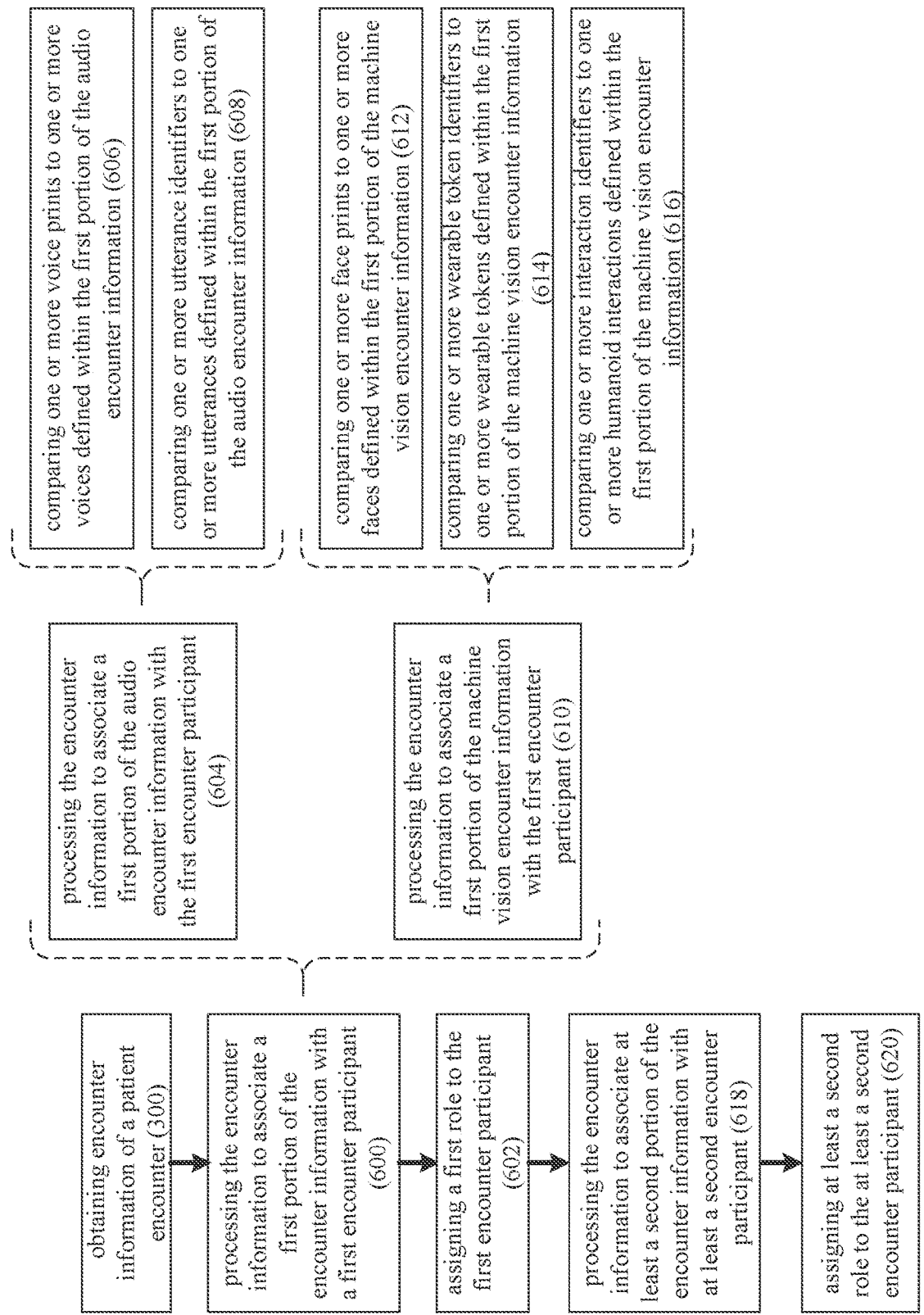
FIG. 10 is a flow chart of another implementation of the automated clinical documentation process of FIG. 1.

Accordingly and referring also to FIG. 10, automated clinical documentation process 10 may be configured to obtain 300 encounter information (e.g., machine vision encounter information 102 and/or audio encounter information 106) of a patient encounter (e.g., a visit to a doctor's office).

Automated clinical documentation process 10 may then process 600 the encounter information (e.g., machine vision encounter information 102 and/or audio encounter information 106) to associate a first portion of the encounter information with a first encounter participant (e.g., encounter participant 226) and assign 602 a first role to the first encounter participant (e.g., encounter participant 226).

When processing 600 the encounter information (e.g., machine vision encounter information 102 and/or audio encounter information 106) to associate the first portion of the encounter information with the first encounter participant (e.g., encounter participant 226), automated clinical documentation process 10 may process 604 the encounter information (e.g., machine vision encounter information 102 and/or audio encounter information 106) to associate a first portion of the audio encounter information (e.g., audio encounter information 106A) with the first encounter participant (e.g., encounter participant 226).

Specifically and when processing 604 the encounter information (e.g., machine vision encounter information 102 and/or audio encounter information 106) to associate the first portion of the audio encounter information (e.g., audio encounter information 106A) with the first encounter participant (e.g., encounter participant 226), automated clinical documentation process 10 may compare 606 one or more voice prints (defined within voice print datasource) to one or more voices defined within the first portion of the audio encounter information (e.g., audio encounter information 106A); and may compare 608 one or more utterance identifiers (defined within utterance datasource) to one or more utterances defined within the first portion of the audio encounter information (e.g., audio encounter information 106A); wherein comparisons 606, 608 may allow automated clinical documentation process 10 to assign 602 a first role to the first encounter participant (e.g., encounter participant 226). For example, if the identity of encounter participant 226 can be defined via voice prints, a role for encounter participant 226 may be assigned 602 if that identity defined is associated with a role (e.g., the identity defined for encounter participant 226 is Doctor Susan Jones). Further, if an utterance made by encounter participant 226 is "I am Doctor Susan Jones", this utterance may allow a role for encounter participant 226 to be assigned 602.

When processing 600 the encounter information (e.g., machine vision encounter information 102 and/or audio encounter information 106) to associate the first portion of the encounter information with the first encounter participant (e.g., encounter participant 226), automated clinical documentation process 10 may process 610 the encounter information (e.g., machine vision encounter information 102 and/or audio encounter information 106) to associate a first portion of the machine vision encounter information (e.g., machine vision encounter information 102A) with the first encounter participant (e.g., encounter participant 226).

Specifically and when processing 610 the encounter information (e.g., machine vision encounter information 102 and/or audio encounter information 106) to associate the first portion of the machine vision encounter information (e.g., machine vision encounter information 102A) with the first encounter participant (e.g., encounter participant 226), automated clinical documentation process 10 may compare 612 one or more face prints (defined within face print datasource) to one or more faces defined within the first portion of the machine vision encounter information (e.g., machine vision encounter information 102A); compare 614 one or more wearable token identifiers (defined within wearable token identifier datasource) to one or more wearable tokens defined within the first portion of the machine vision encounter information (e.g., machine vision encounter information 102A); and compare 616 one or more interaction identifiers (defined within interaction identifier datasource) to one or more humanoid interactions defined within the first portion of the machine vision encounter information (e.g., machine vision encounter information 102A); wherein comparisons 612, 614, 616 may allow automated clinical documentation process 10 to assign 602 a first role to the first encounter participant (e.g., encounter participant 226). For example, if the identity of encounter participant 226 can be defined via face prints, a role for encounter participant 226 may be assigned 602 if that identity defined is associated with a role (e.g., the identity defined for encounter participant 226 is Doctor Susan Jones). Further, if a wearable token worn by encounter participant 226 can be identified as a wearable token assigned to Doctor Susan Jones, a role for encounter participant 226 may be assigned 602. Additionally, if an interaction made by encounter participant 226 corresponds to the type of interaction that is made by a doctor, the existence of this interaction may allow a role for encounter participant 226 to be assigned 602.

Examples of such wearable tokens may include but are not limited to wearable devices that may be worn by the medical professionals when they are within monitored space 130 (or after they leave monitored space 130). For example, these wearable tokens may be worn by medical professionals when e.g., they are moving between monitored rooms within monitored space 130, travelling to and/or from monitored space 130, and/or outside of monitored space 130 (e.g., at home).

Additionally, automated clinical documentation process 10 may process 618 the encounter information (e.g., machine vision encounter information 102 and/or audio encounter information 106) to associate at least a second portion of the encounter information with at least a second encounter participant; and may assign 620 at least a second role to the at least a second encounter participant.

Specifically, automated clinical documentation process 10 may process 618 the encounter information (e.g., machine vision encounter information 102 and/or audio encounter information 106) to associate at least a second portion of the encounter information with at least a second encounter participant. For example, automated clinical documentation process 10 may process 618 the encounter information (e.g., machine vision encounter information 102 and/or audio encounter information 106) to associate audio encounter information 106B and machine vision encounter information 102B with encounter participant 228 and may associate audio encounter information 106C and machine vision encounter information 102C with encounter participant 230.

Further, automated clinical documentation process 10 may assign 620 at least a second role to the at least a second encounter participant. For example, automated clinical documentation process 10 may assign 620 a role to encounter participants 228, 230.

Automated clinical documentation process 10 may be configured to monitor multiple encounter participants (e.g., encounter participants 226, 228, 230) within a patient encounter (e.g., a visit to a doctor's office), wherein some of these encounter participants may be identifiable via a unique voice print profile, while others may be unidentifiable due to a lack of a unique voice print profile.

Figure 11:
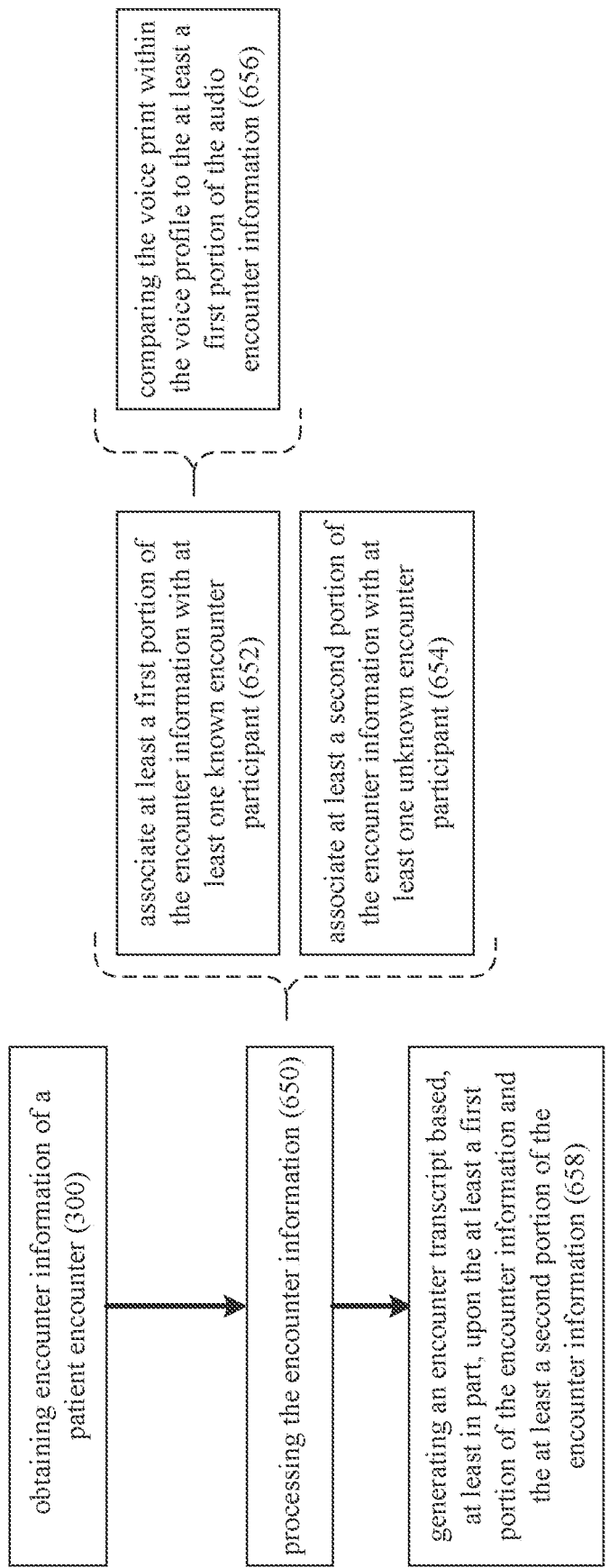
FIG. 11 is a flow chart of another implementation of the automated clinical documentation process of FIG. 1.

Accordingly and referring also to FIG. 11, automated clinical documentation process 10 may be configured to obtain 300 encounter information (e.g., machine vision encounter information 102 and/or audio encounter information 106) of a patient encounter (e.g., a visit to a doctor's office).

Automated clinical documentation process 10 may process 650 the encounter information (e.g., machine vision encounter information 102 and/or audio encounter information 106) to: associate 652 at least a first portion of the encounter information (e.g., machine vision encounter information 102 and/or audio encounter information 106) with at least one known encounter participant, and associate 654 at least a second portion of the encounter information (e.g., machine vision encounter information 102 and/or audio encounter information 106) with at least one unknown encounter participant.

As discussed above, modular ACD system 54 may be configured to form one or more audio recording beams (e.g., audio recording beams 220, 222, 224) via the discrete audio acquisition devices (e.g., discrete audio acquisition devices 202, 204, 206, 208, 210, 212, 214, 216, 218) included within audio recording system 104, wherein modular ACD system 54 may be further configured to steer the one or more audio recording beams (e.g., audio recording beams 220, 222, 224) toward one or more encounter participants (e.g., encounter participants 226, 228, 230) of the above-described patient encounter.

Accordingly and continuing with the above-stated example, modular ACD system 54 may steer audio recording beam 220 toward encounter participant 226, may steer audio recording beam 222 toward encounter participant 228, and may steer audio recording beam 224 toward encounter participant 230. Accordingly and due to the directionality of audio recording beams 220, 222, 224, audio encounter information 106 may include three components, namely audio encounter information 106A (which is obtained via audio recording beam 220), audio encounter information 106B (which is obtained via audio recording beam 222) and audio encounter information 106C (which is obtained via audio recording beam 220).

Further and as discussed above, ACD compute system 12 may be configured to access one or more datasources 118 (e.g., plurality of individual datasources 120, 122, 124, 126, 128), examples of which may include but are not limited to one or more of a user profile datasource, a voice print datasource, a voice characteristics datasource (e.g., for adapting the automated speech recognition models), a face print datasource, a humanoid shape datasource, an utterance identifier datasource, a wearable token identifier datasource, an interaction identifier datasource, a medical conditions symptoms datasource, a prescriptions compatibility datasource, a medical insurance coverage datasource, and a home healthcare datasource.

When associating 652 at least a first portion of the encounter information (e.g., machine vision encounter information 102 and/or audio encounter information 106) with at least one known encounter participant, automated clinical documentation process 10 may compare 656 the data included within the user profile (defined within the user profile datasource) to the at least a first portion of the audio encounter information. The data included within the user profile may include voice-related data (e.g., a voice print that is defined locally within the user profile or remotely within the voice print datasource), language use patterns, user accent identifiers, user-defined macros, and user-defined shortcuts, for example.

Specifically and when attempting to associate 652 at least a first portion of the encounter information (e.g., machine vision encounter information 102 and/or audio encounter information 106) with at least one known encounter participant, automated clinical documentation process 10 may compare 656 one or more voice prints (defined within the voice print datasource) to one or more voices defined within the first portion of the audio encounter information (e.g., audio encounter information 106A); may compare 656 one or more voice prints (defined within the voice print datasource) to one or more voices defined within the second portion of the audio encounter information (e.g., audio encounter information 106B); and may compare 656 one or more voice prints (defined within the voice print datasource) to one or more voices defined within the third portion of the audio encounter information (e.g., audio encounter information 106C).

As discussed above and for this example, assume: that encounter participant 226 is a medical professional that has a voice print/profile; that encounter participant 228 is a long-term patient that has a voice print/profile; and that encounter participant 230 is a third party (the acquaintance of encounter participant 228) and, therefore, does not have a voice print/profile. Accordingly and for this example: assume that automated clinical documentation process 10 will be successful and identify encounter participant 226 when comparing 656 audio encounter information 106A to the various voice prints/profiles included within voice print datasource; assume that automated clinical documentation process 10 will be successful and identify encounter participant 228 when comparing 656 audio encounter information 106B to the various voice prints/profiles included within voice print datasource; and assume that automated clinical documentation process 10 will be unsuccessful and not identify encounter participant 230 when comparing 656 audio encounter information 106C to the various voice prints/profiles included within voice print datasource.

Accordingly and when processing 650 the encounter information (e.g., machine vision encounter information 102 and/or audio encounter information 106), automated clinical documentation process 10 may associate 652 audio encounter information 106A with the voice print/profile of Doctor Susan Jones and may identify encounter participant 226 as "Doctor Susan Jones". Automated clinical documentation process 10 may further associate 654 audio encounter information 106B with the voice print/profile of Patient Paul Smith and may identify encounter participant 228 as "Patient Paul Smith". Further, automated clinical documentation process 10 may not be able to associate 654 audio encounter information 106C with any voice prints/profiles and may identify encounter participant 230 as "Unknown Participant".

Automated clinical documentation process 10 may generate 658 an encounter transcript (e.g., encounter transcript 234) based, at least in part, upon the at least a first portion of the encounter information (e.g., machine vision encounter information 102 and/or audio encounter information 106) and the at least a second portion of the encounter information (e.g., machine vision encounter information 102 and/or audio encounter information 106). Accordingly, automated clinical documentation process 10 may generate 658 an encounter transcript (e.g., encounter transcript 234) that identifies the verbal comments and utterances made by "Doctor Susan Jones", "Patient Paul Smith" and "Unknown Participant".

Automated clinical documentation process 10 may be configured to use semantic frames as an intermediary step between encounter transcript 234 and medical record 236, wherein these semantic frames may define an abstract meaning of a portion of encounter transcript and this abstract meaning may be used when populating medical record 236.

Figure 12:
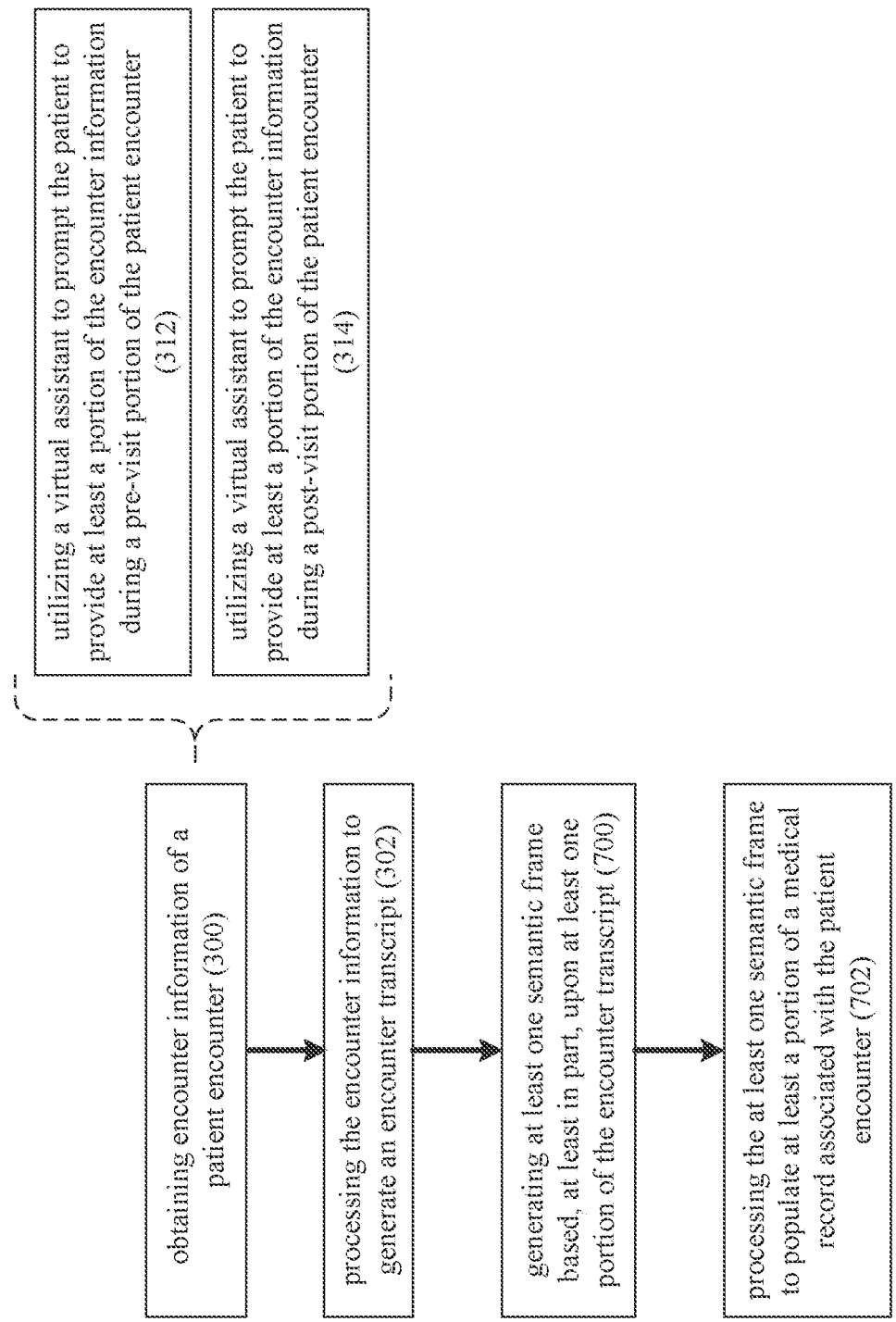
FIG. 12 is a flow chart of another implementation of the automated clinical documentation process of FIG. 1.
Figure 13B:
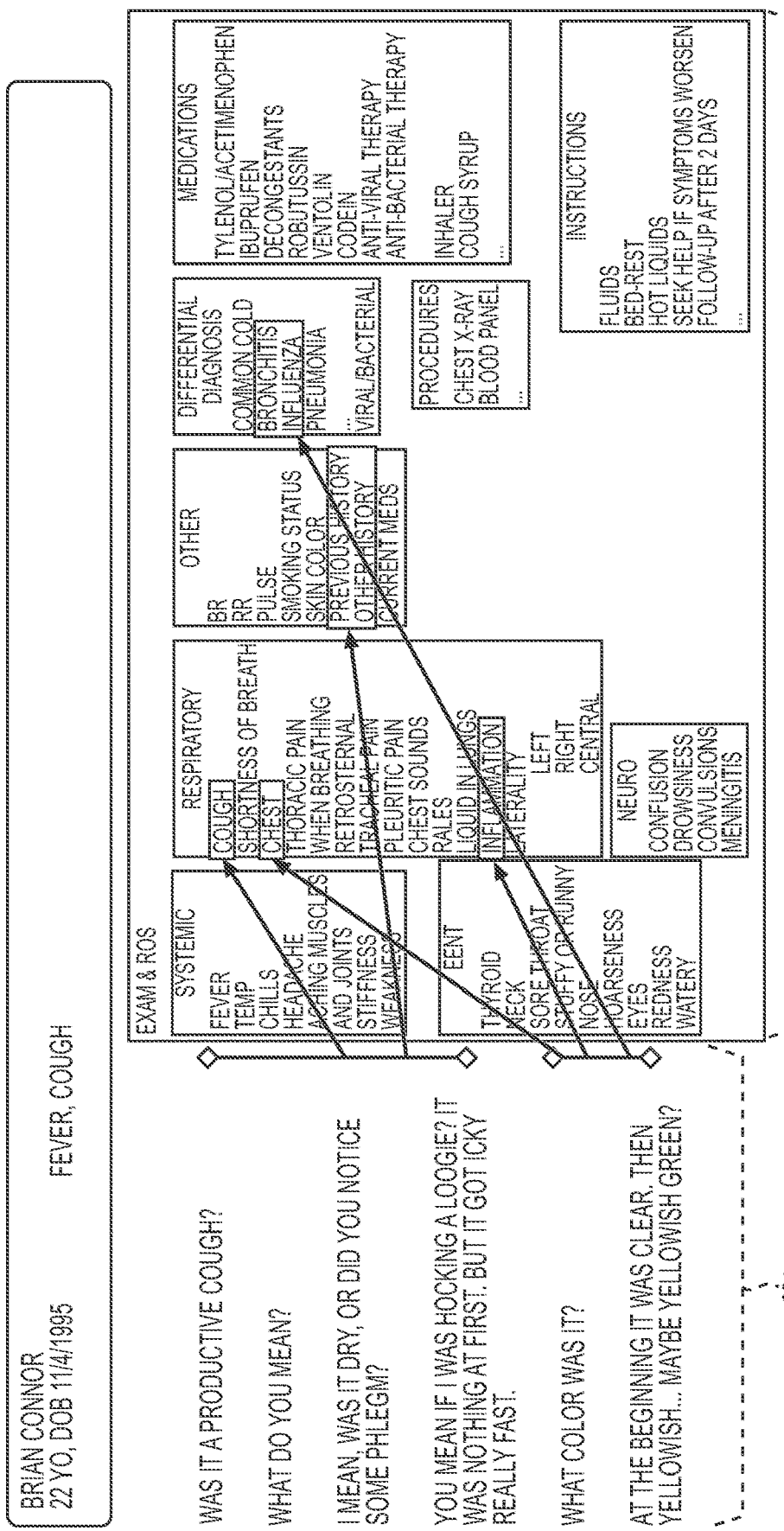
Figure 13C:
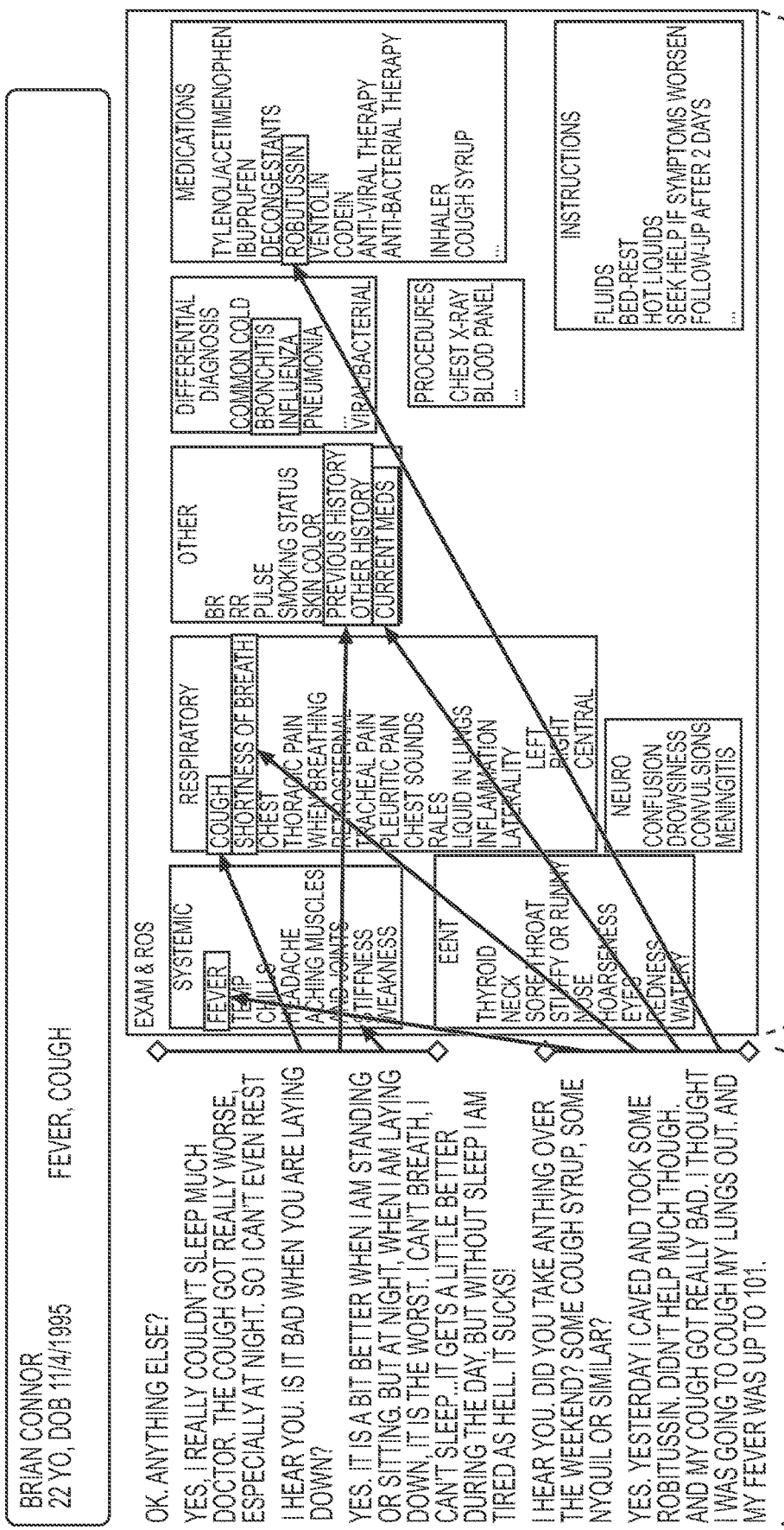
Figure 13D:
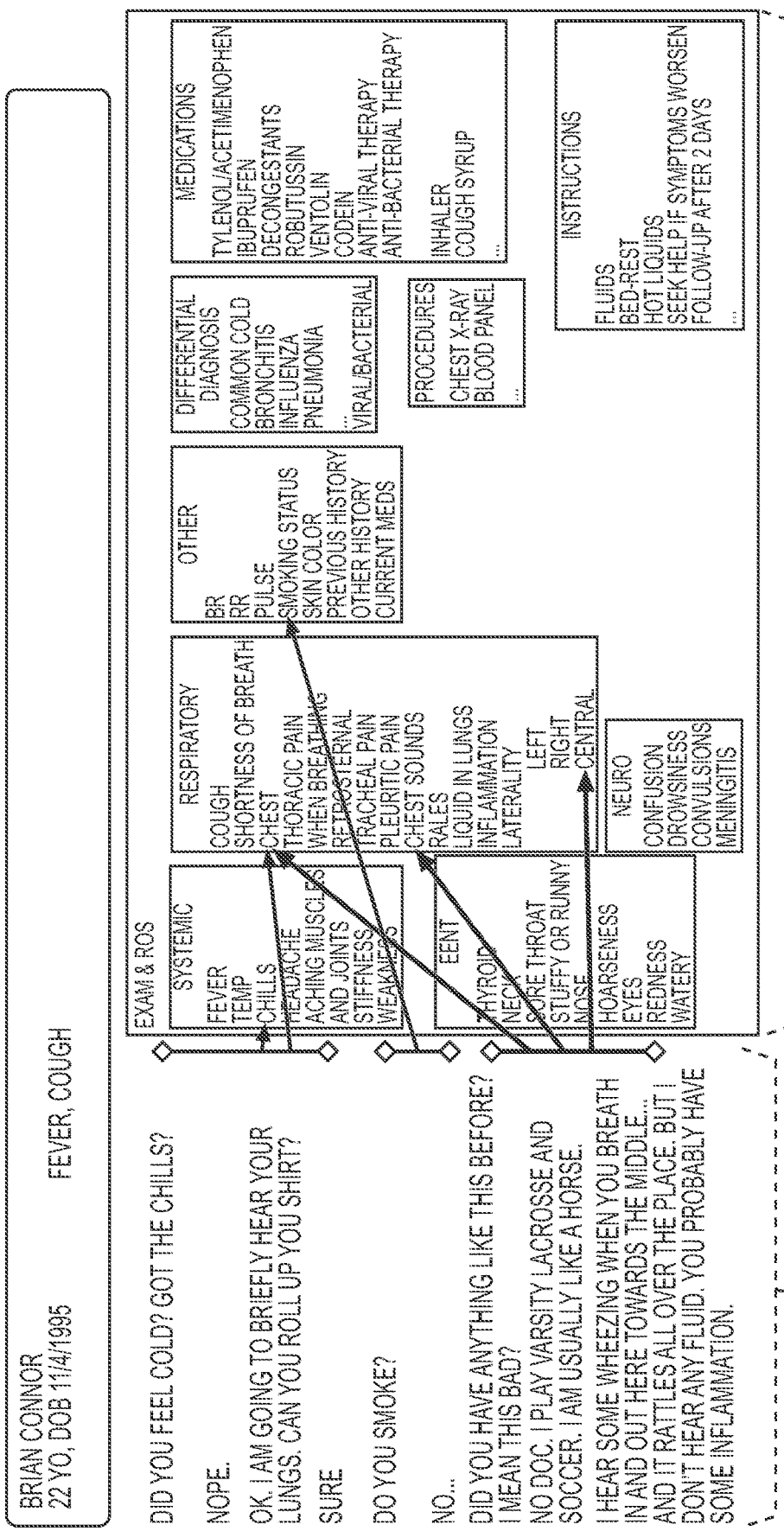
Figure 13E:
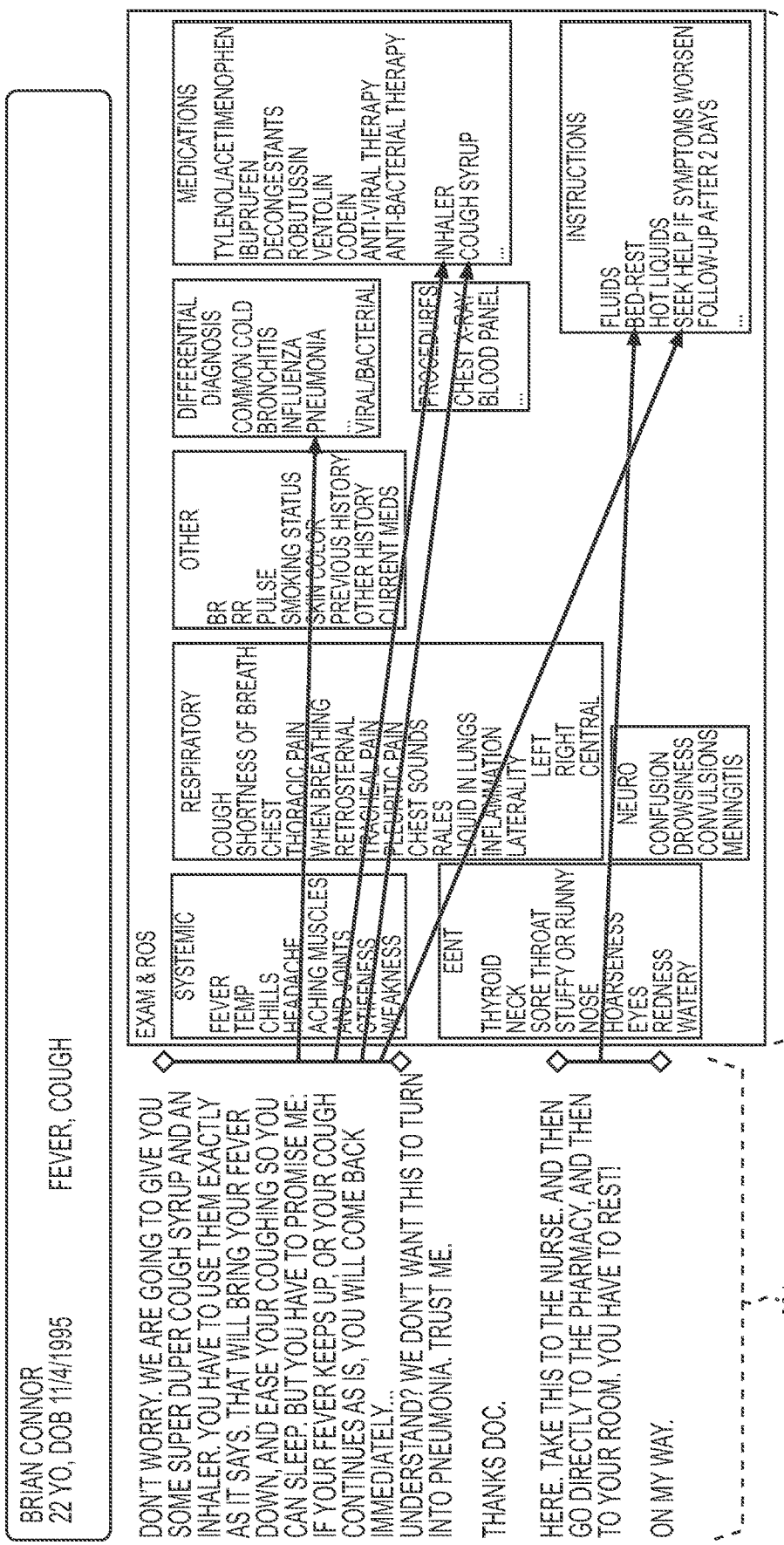

Accordingly and referring also to FIG. 12, automated clinical documentation process 10 may be configured to obtain 300 encounter information (e.g., machine vision encounter information 102 and/or audio encounter information 106) of a patient encounter (e.g., a visit to a doctor's office).

As discussed above, since machine vision system 100 and audio recording system 104 may be positioned throughout monitored space 130, all of the interactions between medical professionals (e.g., encounter participant 226), patients (e.g., encounter participant 228) and third parties (e.g., encounter participant 230) that occur during the patient encounter (e.g., encounter participant 228 visiting the doctor's office) within the monitored space (e.g., monitored space 130) of the clinical environment (e.g., the doctor's office) may be monitored/recorded/processed. Accordingly, a patient "check-in" area within monitored space 130 may be monitored to obtain encounter information (e.g., machine vision encounter information 102 and/or audio encounter information 106) during this pre-visit portion of the patient encounter (e.g., encounter participant 228 visiting the doctor's office). Additionally and as discussed above, this pre-visit encounter information may be obtained via e.g., virtual assistant 238 before the patient (e.g., encounter participant 228) has entered monitored space 130. Further, various rooms within monitored space 130 may be monitored to obtain encounter information (e.g., machine vision encounter information 102 and/or audio encounter information 106) during these various portions of the patient encounter (e.g., while meeting with the doctor, while vital signs and statistics are obtained, and while imaging is performed). Further, a patient "check-out" area within monitored space 130 may be monitored to obtain encounter information (e.g., machine vision encounter information 102 and/or audio encounter information 106) during this post-visit portion of the patient encounter (e.g., encounter participant 228 visiting the doctor's office). Additionally and as discussed above, this post-visit encounter information may be obtained via e.g., virtual assistant 238 after the patient (e.g., encounter participant 228) has left monitored space 130. Further and via machine vision encounter information 102, visual speech recognition (via visual lip reading functionality) may be utilized by automated clinical documentation process 10 to further effectuate the gathering of audio encounter information 106.

Accordingly, a complete recording of the patient encounter (e.g., encounter participant 228 visiting the doctor's office) may be generated, wherein this encounter information (e.g., machine vision encounter information 102 and/or audio encounter information 106) may be processed 302 to generate an encounter transcript (e.g., encounter transcript 234).

As is known in the art, a semantic frame (e.g., semantic frame 240) may be a collection of facts that specify "characteristic features, attributes, and functions of a denotatum, and its characteristic interactions with things necessarily or typically associated with it." Accordingly, a semantic frame (e.g., semantic frame 240) may be defined as a coherent structure of related concepts that are related such that without knowledge of all of the related concepts, one does not have complete knowledge of any of the related concepts. Further, a semantic frame (e.g., semantic frame 240) may be based on recurring experiences, wherein e.g., a commercial transaction semantic frame may be based upon recurring experiences in the commercial transactions space. Accordingly, a semantic frame (e.g., semantic frame 240) may define an abstract meaning of a portion of an encounter transcript.

Accordingly, automated clinical documentation process 10 may generate 700 at least one semantic frame (e.g., semantic frame 240) based, at least in part, upon at least one portion of encounter transcript 234, wherein the at least one semantic frame (e.g., semantic frame 240) may define an abstract meaning for the at least one portion of encounter transcript 234.

Referring also to FIGS. 13A-13E, there are shown various illustrative examples concerning the manner in which automated clinical documentation process 10 may generate 700 at least one semantic frame (e.g., semantic frame 240) based, at least in part, upon at least one portion of encounter transcript 234, Specifically and as shown in these figures, various discrete portions of encounter transcript 234 may be mapped onto the various semantic frames.

Automated clinical documentation process 10 may then process 702 the at least one semantic frame (e.g., semantic frame 240) to populate at least a portion of a medical record (e.g., medical record 236) associated with the patient encounter (e.g., a visit to a doctor's office).

Referring also to FIGS. 14A-14B, there are shown various illustrative examples concerning the manner in which automated clinical documentation process 10 may process 702 the at least one semantic frame (e.g., semantic frame 240) to populate at least a portion of a medical record (e.g., medical record 236). Specifically and as shown in these figures, various discrete pieces of data defined within the various semantic frames (e.g., semantic frame 240) may be used to populate medical record 236.

As discussed above, virtual assistant 238 may be configured to aid medical professionals (e.g., doctors, nurses, physician's assistants, lab technicians, physical therapists, scribes (e.g., a transcriptionist) and/or staff members involved in the patient encounter) with the gathering of encounter information (e.g., machine vision encounter information 102 and/or audio encounter information 106) during various portions of the patient encounter (e.g., encounter participant 228 visiting the doctor's office).

Accordingly and when obtaining 300 encounter information (e.g., machine vision encounter information 102 and/or audio encounter information 106), automated clinical documentation process 10 may utilize 312 a virtual assistant (e.g., virtual assistant 238) to prompt the patient to provide at least a portion of the encounter information (e.g., machine vision encounter information 102 and/or audio encounter information 106) during a pre-visit portion of the patient encounter (e.g., a visit to a doctor's office).

Further and when obtaining 300 encounter information (e.g., machine vision encounter information 102 and/or audio encounter information 106), automated clinical documentation process 10 may utilize 314 a virtual assistant (e.g., virtual assistant 238) to prompt the patient to provide at least a portion of the encounter information (e.g., machine vision encounter information 102 and/or audio encounter information 106) during a post-visit portion of the patient encounter (e.g., a visit to a doctor's office).

Automated clinical documentation process 10 may be configured to track the movement and/or interaction of humanoid shapes within the monitored space (e.g., monitored space 130) during the patient encounter (e.g., a visit to a doctor's office) so that e.g., the automated clinical documentation process 10 knows when encounter participants (e.g., one or more of encounter participants 226, 228, 230) enter, exit or cross paths within monitored space 130.

Figure 15:
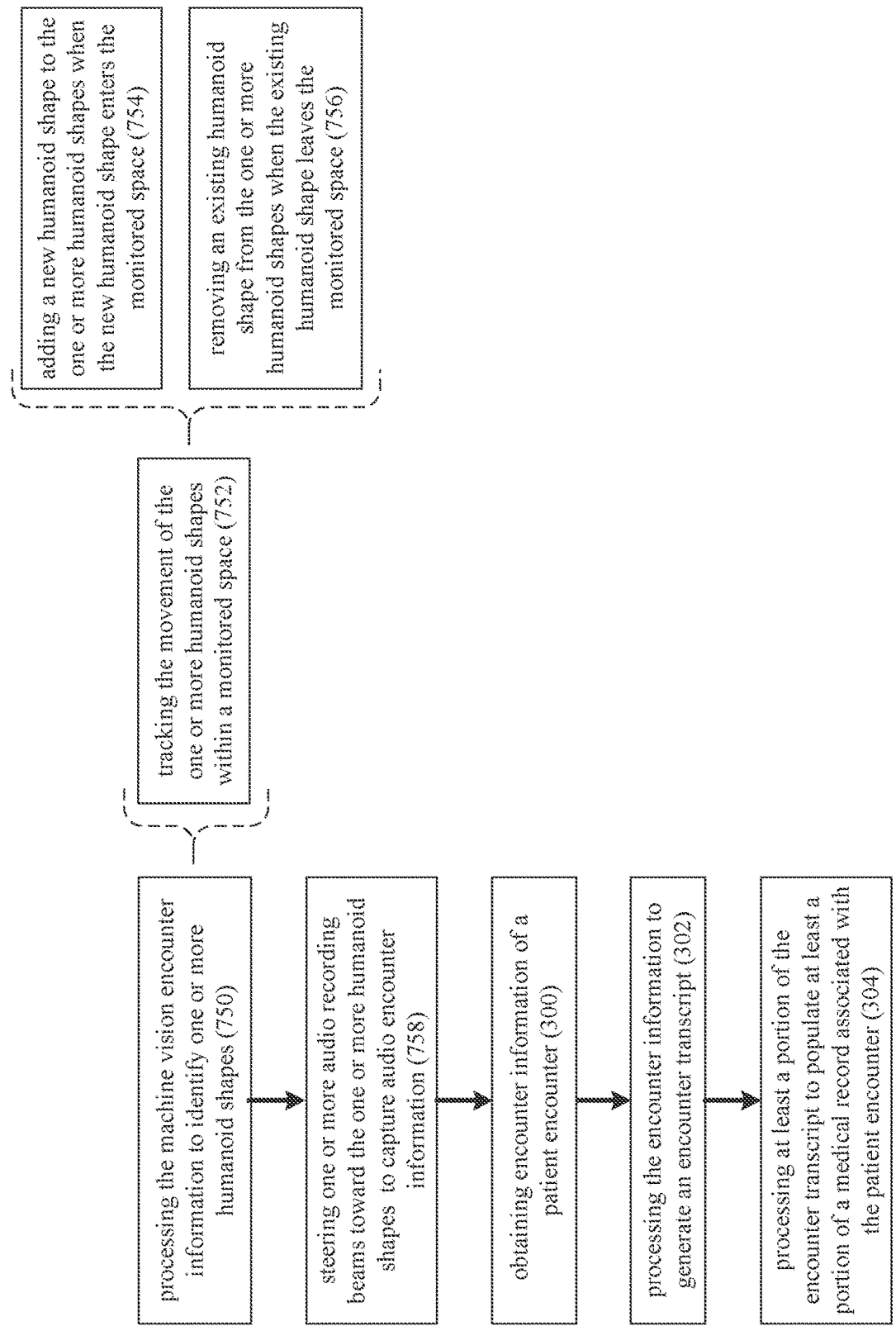
FIG. 15 is a flow chart of another implementation of the automated clinical documentation process of FIG. 1.

Accordingly and referring also to FIG. 15, automated clinical documentation process 10 may process 750 the machine vision encounter information (e.g., machine vision encounter information 102) to identify one or more humanoid shapes. As discussed above, examples of machine vision system 100 generally (and ACD client electronic device 34 specifically) may include but are not limited to one or more of an RGB imaging system, an infrared imaging system, an ultraviolet imaging system, a laser imaging system, a SONAR imaging system, a RADAR imaging system, and a thermal imaging system).

When ACD client electronic device 34 includes a visible light imaging system (e.g., an RGB imaging system), ACD client electronic device 34 may be configured to monitor various objects within monitored space 130 by recording motion video in the visible light spectrum of these various objects. When ACD client electronic device 34 includes an invisible light imaging systems (e.g., a laser imaging system, an infrared imaging system and/or an ultraviolet imaging system), ACD client electronic device 34 may be configured to monitor various objects within monitored space 130 by recording motion video in the invisible light spectrum of these various objects. When ACD client electronic device 34 includes an X-ray imaging system, ACD client electronic device 34 may be configured to monitor various objects within monitored space 130 by recording energy in the X-ray spectrum of these various objects. When ACD client electronic device 34 includes a SONAR imaging system, ACD client electronic device 34 may be configured to monitor various objects within monitored space 130 by transmitting soundwaves that may be reflected off of these various objects. When ACD client electronic device 34 includes a RADAR imaging system, ACD client electronic device 34 may be configured to monitor various objects within monitored space 130 by transmitting radio waves that may be reflected off of these various objects. When ACD client electronic device 34 includes a thermal imaging system, ACD client electronic device 34 may be configured to monitor various objects within monitored space 130 by tracking the thermal energy of these various objects.

As discussed above, ACD compute system 12 may be configured to access one or more datasources 118 (e.g., plurality of individual datasources 120, 122, 124, 126, 128), wherein examples of which may include but are not limited to one or more of a user profile datasource, a voice print datasource, a voice characteristics datasource (e.g., for adapting the automated speech recognition models), a face print datasource, a humanoid shape datasource, a humanoid shape datasource, an utterance identifier datasource, a wearable token identifier datasource, an interaction identifier datasource, a medical conditions symptoms datasource, a prescriptions compatibility datasource, a medical insurance coverage datasource, and a home healthcare datasource.

Accordingly and when processing 750 the machine vision encounter information (e.g., machine vision encounter information 102) to identify one or more humanoid shapes, automated clinical documentation process 10 may be configured to compare the humanoid shapes defined within one or more datasources 118 to potential humanoid shapes within the machine vision encounter information (e.g., machine vision encounter information 102).

When processing 750 the machine vision encounter information (e.g., machine vision encounter information 102) to identify one or more humanoid shapes, automated clinical documentation process 10 may track 752 the movement of the one or more humanoid shapes within the monitored space (e.g., monitored space 130). For example and when tracking 752 the movement of the one or more humanoid shapes within monitored space 130, automated clinical documentation process 10 may add 754 a new humanoid shape to the one or more humanoid shapes when the new humanoid shape enters the monitored space (e.g., monitored space 130) and/or may remove 756 an existing humanoid shape from the one or more humanoid shapes when the existing humanoid shape leaves the monitored space (e.g., monitored space 130).

For example, assume that a lab technician (e.g., encounter participant 242) temporarily enters monitored space 130 to chat with encounter participant 230. Accordingly, automated clinical documentation process 10 may add 754 encounter participant 242 to the one or more humanoid shapes being tracked 752 when the new humanoid shape (i.e., encounter participant 242) enters monitored space 130. Further, assume that the lab technician (e.g., encounter participant 242) leaves monitored space 130 after chatting with encounter participant 230. Therefore, automated clinical documentation process 10 may remove 756 encounter participant 242 from the one or more humanoid shapes being tracked 752 when the humanoid shape (i.e., encounter participant 242) leaves monitored space 130.

Also and when tracking 752 the movement of the one or more humanoid shapes within monitored space 130, automated clinical documentation process 10 may monitor the trajectories of the various humanoid shapes within monitored space 130. Accordingly, assume that when leaving monitored space 130, encounter participant 242 walks in front of (or behind) encounter participant 226. As automated clinical documentation process 10 is monitoring the trajectories of (in this example) encounter participant 242 (who is e.g., moving from left to right) and encounter participant 226 (who is e.g., stationary), when encounter participant 242 passes in front of (or behind) encounter participant 226, the identities of these two humanoid shapes may not be confused by automated clinical documentation process 10.

Automated clinical documentation process 10 may be configured to obtain 300 the encounter information of the patient encounter (e.g., a visit to a doctor's office), which may include machine vision encounter information 102 (in the manner described above) and/or audio encounter information 106.

Automated clinical documentation process 10 may steer 758 one or more audio recording beams (e.g., audio recording beams 220, 222, 224) toward the one or more humanoid shapes (e.g., encounter participants 226, 228, 230) to capture audio encounter information (e.g., audio encounter information 106), wherein audio encounter information 106 may be included within the encounter information (e.g., machine vision encounter information 102 and/or audio encounter information 106).

Specifically, automated clinical documentation process 10 (via modular ACD system 54 and/or audio recording system 104) may utilize one or more of the discrete audio acquisition devices (e.g., audio acquisition devices 202, 204, 206, 208, 210, 212, 214, 216, 218) to form an audio recording beam. For example, automated clinical documentation process 10 may utilize audio acquisition device 210 to form audio recording beam 220, thus enabling the capturing of audio (e.g., speech) produced by encounter participant 226 (as audio acquisition device 210 is pointed to (i.e., directed toward) encounter participant 226). Additionally, automated clinical documentation process 10 may utilize audio acquisition devices 204, 206 to form audio recording beam 222, thus enabling the capturing of audio (e.g., speech) produced by encounter participant 228 (as audio acquisition devices 204, 206 are pointed to (i.e., directed toward) encounter participant 228). Additionally, automated clinical documentation process 10 may utilize audio acquisition devices 212, 214 to form audio recording beam 224, thus enabling the capturing of audio (e.g., speech) produced by encounter participant 230 (as audio acquisition devices 212, 214 are pointed to (i.e., directed toward) encounter participant 230).

Once obtained, automated clinical documentation process 10 may process 302 the encounter information (e.g., machine vision encounter information 102 and/or audio encounter information 106) to generate encounter transcript 234 and may process 304 at least a portion of encounter transcript 234 to populate at least a portion of a medical record (e.g., medical record 236) associated with the patient encounter (e.g., a visit to a doctor's office).

Automated clinical documentation process 10 may be configured to filter out audio that does not belong within audio recording beams (e.g., audio recording beams 220, 222, 224) using e.g., echo cancellation and/or blind source processing.

Figure 16:
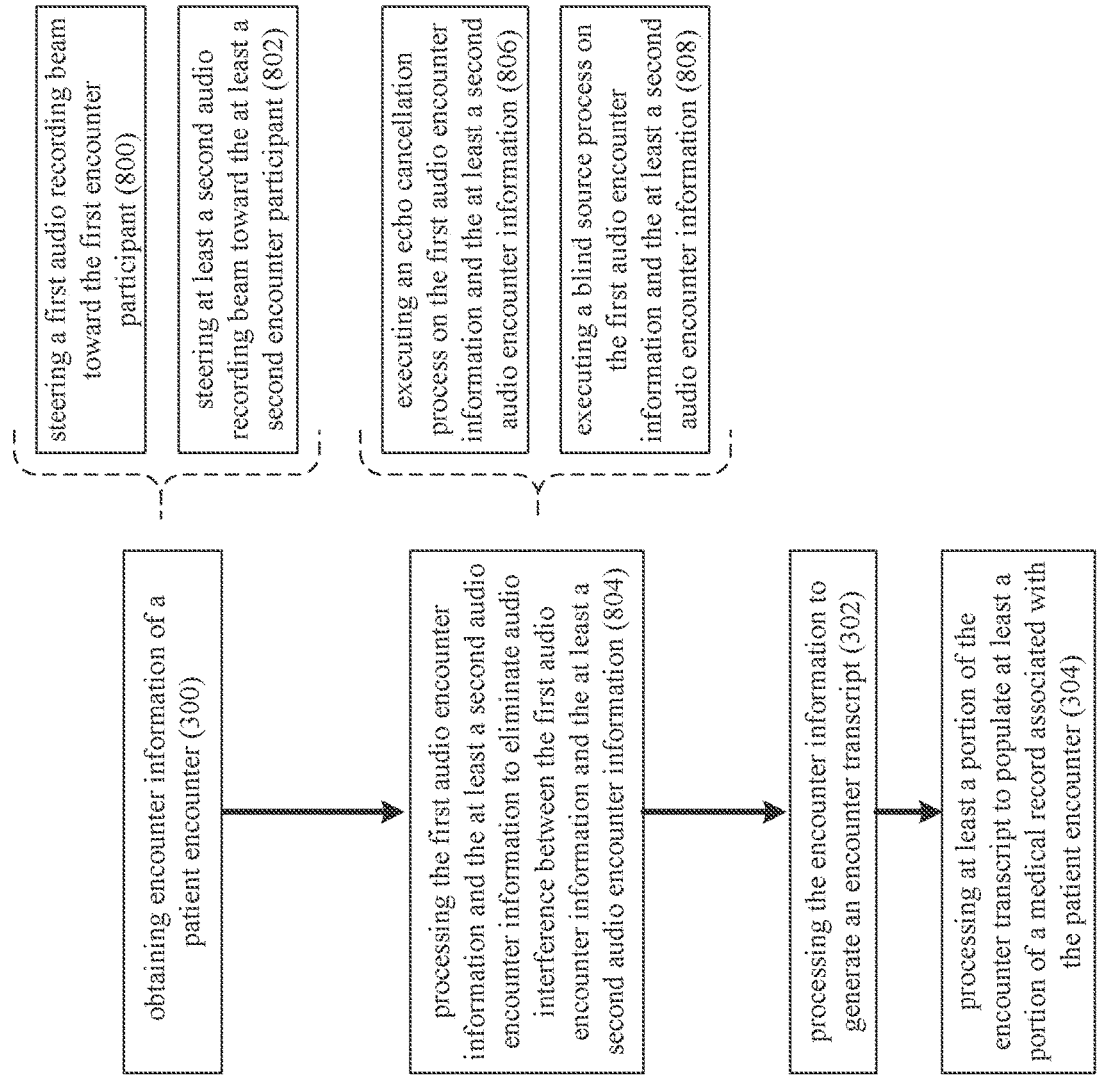
FIG. 16 is a flow chart of another implementation of the automated clinical documentation process of FIG. 1.

Accordingly and referring also to FIG. 16, automated clinical documentation process 10 may be configured to obtain 300 encounter information (e.g., machine vision encounter information 102 and/or audio encounter information 106) of a patient encounter (e.g., a visit to a doctor's office), wherein the encounter information (e.g., machine vision encounter information 102 and/or audio encounter information 106) includes first audio encounter information obtained from a first encounter participant and at least a second audio encounter information obtained from at least a second encounter participant.

When obtaining 300 encounter information (e.g., machine vision encounter information 102 and/or audio encounter information 106) of a patient encounter (e.g., a visit to a doctor's office), automated clinical documentation process 10 may steer 800 a first audio recording beam toward the first encounter participant; and may steer 802 at least a second audio recording beam toward the at least a second encounter participant.

Specifically, automated clinical documentation process 10 (via modular ACD system 54 and/or audio recording system 104) may utilize one or more of the discrete audio acquisition devices (e.g., audio acquisition devices 202, 204, 206, 208, 210, 212, 214, 216, 218) to form an audio recording beam. For example, automated clinical documentation process 10 may utilize audio acquisition device 210 to form audio recording beam 220, thus enabling the capturing of audio (e.g., speech) produced by encounter participant 226 (as audio acquisition device 210 is pointed to (i.e., directed toward) encounter participant 226). Additionally, automated clinical documentation process 10 may utilize audio acquisition devices 204, 206 to form audio recording beam 222, thus enabling the capturing of audio (e.g., speech) produced by encounter participant 228 (as audio acquisition devices 204, 206 are pointed to (i.e., directed toward) encounter participant 228). Additionally, automated clinical documentation process 10 may utilize audio acquisition devices 212, 214 to form audio recording beam 224, thus enabling the capturing of audio (e.g., speech) produced by encounter participant 230 (as audio acquisition devices 212, 214 are pointed to (i.e., directed toward) encounter participant 230).

As there is a comparatively narrow angle of separation between audio recording beam 220 and audio recording beam 224, automated clinical documentation process 10 may process 804 the first audio encounter information (e.g., audio encounter information 106A from encounter participant 226) and the at least a second audio encounter information (e.g., audio encounter information 106C from encounter participant 230) to eliminate audio interference between the first audio encounter information (e.g., audio encounter information 106A) and the at least a second audio encounter information (e.g., audio encounter information 106C).

One example of such audio interference between the first audio encounter information (e.g., audio encounter information 106A) and the at least a second audio encounter information (e.g., audio encounter information 106C) may include but is not limited to crosstalk between the first audio encounter information (e.g., audio encounter information 106A) and the at least a second audio encounter information (e.g., audio encounter information 106C). As is known in the art, crosstalk may occur when two or more people are speaking simultaneously when e.g., speakers are interrupting each other or during what may be referred to as "active listening" (i.e., basically indicating attention and comprehension with a lot of utterances of e.g., "yes", "got it" and "hmm". Other common sounds (e.g., heavy breathing and deep breathing) by the patient may also impact automated clinical documentation process 10 and may need to be filtered out.

When processing 804 the first audio encounter information (e.g., audio encounter information 106A) and the at least a second audio encounter information (e.g., audio encounter information 106C) to eliminate audio interference, automated clinical documentation process 10 may execute 806 an echo cancellation process on the first audio encounter information (e.g., audio encounter information 106A) and the at least a second audio encounter information (e.g., audio encounter information 106C).

As is known in the art, echo cancellation is a method for improving signal quality by removing echo after it is already present. This method may be called acoustic echo suppression (AES) and acoustic echo cancellation (AEC), and more rarely line echo cancellation (LEC). In some cases, these terms are more precise, as there are various types and causes of echo with unique characteristics, including acoustic echo (sounds from a loudspeaker being reflected and recorded by a microphone, which can vary substantially over time) and line echo (electrical impulses caused by e.g., coupling between the sending and receiving wires, impedance mismatches, electrical reflections, etc., which varies much less than acoustic echo). Accordingly and in this configurations, such echo cancellation methodologies may be utilized to e.g., eliminate the echo of a second speaker that appears in the audio recording beam steered at a closely-positioned first speaker; while also eliminating the echo of the first speaker that appears in the audio recording beam steered at the closely-positioned second speaker.

When processing 804 the first audio encounter information (e.g., audio encounter information 106A) and the at least a second audio encounter information (e.g., audio encounter information 106C) to eliminate audio interference, automated clinical documentation process 10 may execute 808 a blind source separation process on the first audio encounter information (e.g., audio encounter information 106A) and the at least a second audio encounter information (e.g., audio encounter information 106C).

As is known in the art, blind source separation is the separation of a set of source signals from a set of mixed signals, without the aid of information (or with very little information) about the source signals or the mixing process. This problem is in general highly underdetermined but useful solutions can be derived under a surprising variety of conditions. Much of the early literature in this field focuses on the separation of temporal signals such as audio. However, blind source separation is now routinely performed on multidimensional data, such as images and tensors that may involve no time dimension whatsoever. Since the chief difficulty of the problem is its underdetermination, methods for blind source separation generally seek to narrow the set of possible solutions in a way that is unlikely to exclude the desired solution. In one approach, exemplified by principal and independent component analysis, one seeks source signals that are minimally correlated or maximally independent in a probabilistic or information-theoretic sense. A second approach, exemplified by nonnegative matrix factorization, is to impose structural constraints on the source signals. These structural constraints may be derived from a generative model of the signal, but are more commonly heuristics justified by good empirical performance. A common theme in the second approach is to impose some kind of low-complexity constraint on the signal, such as sparsity in some basis for the signal space. This approach can be particularly effective if one requires not the whole signal, but merely its most salient features.

As discussed above, modular ACD system 54 and/or audio recording system 104 may be configured to utilize null-steering precoding to cancel interference between speakers and/or noise.

Once processed 804, automated clinical documentation process 10 may process 302 the encounter information (e.g., machine vision encounter information 102 and/or audio encounter information 106) to generate encounter transcript 234 and may process 304 at least a portion of encounter transcript 234 to populate at least a portion of a medical record (e.g., medical record 236) associated with the patient encounter (e.g., a visit to a doctor's office).

Figure 17:
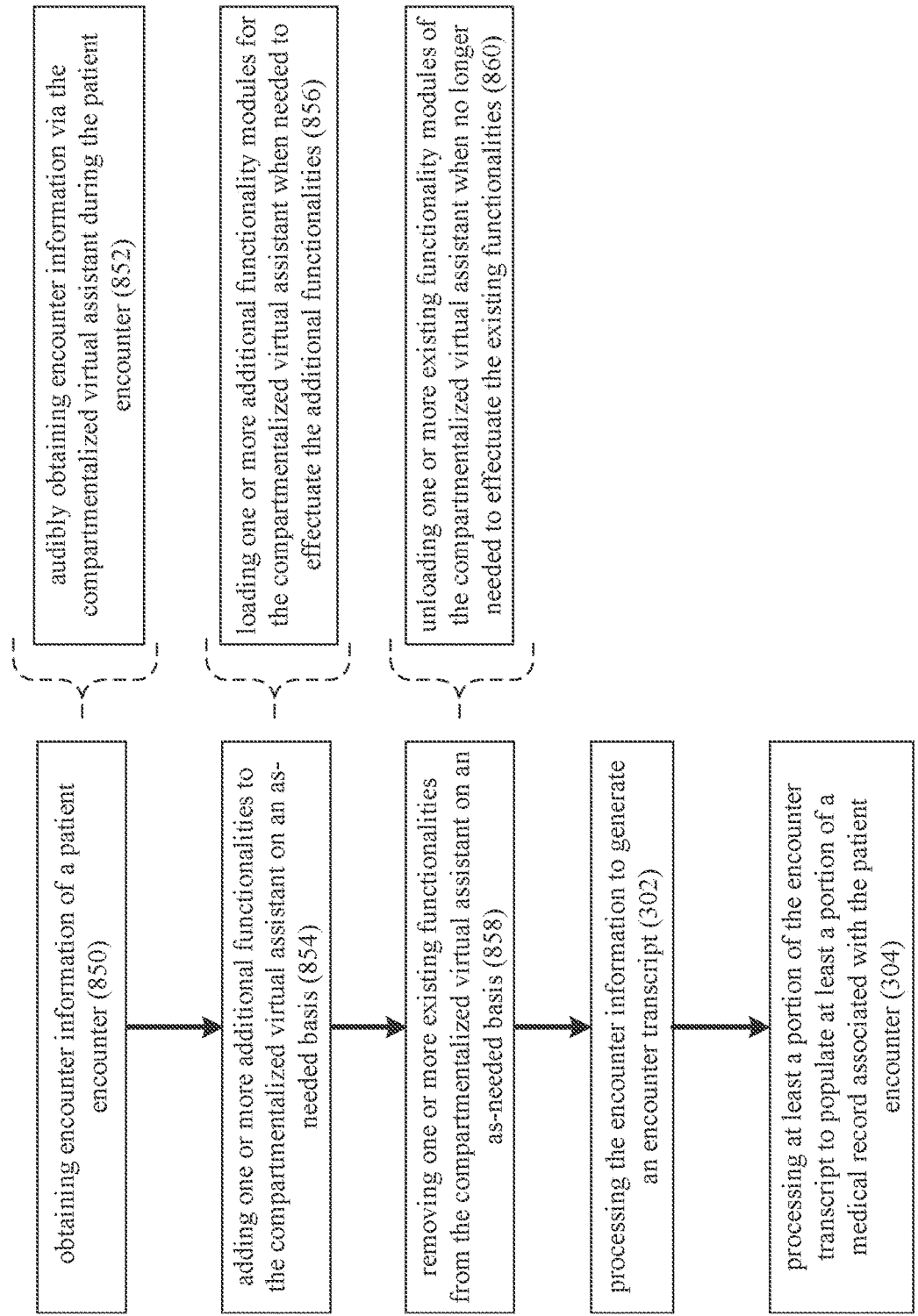
FIG. 17 is a flow chart of another implementation of the automated clinical documentation process of FIG. 1.

Automated clinical documentation process 10 may be configured to include a virtual assistant (e.g., virtual assistant 238) that is modular in design. While this virtual assistant (e.g., virtual assistant 238) may include only one persona (e.g., Nuance's Florence) for interacting with users, this virtual assistant (e.g., virtual assistant 238) may include various functionality modules that may be configured to run in parallel with each other and be added to (or removed from) the virtual assistant (e.g., virtual assistant 238) as needed Accordingly and referring also to FIG. 17, automated clinical documentation process 10 may be configured to obtain 850 encounter information (e.g., machine vision encounter information 102 and/or audio encounter information 106) via a compartmentalized virtual assistant (e.g., virtual assistant 238) during a patient encounter (e.g., a visit to a doctor's office), wherein the compartmentalized virtual assistant (e.g., virtual assistant 238) may include a core functionality module (e.g., core functionality module 244). An example of core functionality module 244 may include but is not limited to a functionality module that verbally interacts with an encounter participant (e.g., encounter participant 228) of the patient encounter (e.g., a visit to a doctor's office).

As discussed above, virtual assistant 238 may be configured to aid medical professionals (e.g., doctors, nurses, physician's assistants, lab technicians, physical therapists, scribes (e.g., a transcriptionist) and/or staff members involved in the patient encounter) with the gathering of encounter information (e.g., machine vision encounter information 102 and/or audio encounter information 106) during various portions of the patient encounter (e.g., encounter participant 228 visiting the doctor's office). For example and during a pre-visit portion of the patient encounter (e.g., a visit to a doctor's office), the patient may be directed to a patient "check-in" area within monitored space 130, wherein the compartmentalized virtual assistant (e.g., virtual assistant 238) may verbally interact with the encounter participant (e.g., encounter participant 228). Accordingly and within this "check-in" area, automated clinical documentation process 10 may audibly obtain 852 encounter information (e.g., machine vision encounter information 102 and/or audio encounter information 106) via the compartmentalized virtual assistant (e.g., virtual assistant 238).

The compartmentalized virtual assistant (e.g., virtual assistant 238) may be configured to perform various different types of functionality during the patient encounter (e.g., a visit to a doctor's office). For example and during one portion of the patient encounter (e.g., a visit to a doctor's office), the compartmentalized virtual assistant (e.g., virtual assistant 238) may require functionality to interact with a medical insurance coverage datasource to determine whether a particular medication/medical procedure that was mentioned during a patient encounter (e.g., a visit to a doctor's office) is covered by the medical insurance plan of the patient. However, during other portions of the patient encounter (e.g., a visit to a doctor's office), such functionality may not be needed. Further and during other patient encounters, such functionality may not be needed at all.

Accordingly, automated clinical documentation process 10 may be configured to add 854 one or more additional functionalities to the compartmentalized virtual assistant (e.g., virtual assistant 238) on an as-needed basis. Accordingly and if during the patient encounter (e.g., a visit to a doctor's office), a certain functionality is needed, the appropriate functionality module (e.g., functionality module 246) may be added 854 by automated clinical documentation process 10. When adding 854 one or more additional functionalities to the compartmentalized virtual assistant (e.g., virtual assistant 238) on an as-needed basis, automated clinical documentation process 10 may load 856 one or more additional functionality modules (e.g., functionality module 246) for the compartmentalized virtual assistant (e.g., virtual assistant 238) when needed to effectuate the additional functionalities. Accordingly and by only loading 856 functionality modules (e.g., functionality module 246) on an as-needed basis, modular ACD system 54 will not be unduly loaded, thus efficiently utilizing the system resources (e.g., memory resources, compute resources, network resources, etc.) of modular ACD system 54.

Further, automated clinical documentation process 10 may be configured to remove 858 one or more existing functionalities from the compartmentalized virtual assistant (e.g., virtual assistant 238) on an as-needed basis. Accordingly and when, during the patient encounter (e.g., a visit to a doctor's office) a certain functionality is no longer needed, the appropriate functionality module (e.g., functionality module 248) may be removed 858 by automated clinical documentation process 10. When removing 858 one or more existing functionalities from the compartmentalized virtual assistant (e.g., virtual assistant 238) on an as-needed basis, automated clinical documentation process 10 may unload 860 one or more existing functionality modules (e.g., functionality module 248) of the compartmentalized virtual assistant (e.g., virtual assistant 238) when no longer needed to effectuate the existing functionalities. Accordingly and by unloading 860 functionality modules (e.g., functionality module 248) on an as-needed basis, modular ACD system 54 will not be unduly loaded, thus efficiently utilizing the system resources (e.g., memory resources, compute resources, network resources, etc.) of modular ACD system 54.

Once obtained 850, automated clinical documentation process 10 may process 302 the encounter information (e.g., machine vision encounter information 102 and/or audio encounter information 106) to generate encounter transcript 234 and may process 304 at least a portion of encounter transcript 234 to populate at least a portion of a medical record (e.g., medical record 236) associated with the patient encounter (e.g., a visit to a doctor's office).

Automated clinical documentation process 10 may be configured to allow for direct interaction of various functionality modules (e.g., functionality modules 244, 246, 248) of the compartmentalized virtual assistant (e.g., virtual assistant 238), thus not requiring hub & spoke interaction of these functionality modules.

Figure 18:
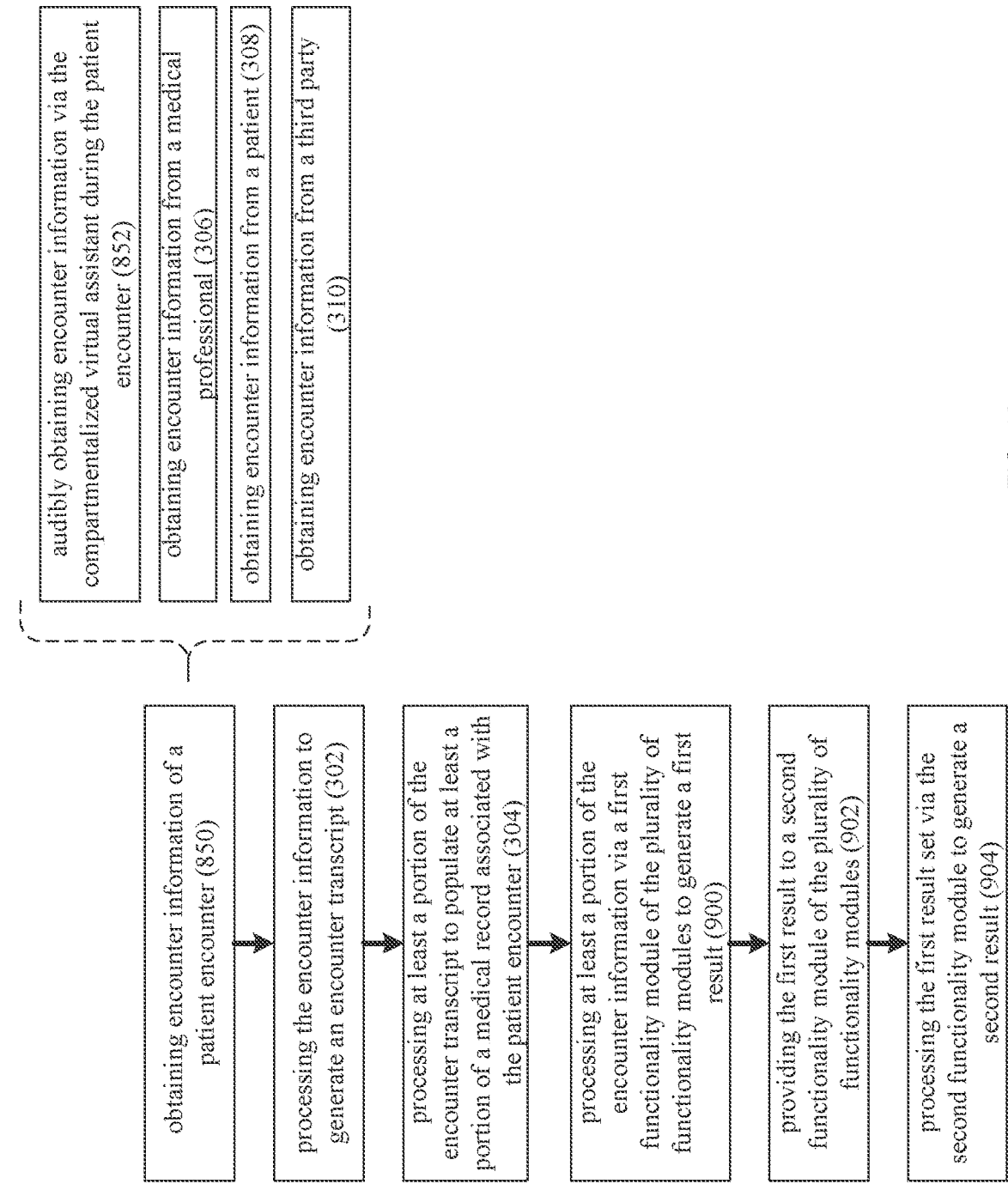
FIG. 18 is a flow chart of another implementation of the automated clinical documentation process of FIG. 1.

Accordingly and referring also to FIG. 18, automated clinical documentation process 10 may be configured to obtain 850 encounter information (e.g., machine vision encounter information 102 and/or audio encounter information 106) via the compartmentalized virtual assistant (e.g., virtual assistant 238) during a patient encounter (e.g., a visit to a doctor's office), wherein the compartmentalized virtual assistant (e.g., virtual assistant 238) may include a plurality of functionality modules (e.g., functionality modules 244, 246, 248).

As discussed above, virtual assistant 238 may be configured to aid medical professionals (e.g., doctors, nurses, physician's assistants, lab technicians, physical therapists, scribes (e.g., a transcriptionist) and/or staff members involved in the patient encounter) with the gathering of encounter information (e.g., machine vision encounter information 102 and/or audio encounter information 106) during various portions of the patient encounter (e.g., encounter participant 228 visiting the doctor's office). For example and during a pre-visit portion of the patient encounter (e.g., a visit to a doctor's office), the patient may be directed to a patient "check-in" area within monitored space 130, wherein the compartmentalized virtual assistant (e.g., virtual assistant 238) may verbally interact with the encounter participant (e.g., encounter participant 228). Accordingly and within this "check-in" area, automated clinical documentation process 10 may audibly obtain 852 encounter information (e.g., machine vision encounter information 102 and/or audio encounter information 106) via the compartmentalized virtual assistant (e.g., virtual assistant 238).

When obtaining 850 encounter information (e.g., machine vision encounter information 102 and/or audio encounter information 106), automated clinical documentation process 10 may: obtain 306 encounter information (e.g., machine vision encounter information 102 and/or audio encounter information 106) from a medical professional; obtain 308 encounter information (e.g., machine vision encounter information 102 and/or audio encounter information 106) from a patient; and obtain 310 encounter information (e.g., machine vision encounter information 102 and/or audio encounter information 106) from a third party. Further and when obtaining 300 encounter information (e.g., machine vision encounter information 102 and/or audio encounter information 106), automated clinical documentation process 10 may obtain 300 the encounter information (e.g., machine vision encounter information 102 and/or audio encounter information 106) from previous (related or unrelated) patient encounters. For example, if the current patient encounter is actually the third visit that the patient is making concerning e.g., shortness of breath, the encounter information from the previous two visits (i.e., the previous two patient encounters) may be highly-related and may be obtained 300 by automated clinical documentation process 10.

Once obtained 850, automated clinical documentation process 10 may process 302 the encounter information (e.g., machine vision encounter information 102 and/or audio encounter information 106) to generate encounter transcript 234 and may process 304 at least a portion of encounter transcript 234 to populate at least a portion of a medical record (e.g., medical record 236) associated with the patient encounter (e.g., a visit to a doctor's office).

As will be discussed below in greater detail, automated clinical documentation process 10 may process 900 at least a portion of the encounter information (e.g., machine vision encounter information 102 and/or audio encounter information 106) via a first functionality module (e.g., functionality module 246) of the plurality of functionality modules (e.g., functionality modules 244, 246, 248) to generate a first result (e.g., result set 250). Automated clinical documentation process 10 may provide 902 the first result (e.g., result set 250) to a second functionality module (e.g., functionality module 244) of the plurality of functionality modules (e.g., functionality modules 244, 246, 248). Automated clinical documentation process 10 may then process 904 the first result (e.g., result set 250) via the second functionality module (e.g., functionality module 244) to generate a second result (e.g., result set 252), which may be provided to a third functionality module (e.g., functionality module 248) of the plurality of functionality modules (e.g., functionality modules 244, 246, 248) for processing.

As discussed above, automated clinical documentation process 10 may be configured to include a virtual assistant (e.g., virtual assistant 238) that is modular in design. So while this virtual assistant (e.g., virtual assistant 238) may include only one persona (e.g., Nuance's Florence) for interacting with users, this virtual assistant (e.g., virtual assistant 238) may include various functionality modules (e.g., functionality modules 244, 246, 248) that may be configured to run in parallel with each other and effectuate different functionalities.

Accordingly, assume for this example that encounter participant 226 is going to prescribe an RA medication to encounter participant 228. Accordingly, the first functionality module (e.g., functionality module 246) may be an insurance functionality module that is configured to process 900 this portion of the encounter information and interface with a medical insurance provider of encounter participant 228 to obtain a list of covered RA medications (e.g., first result 250). Functionality module 246 may then provide 902 first result 250 to the second functionality module (e.g., functionality module 244), which may be an adverse interaction functionality module that is configured to identify any potential adverse interactions between the current medications of encounter participant 228 and the approved RA medications defined within first result 250.

Automated clinical documentation process 10 may be configured to utilize machine vision (e.g., an RGB imaging system, an infrared imaging system, an ultraviolet imaging system, a SONAR imaging system, a laser imaging system, a RADAR imaging system and/or a thermal imaging system) to record a visual representation (e.g., machine vision encounter information 102) of the patient encounter (in addition to recording an audio representation (e.g., audio encounter information 106) of the patient encounter), wherein automated clinical documentation process 10 may index/synchronize the visual representation (e.g., machine vision encounter information 102) and the audio representation (e.g., audio encounter information 106) of the patient encounter to produce an encounter recording.

Figure 19:
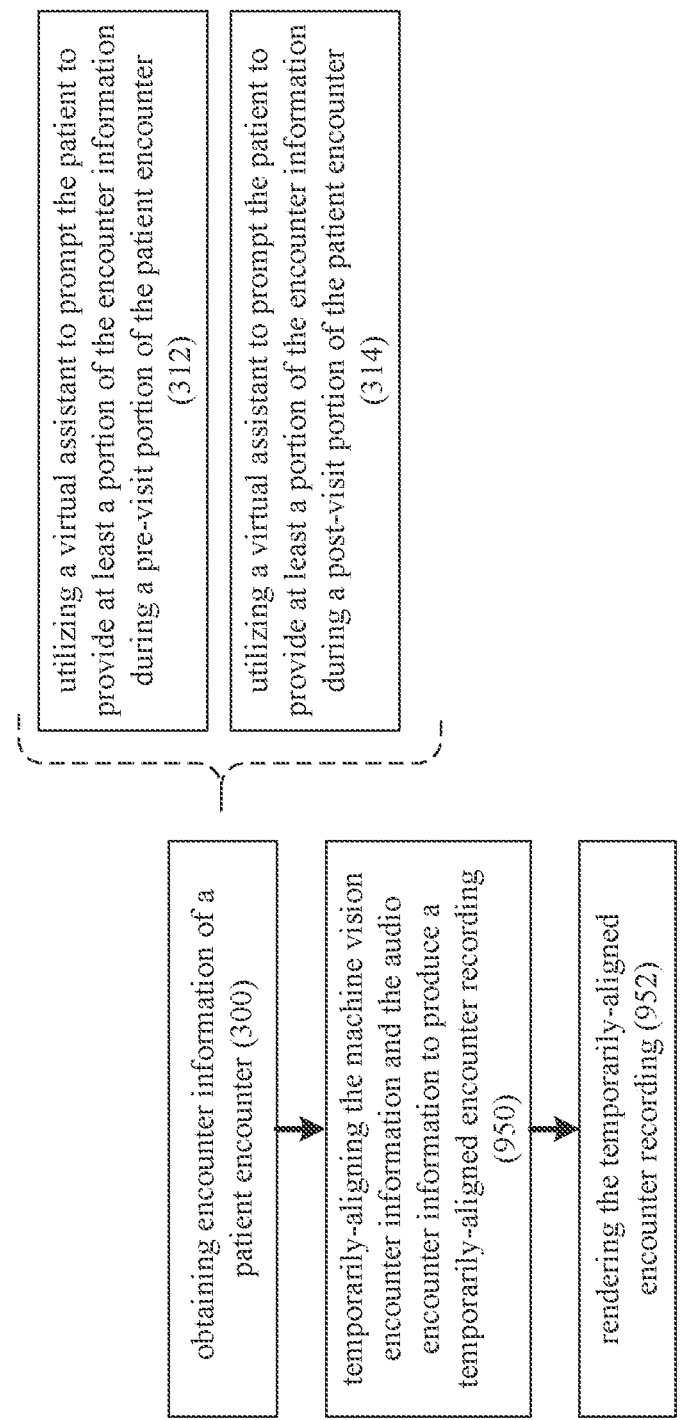
FIG. 19 is a flow chart of another implementation of the automated clinical documentation process of FIG. 1.

Accordingly and referring also to FIG. 19, automated clinical documentation process 10 may be configured to obtain 300 encounter information (e.g., machine vision encounter information 102 and/or audio encounter information 106) of a patient encounter (e.g., a visit to a doctor's office), wherein the encounter information (e.g., machine vision encounter information 102 and/or audio encounter information 106) includes machine vision encounter information and audio encounter information.

As discussed above, virtual assistant 238 may be configured to aid medical professionals (e.g., doctors, nurses, physician's assistants, lab technicians, physical therapists, scribes (e.g., a transcriptionist) and/or staff members involved in the patient encounter) with the gathering of encounter information (e.g., machine vision encounter information 102 and/or audio encounter information 106) during various portions of the patient encounter (e.g., encounter participant 228 visiting the doctor's office).

Accordingly and when obtaining 300 encounter information (e.g., machine vision encounter information 102 and/or audio encounter information 106), automated clinical documentation process 10 may utilize 312 a virtual assistant (e.g., virtual assistant 238) to prompt the patient to provide at least a portion of the encounter information (e.g., machine vision encounter information 102 and/or audio encounter information 106) during a pre-visit portion of the patient encounter (e.g., a visit to a doctor's office).

Further and when obtaining 300 encounter information (e.g., machine vision encounter information 102 and/or audio encounter information 106), automated clinical documentation process 10 may utilize 314 a virtual assistant (e.g., virtual assistant 238) to prompt the patient to provide at least a portion of the encounter information (e.g., machine vision encounter information 102 and/or audio encounter information 106) during a post-visit portion of the patient encounter (e.g., a visit to a doctor's office).

Figure 20:
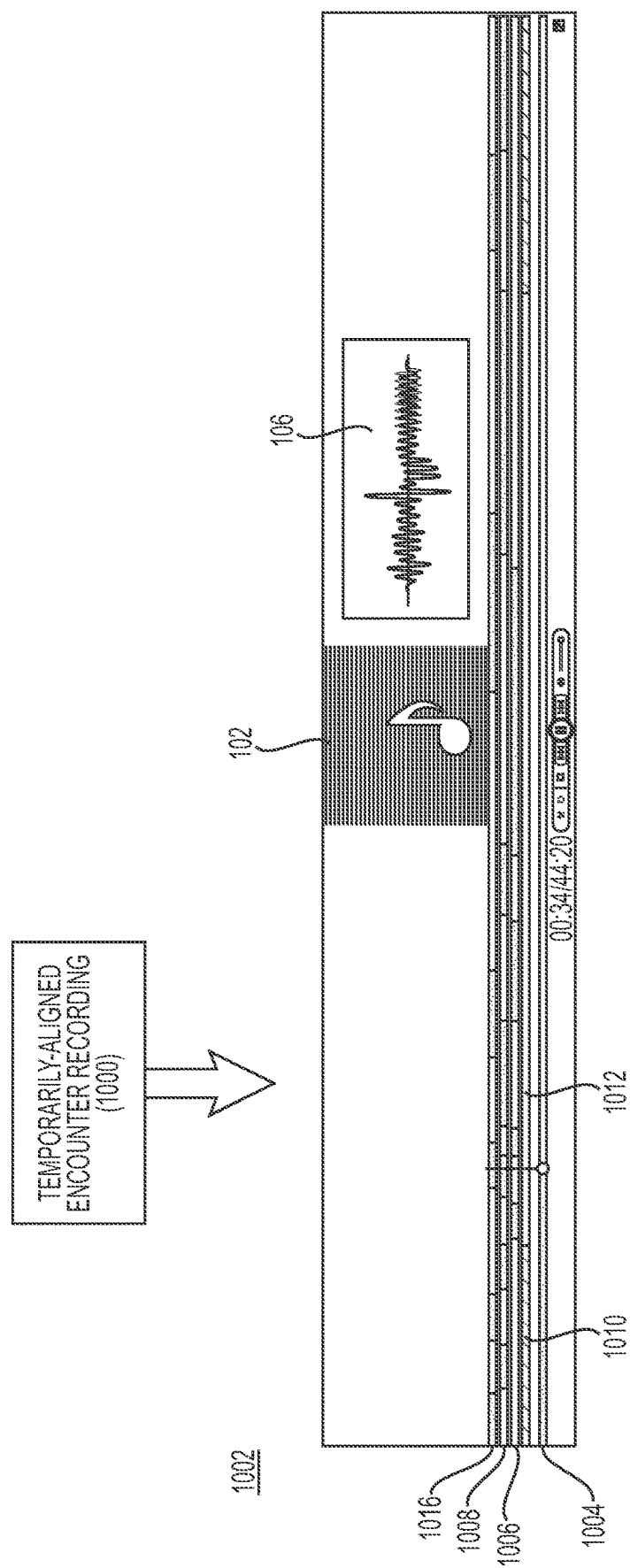
FIG. 20 is a diagrammatic view of an ACD media player for use with the automated clinical documentation process of FIG. 1.

Referring also to FIG. 20, automated clinical documentation process 10 may temporarily-align 950 machine vision encounter information 102 and audio encounter information 106 to produce temporarily-aligned encounter recording 1000, which may be rendered 952 for the user of modular ACD system 54 via ACD media player 1002. Specifically and in one particular implementation of ACD media player 1002, visual representation 1004 of the encounter information may allow the user of modular ACD system 54 to select a particular portion of encounter recording 1000 for rendering, wherein automated clinical documentation process 10 may then render the appropriate portion of machine vision encounter information 102 and audio encounter information 106 in a temporarily aligned fashion.

Automated clinical documentation process 10 may be configured to identify (e.g., temporally & visually) the individual encounter participants (e.g., one or more of encounter participants 226, 228, 230) within an encounter recording of a patient encounter (e.g., a visit to a doctor's office).

Figure 21:
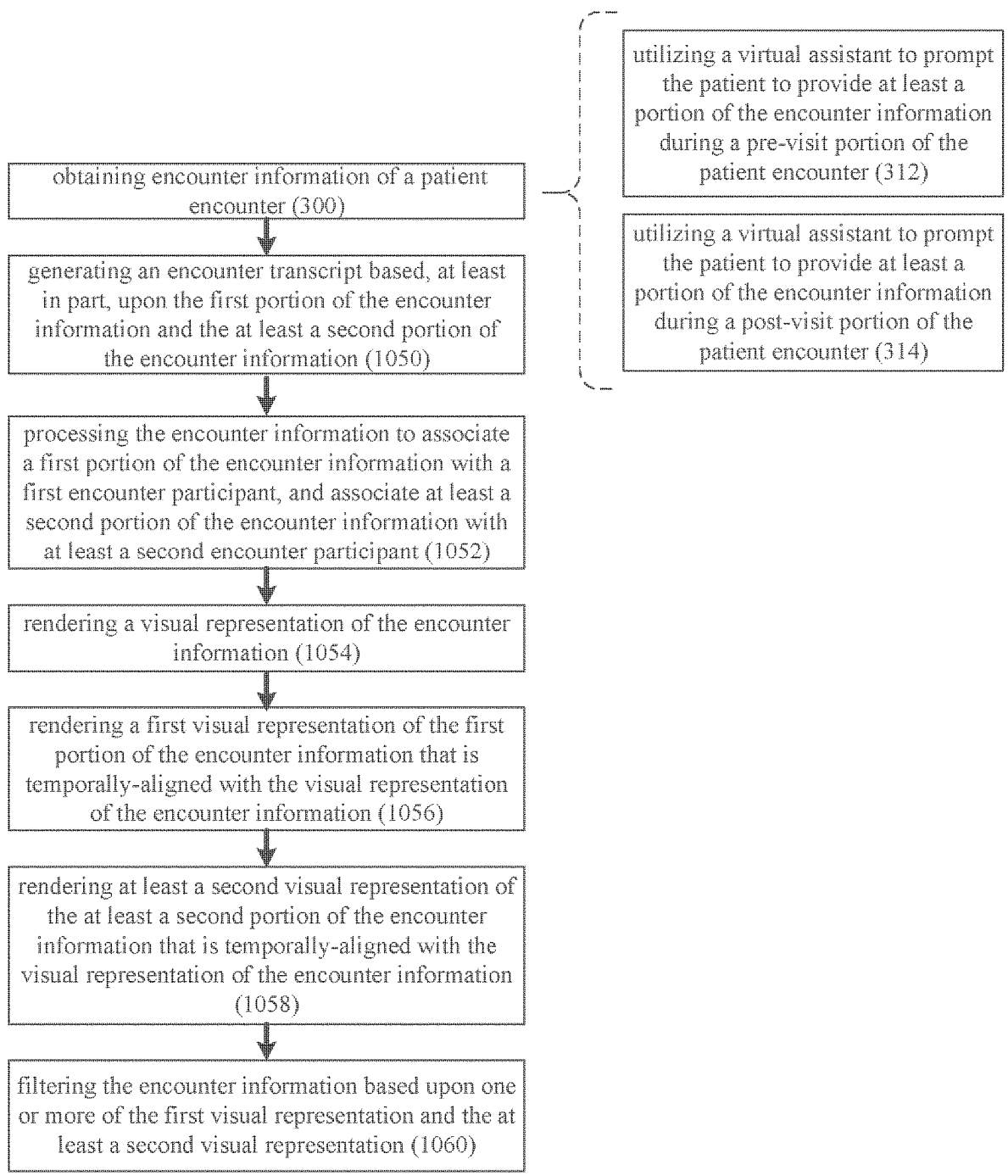
FIG. 21 is a flow chart of another implementation of the automated clinical documentation process of FIG. 1.

Accordingly and referring also to FIG. 21, automated clinical documentation process 10 may be configured to obtain 300 encounter information (e.g., machine vision encounter information 102 and/or audio encounter information 106) of a patient encounter (e.g., a visit to a doctor's office), wherein the encounter information (e.g., machine vision encounter information 102 and/or audio encounter information 106) includes machine vision encounter information and audio encounter information).

As discussed above, virtual assistant 238 may be configured to aid medical professionals (e.g., doctors, nurses, physician's assistants, lab technicians, physical therapists, scribes (e.g., a transcriptionist) and/or staff members involved in the patient encounter) with the gathering of encounter information (e.g., machine vision encounter information 102 and/or audio encounter information 106) during various portions of the patient encounter (e.g., encounter participant 228 visiting the doctor's office).

Accordingly and when obtaining 300 the encounter information (e.g., machine vision encounter information 102 and/or audio encounter information 106), automated clinical documentation process 10 may utilize 312 a virtual assistant (e.g., virtual assistant 238) to prompt the patient to provide at least a portion of the encounter information (e.g., machine vision encounter information 102 and/or audio encounter information 106) during a pre-visit portion of the patient encounter (e.g., a visit to a doctor's office).

Further and when obtaining 300 encounter information (e.g., machine vision encounter information 102 and/or audio encounter information 106), automated clinical documentation process 10 may utilize 314 a virtual assistant (e.g., virtual assistant 238) to prompt the patient to provide at least a portion of the encounter information (e.g., machine vision encounter information 102 and/or audio encounter information 106) during a post-visit portion of the patient encounter (e.g., a visit to a doctor's office).

Automated clinical documentation process 10 may generate 1050 an encounter transcript based, at least in part, upon the first portion of the encounter information (e.g., machine vision encounter information 102 and/or audio encounter information 106) and the at least a second portion of the encounter information (e.g., machine vision encounter information 102 and/or audio encounter information 106).

Automated clinical documentation process 10 may process 1052 the information (e.g., machine vision encounter information 102 and/or audio encounter information 106) information to: associate a first portion (e.g., machine vision encounter information 102A and/or audio encounter information 106A) of the encounter information (e.g., machine vision encounter information 102 and/or audio encounter information 106) with a first encounter participant (e.g., encounter participant 226), and associate at least a second portion (e.g., machine vision encounter information 102B and/or audio encounter information 106B) of the encounter information (e.g., machine vision encounter information 102 and/or audio encounter information 106) with at least a second encounter participant (e.g., encounter participant 228). The association of these various encounter information portions with the various encounter participants may be accomplished in one or more of the methodologies described above (via the use of one or more of voice prints, face prints, wearable tokens, utterances, interactions, etc.).

Once the above-described associations are made, automated clinical documentation process 10 may render 1054 a visual representation (e.g., visual representation 1004) of the encounter information (e.g., machine vision encounter information 102 and/or audio encounter information 106). As discussed above, visual representation 1004 of the encounter information may allow the user of modular ACD system 54 to select a particular portion of encounter recording 1000 for rendering.

Automated clinical documentation process 10 may render 1056 a first visual representation (e.g., first visual representation 1006) of the first portion (e.g., machine vision encounter information 102A and/or audio encounter information 106A) of the encounter information (e.g., machine vision encounter information 102 and/or audio encounter information 106) that is temporally-aligned with visual representation 1004 of the encounter information (e.g., machine vision encounter information 102 and/or audio encounter information 106). Specifically, first visual representation 1006 may be visually indicative of the portions of the encounter information during which the first encounter participant (e.g., encounter participant 226) was speaking (as illustrated by darker grey portions versus lighter grey portions).

Further, automated clinical documentation process 10 may render 1058 at least a second visual representation (e.g., second visual representation 1008) of the at least a second portion (e.g., machine vision encounter information 102B and/or audio encounter information 106B) of the encounter information (e.g., machine vision encounter information 102 and/or audio encounter information 106) that is temporally-aligned with visual representation 1004 of the encounter information (e.g., machine vision encounter information 102 and/or audio encounter information 106). Specifically, second visual representation 1008 may be visually indicative of the portions of the encounter information during which the second encounter participant (e.g., encounter participant 228) was speaking (as illustrated by darker grey portions versus lighter grey portions).

Additionally, automated clinical documentation process 10 may be configured to allow the user of modular ACD system 54 to filter 1060 the encounter information (e.g., machine vision encounter information 102 and/or audio encounter information 106) based upon one or more of the first visual representation (e.g., first visual representation 1006) and the at least a second visual representation (e.g., second visual representation 1008). For example, the user of modular ACD system 54 may select (e.g., via clicking) the appropriate visual representation (or appropriate visual representations) and automated clinical documentation process 10 may filter 1060 encounter recording 1000 based upon the user selections.

Automated clinical documentation process 10 may be configured to identify (e.g., temporally & visually) the individual portions of an encounter recording of a patient encounter (e.g., a visit to a doctor's office).

Figure 22:
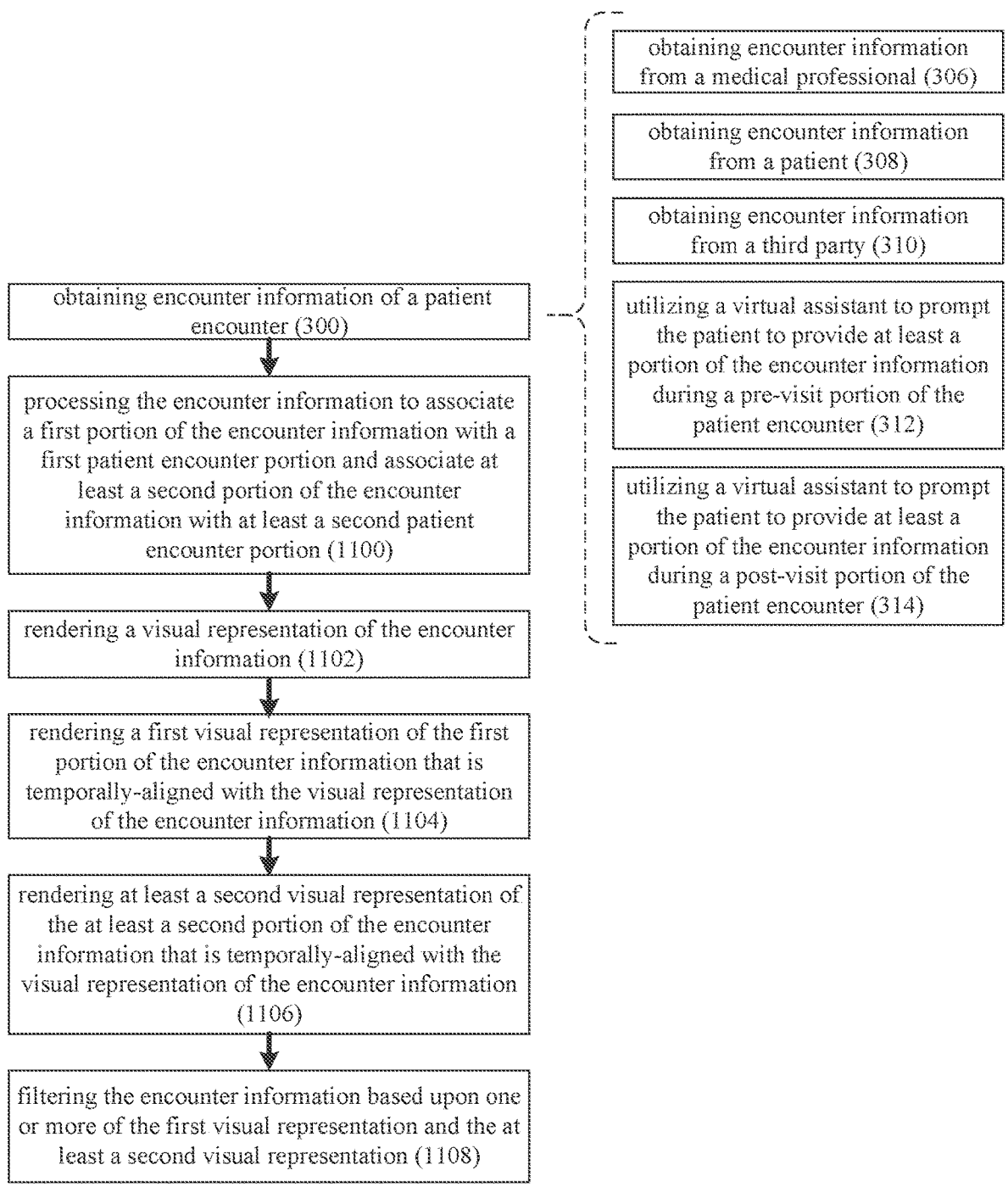
FIG. 22 is a flow chart of another implementation of the automated clinical documentation process of FIG. 1.

Accordingly and referring also to FIG. 22, automated clinical documentation process 10 may be configured to obtain 300 encounter information (e.g., machine vision encounter information 102 and/or audio encounter information 106) of a patient encounter (e.g., a visit to a doctor's office). When obtaining 300 encounter information (e.g., machine vision encounter information 102 and/or audio encounter information 106), automated clinical documentation process 10 may: obtain 306 encounter information (e.g., machine vision encounter information 102 and/or audio encounter information 106) from a medical professional (e.g., encounter participant 226); obtain 308 encounter information (e.g., machine vision encounter information 102 and/or audio encounter information 106) from a patient (e.g., encounter participant 228); and/or obtain 310 encounter information (e.g., machine vision encounter information 102 and/or audio encounter information 106) from a third party (e.g., encounter participant 230). Further and when obtaining 300 encounter information (e.g., machine vision encounter information 102 and/or audio encounter information 106), automated clinical documentation process 10 may obtain 300 the encounter information (e.g., machine vision encounter information 102 and/or audio encounter information 106) from previous (related or unrelated) patient encounters. For example, if the current patient encounter is actually the third visit that the patient is making concerning e.g., shortness of breath, the encounter information from the previous two visits (i.e., the previous two patient encounters) may be highly-related and may be obtained 300 by automated clinical documentation process 10.

As discussed above, virtual assistant 238 may be configured to aid medical professionals (e.g., doctors, nurses, physician's assistants, lab technicians, physical therapists, scribes (e.g., a transcriptionist) and/or staff members involved in the patient encounter) with the gathering of encounter information (e.g., machine vision encounter information 102 and/or audio encounter information 106) during various portions of the patient encounter (e.g., encounter participant 228 visiting the doctor's office).

Accordingly and when obtaining 300 encounter information (e.g., machine vision encounter information 102 and/or audio encounter information 106), automated clinical documentation process 10 may utilize 312 a virtual assistant (e.g., virtual assistant 238) to prompt the patient to provide at least a portion of the encounter information (e.g., machine vision encounter information 102 and/or audio encounter information 106) during a pre-visit portion of the patient encounter (e.g., a visit to a doctor's office).

Further and when obtaining 300 encounter information (e.g., machine vision encounter information 102 and/or audio encounter information 106), automated clinical documentation process 10 may utilize 314 a virtual assistant (e.g., virtual assistant 238) to prompt the patient to provide at least a portion of the encounter information (e.g., machine vision encounter information 102 and/or audio encounter information 106) during a post-visit portion of the patient encounter (e.g., a visit to a doctor's office).

Automated clinical documentation process 10 may process 1100 the encounter information (e.g., machine vision encounter information 102 and/or audio encounter information 106) to: associate a first portion of the encounter information (e.g., machine vision encounter information 102 and/or audio encounter information 106) with a first patient encounter portion (e.g., a pre-visit portion), and associate at least a second portion of the encounter information (e.g., machine vision encounter information 102 and/or audio encounter information 106) with at least a second patient encounter portion (e.g., the visit portion). The association of these various encounter information portions with the various patient encounter portions may be accomplished in one or more of the methodologies described above (via the use of one or more of voice prints, face prints, wearable tokens, utterances, interactions, etc., as well as the specific locations within monitored space 130 in which the various portions of the encounter information were generated).

Once the above-described associations are made, automated clinical documentation process 10 may render 1102 a visual representation (e.g., visual representation 1004) of the encounter information (e.g., machine vision encounter information 102 and/or audio encounter information 106). As discussed above, visual representation 1004 of the encounter information may allow the user of modular ACD system 54 to select a particular portion of encounter recording 1000 for rendering.

Automated clinical documentation process 10 may render 1104 a first visual representation (e.g., first visual representation 1010) of the first portion (e.g., a pre-visit portion) of the encounter information (e.g., machine vision encounter information 102 and/or audio encounter information 106) that is temporally-aligned with the visual representation 1004 of the encounter information (e.g., machine vision encounter information 102 and/or audio encounter information 106). Specifically, first visual representation 1010 may be visually indicative of the pre-visit portion of the encounter information.

Automated clinical documentation process 10 may render 1106 at least a second visual representation (e.g., second visual representation 1012) of the at least a second portion (e.g., a visit portion) of the encounter information (e.g., machine vision encounter information 102 and/or audio encounter information 106) that is temporally-aligned with visual representation 1004 of the encounter information (e.g., machine vision encounter information 102 and/or audio encounter information 106). Specifically, second visual representation 1012 may be visually indicative of the visit portion of the encounter information.

Additionally, automated clinical documentation process 10 may be configured to allow the user of modular ACD system 54 to filter 1108 the encounter information (e.g., machine vision encounter information 102 and/or audio encounter information 106) based upon one or more of the first visual representation (e.g., first visual representation 1010) and the at least a second visual representation (e.g., second visual representation 1012). For example, the user of modular ACD system 54 may select (e.g., via clicking) the appropriate visual representation (or appropriate visual representations) and automated clinical documentation process 10 may filter 1108 encounter recording 1000 based upon the user selections.

Automated clinical documentation process 10 may be configured to reactively identify (at the request of a user) the various portions of the encounter recording that are indicative of a specific medical condition.

Figure 23:
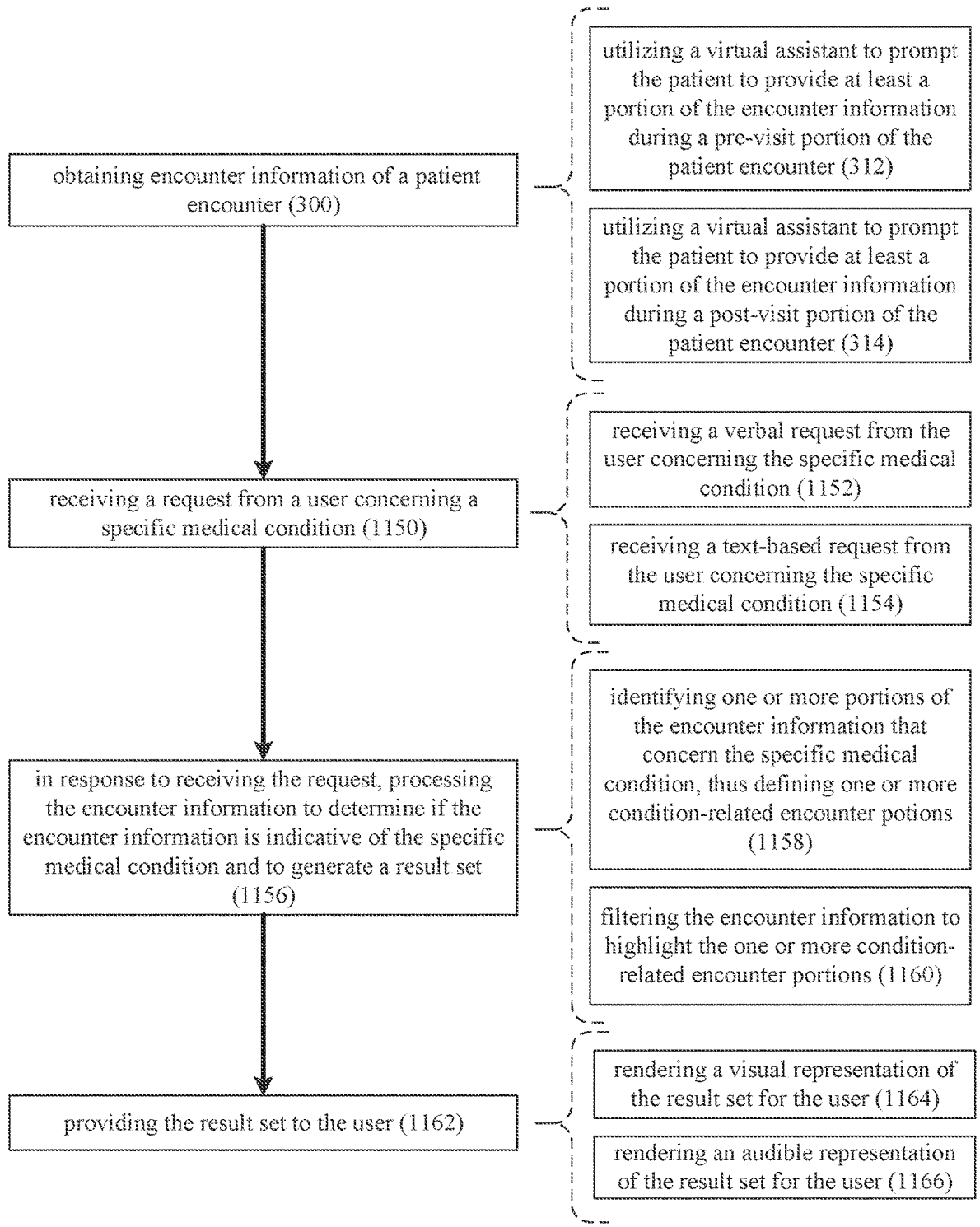
FIG. 23 is a flow chart of another implementation of the automated clinical documentation process of FIG. 1.

Accordingly and referring also to FIG. 23, automated clinical documentation process 10 may be configured to obtain 300 encounter information (e.g., machine vision encounter information 102 and/or audio encounter information 106) of a patient encounter (e.g., a visit to a doctor's office).

As discussed above, virtual assistant 238 may be configured to aid medical professionals (e.g., doctors, nurses, physician's assistants, lab technicians, physical therapists, scribes (e.g., a transcriptionist) and/or staff members involved in the patient encounter) with the gathering of encounter information (e.g., machine vision encounter information 102 and/or audio encounter information 106) during various portions of the patient encounter (e.g., encounter participant 228 visiting the doctor's office).

Accordingly and when obtaining 300 encounter information (e.g., machine vision encounter information 102 and/or audio encounter information 106), automated clinical documentation process 10 may utilize 312 a virtual assistant (e.g., virtual assistant 238) to prompt the patient to provide at least a portion of the encounter information (e.g., machine vision encounter information 102 and/or audio encounter information 106) during a pre-visit portion of the patient encounter (e.g., a visit to a doctor's office).

Further and when obtaining 300 encounter information (e.g., machine vision encounter information 102 and/or audio encounter information 106), automated clinical documentation process 10 may utilize 314 a virtual assistant (e.g., virtual assistant 238) to prompt the patient to provide at least a portion of the encounter information (e.g., machine vision encounter information 102 and/or audio encounter information 106) during a post-visit portion of the patient encounter (e.g., a visit to a doctor's office).

As discussed above, since machine vision system 100 and audio recording system 104 may be positioned throughout monitored space 130, all of the interactions between medical professionals (e.g., encounter participant 226), patients (e.g., encounter participant 228) and third parties (e.g., encounter participant 230) that occur during the patient encounter (e.g., encounter participant 228 visiting the doctor's office) within the monitored space (e.g., monitored space 130) of the clinical environment (e.g., the doctor's office) may be monitored/recorded/processed. Accordingly, a patient "check-in" area within monitored space 130 may be monitored to obtain encounter information (e.g., machine vision encounter information 102 and/or audio encounter information 106) during this pre-visit portion of the patient encounter (e.g., encounter participant 228 visiting the doctor's office). Additionally and as discussed above, this pre-visit encounter information may be obtained via e.g., virtual assistant 238 before the patient (e.g., encounter participant 228) has entered monitored space 130. Further, various rooms within monitored space 130 may be monitored to obtain encounter information (e.g., machine vision encounter information 102 and/or audio encounter information 106) during these various portions of the patient encounter (e.g., while meeting with the doctor, while vital signs and statistics are obtained, and while imaging is performed). Further, a patient "check-out" area within monitored space 130 may be monitored to obtain encounter information (e.g., machine vision encounter information 102 and/or audio encounter information 106) during this post-visit portion of the patient encounter (e.g., encounter participant 228 visiting the doctor's office). Additionally and as discussed above, this post-visit encounter information may be obtained via e.g., virtual assistant 238 after the patient (e.g., encounter participant 228) has left monitored space 130. Further and via machine vision encounter information 102, visual speech recognition (via visual lip reading functionality) may be utilized by automated clinical documentation process 10 to further effectuate the gathering of audio encounter information 106.

Accordingly, a complete recording of the patient encounter (e.g., encounter participant 228 visiting the doctor's office) may be generated, wherein this encounter information (e.g., machine vision encounter information 102 and/or audio encounter information 106) may be processed 302 to generate an encounter transcript (e.g., encounter transcript 234) and at least a portion of this encounter transcript (e.g., encounter transcript 234) may be processed 304 to populate at least a portion of a medical record (e.g., medical record 236) associated with the patient encounter (e.g., the visit to the doctor's office).

Automated clinical documentation process 10 may receive 1150 a request from a user (e.g., a user of modular ACD system 54) concerning a specific medical condition. When receiving 1150 a request from a user (e.g., a user of modular ACD system 54), automated clinical documentation process 10 may: receive 1152 a verbal request from the user (e.g., a user of modular ACD system 54) concerning the specific medical condition; and/or receive 1154 a text-based request from the user (e.g., a user of modular ACD system 54) concerning the specific medical condition.

For example, assume that the user of modular ACD system 54 is encounter participant 226 (e.g., the doctor) who is examining encounter participant 228 (e.g., the patient). Accordingly, assume that encounter participant 226 (e.g., the doctor) is concerned that encounter participant 228 (e.g., the patient) may have diabetes. Accordingly, automated clinical documentation process 10 may receive 1150 a request (either verbal or text-based) from encounter participant 226 requesting that automated clinical documentation process 10 identify any portions of the encounter information (e.g., machine vision encounter information 102 and/or audio encounter information 106) that may be indicative of the presence of diabetes with respect to encounter participant 228.

In response to receiving 1150 the request, automated clinical documentation process 10 may process 1156 the encounter information (e.g., machine vision encounter information 102 and/or audio encounter information 106) to determine if the encounter information (e.g., machine vision encounter information 102 and/or audio encounter information 106) is indicative of this specific medical condition and to generate a result set.

As discussed above, ACD compute system 12 may be configured to access one or more datasources 118 (e.g., plurality of individual datasources 120, 122, 124, 126, 128), examples of which may include but are not limited to one or more of a user profile datasource, a voice print datasource, a voice characteristics datasource (e.g., for adapting the automated speech recognition models), a face print datasource, a humanoid shape datasource, an utterance identifier datasource, a wearable token identifier datasource, an interaction identifier datasource, a medical conditions symptoms datasource, a prescriptions compatibility datasource, a medical insurance coverage datasource, and a home healthcare datasource.

Accordingly, automated clinical documentation process 10 may access the appropriate datasource to identify the symptoms for diabetes and may compare those identified symptoms to the data included within the encounter information (e.g., machine vision encounter information 102 and/or audio encounter information 106).

When processing 1156 the encounter information (e.g., machine vision encounter information 102 and/or audio encounter information 106), automated clinical documentation process 10 may identify 1158 one or more portions of the encounter information (e.g., machine vision encounter information 102 and/or audio encounter information 106) that concern the specific medical condition (in this example, diabetes), thus defining one or more condition-related encounter portions. Automated clinical documentation process 10 may then filter 1160 the encounter information (e.g., machine vision encounter information 102 and/or audio encounter information 106) to highlight the one or more condition-related encounter portions (thus defining result set 1016).

Automated clinical documentation process 10 may then provide 1162 result set 1016 to the user (e.g., encounter participant 226). When providing 1162 result set 1016 to the user (e.g., encounter participant 226), automated clinical documentation process 10 may render 1164 a visual representation of result set 1016 for the user (e.g., encounter participant 226) and/or may render 1166 an audible representation of result set 1016 for the user (e.g., encounter participant 226).

For example, automated clinical documentation process 10 may provide 1162 result set 1016 to encounter participant 226 in the manner shown in FIG. 20, wherein result set 1016 is visually indicative of the portions of the encounter information that concern a specific medical condition (in this example, diabetes). Additionally/alternatively, automated clinical documentation process 10 may provide 1162 result set 1016 as a private verbal message (e.g., that is rendered on an earbud worn by encounter participant 226) that provides the information requested by encounter participant 226 (e.g., "There are 23 portions of this patient encounter that indicate that this patient may have diabetes. An A1C test is recommended".

Automated clinical documentation process 10 may be configured to proactively scan the entire encounter recording to identify any specific medical conditions.

Figure 24:
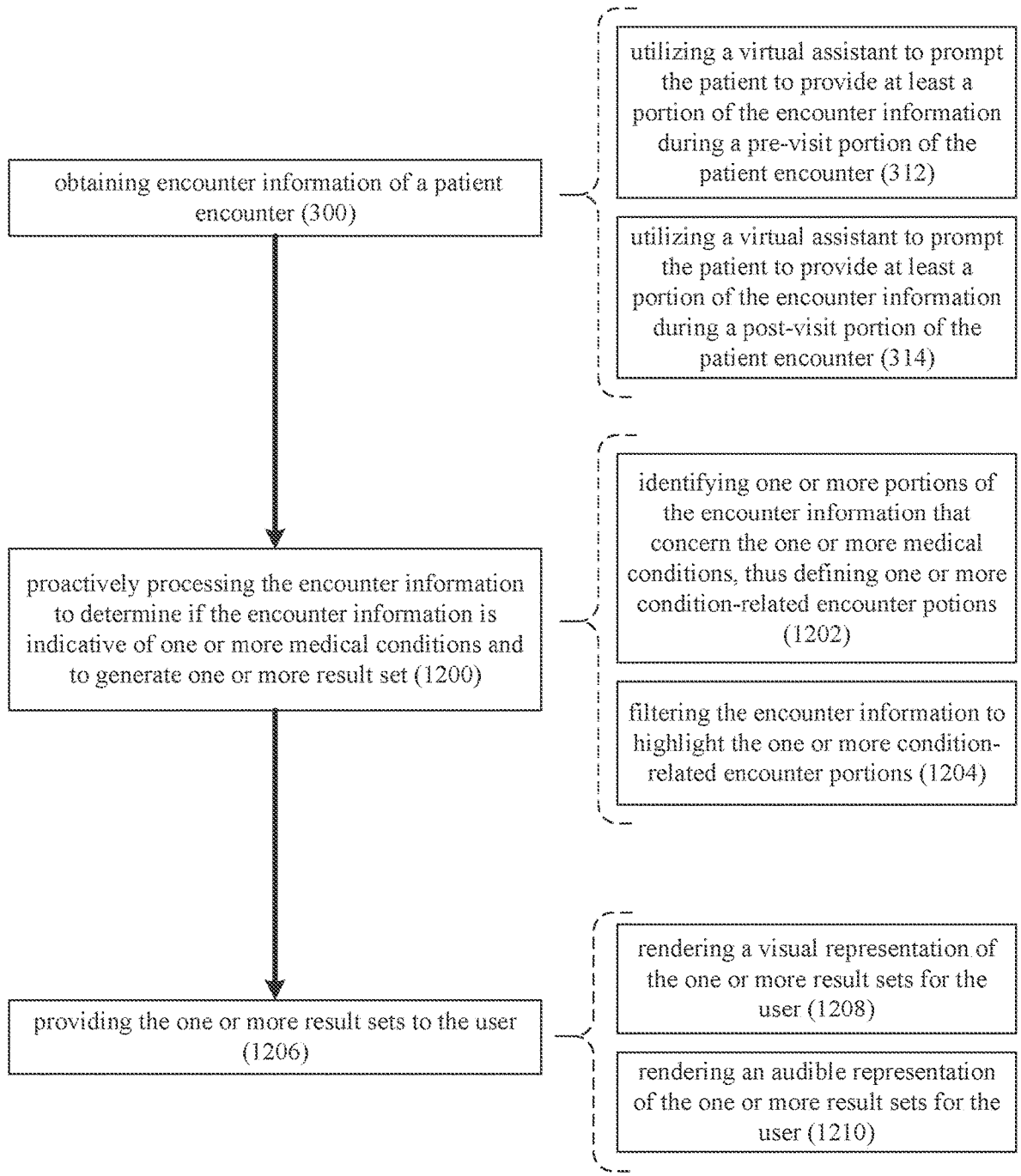
FIG. 24 is a flow chart of another implementation of the automated clinical documentation process of FIG. 1.

Accordingly and referring also to FIG. 24, automated clinical documentation process 10 may be configured to obtain 300 encounter information (e.g., machine vision encounter information 102 and/or audio encounter information 106) of a patient encounter (e.g., a visit to a doctor's office).

As discussed above, virtual assistant 238 may be configured to aid medical professionals (e.g., doctors, nurses, physician's assistants, lab technicians, physical therapists, scribes (e.g., a transcriptionist) and/or staff members involved in the patient encounter) with the gathering of encounter information (e.g., machine vision encounter information 102 and/or audio encounter information 106) during various portions of the patient encounter (e.g., encounter participant 228 visiting the doctor's office).

Accordingly and when obtaining 300 encounter information (e.g., machine vision encounter information 102 and/or audio encounter information 106), automated clinical documentation process 10 may utilize 312 a virtual assistant (e.g., virtual assistant 238) to prompt the patient to provide at least a portion of the encounter information (e.g., machine vision encounter information 102 and/or audio encounter information 106) during a pre-visit portion of the patient encounter (e.g., a visit to a doctor's office).

Further and when obtaining 300 encounter information (e.g., machine vision encounter information 102 and/or audio encounter information 106), automated clinical documentation process 10 may utilize 314 a virtual assistant (e.g., virtual assistant 238) to prompt the patient to provide at least a portion of the encounter information (e.g., machine vision encounter information 102 and/or audio encounter information 106) during a post-visit portion of the patient encounter (e.g., a visit to a doctor's office).

As discussed above, since machine vision system 100 and audio recording system 104 may be positioned throughout monitored space 130, all of the interactions between medical professionals (e.g., encounter participant 226), patients (e.g., encounter participant 228) and third parties (e.g., encounter participant 230) that occur during the patient encounter (e.g., encounter participant 228 visiting the doctor's office) within the monitored space (e.g., monitored space 130) of the clinical environment (e.g., the doctor's office) may be monitored/recorded/processed. Accordingly, a patient "check-in" area within monitored space 130 may be monitored to obtain encounter information (e.g., machine vision encounter information 102 and/or audio encounter information 106) during this pre-visit portion of the patient encounter (e.g., encounter participant 228 visiting the doctor's office). Additionally and as discussed above, this pre-visit encounter information may be obtained via e.g., virtual assistant 238 before the patient (e.g., encounter participant 228) has entered monitored space 130. Further, various rooms within monitored space 130 may be monitored to obtain encounter information (e.g., machine vision encounter information 102 and/or audio encounter information 106) during these various portions of the patient encounter (e.g., while meeting with the doctor, while vital signs and statistics are obtained, and while imaging is performed). Further, a patient "check-out" area within monitored space 130 may be monitored to obtain encounter information (e.g., machine vision encounter information 102 and/or audio encounter information 106) during this post-visit portion of the patient encounter (e.g., encounter participant 228 visiting the doctor's office). Additionally and as discussed above, this post-visit encounter information may be obtained via e.g., virtual assistant 238 after the patient (e.g., encounter participant 228) has left monitored space 130. Further and via machine vision encounter information 102, visual speech recognition (via visual lip reading functionality) may be utilized by automated clinical documentation process 10 to further effectuate the gathering of audio encounter information 106.

Accordingly, a complete recording of the patient encounter (e.g., encounter participant 228 visiting the doctor's office) may be generated, wherein this encounter information (e.g., machine vision encounter information 102 and/or audio encounter information 106) may be processed 302 to generate an encounter transcript (e.g., encounter transcript 234) and at least a portion of this encounter transcript (e.g., encounter transcript 234) may be processed 304 to populate at least a portion of a medical record (e.g., medical record 236) associated with the patient encounter (e.g., the visit to the doctor's office).

Automated clinical documentation process 10 may proactively process 1200 the encounter information (e.g., machine vision encounter information 102 and/or audio encounter information 106) to determine if the encounter information (e.g., machine vision encounter information 102 and/or audio encounter information 106) is indicative of one or more medical conditions and to generate one or more result sets. For example, automated clinical documentation process 10 may continuously (or regularly) scan the encounter information (e.g., machine vision encounter information 102 and/or audio encounter information 106) to determine if this encounter information (e.g., machine vision encounter information 102 and/or audio encounter information 106) is indicative of one or more medical conditions.

As discussed above, ACD compute system 12 may be configured to access one or more datasources 118 (e.g., plurality of individual datasources 120, 122, 124, 126, 128), examples of which may include but are not limited to one or more of a user profile datasource, a voice print datasource, a voice characteristics datasource (e.g., for adapting the automated speech recognition models), a face print datasource, a humanoid shape datasource, an utterance identifier datasource, a wearable token identifier datasource, an interaction identifier datasource, a medical conditions symptoms datasource, a prescriptions compatibility datasource, a medical insurance coverage datasource, and a home healthcare datasource. Accordingly, automated clinical documentation process 10 may proactively access the appropriate datasource to identify the symptoms of various medical conditions (e.g., diabetes) and may compare the identified symptoms of the various medical conditions to the data included within the encounter information (e.g., machine vision encounter information 102 and/or audio encounter information 106).

When proactively processing 1200 the encounter information (e.g., machine vision encounter information 102 and/or audio encounter information 106), automated clinical documentation process 10 may identify 1202 one or more portions of the encounter information (e.g., machine vision encounter information 102 and/or audio encounter information 106) that concern one or more medical conditions, thus defining one or more condition-related encounter portions. Automated clinical documentation process 10 may then filter 1204 the encounter information (e.g., machine vision encounter information 102 and/or audio encounter information 106) to highlight the one or more condition-related encounter portions.

Automated clinical documentation process 10 may provide 1206 the one or more result sets (e.g., result set 1016) to the user (e.g., encounter participant 226). The one or more result sets (e.g., result set 1016) may include: a first result set indicative of a first medical condition; and at least a second result set indicative of at least a second medical condition. For example, while FIG. 20 illustrates a single/consolidated result set, this is for illustrative purpose only and is not intended to be a limitation of this disclosure, as other configurations are possible and are considered to be within the scope of this disclosure. For example, assume that automated clinical documentation process 10 found (within the encounter information) data that indicates that encounter participant 228 may have diabetes and may have heart disease. Accordingly and in such a situation, result set 1016 may include a first result set that is indicative of diabetes and a second result set indicative of heart disease.

When providing 1206 the one or more result sets (e.g., result set 1016) to the user (e.g., encounter participant 226), automated clinical documentation process 10 may render 1208 a visual representation of the one or more result sets (e.g., result set 1016) for the user (e.g., encounter participant 226) and/or may render 1210 an audible representation of the one or more result sets (e.g., result set 1016) for the user (e.g., encounter participant 226).

For example, automated clinical documentation process 10 may provide 1206 result set 1016 to encounter participant 226 in the manner shown in FIG. 20, wherein result set 1016 is visually indicative of the portions of the encounter information that concern a specific medical condition (in this example, diabetes and/or heart disease). Additionally/alternatively, automated clinical documentation process 10 may provide 1206 result set 1016 as a private verbal message (e.g., that is rendered on an earbud worn by encounter participant 226) that provides the information requested by encounter participant 226 (e.g., "There are 23 portions of this patient encounter that indicate that this patient may have diabetes. An A1C test is recommended There are 16 portions of this patient encounter that indicate that this patient may have heart disease. An echocardiogram is recommended."

General:

As will be appreciated by one skilled in the art, the present disclosure may be embodied as a method, a system, or a computer program product. Accordingly, the present disclosure may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, the present disclosure may take the form of a computer program product on a computer-usable storage medium having computer-usable program code embodied in the medium.

Any suitable computer usable or computer readable medium may be utilized. The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium may include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a transmission media such as those supporting the Internet or an intranet, or a magnetic storage device. The computer-usable or computer-readable medium may also be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain, store, communicate, propagate, or transport the program for use by or in connection with the instruction execution system, apparatus, or device. The computer-usable medium may include a propagated data signal with the computer-usable program code embodied therewith, either in baseband or as part of a carrier wave. The computer usable program code may be transmitted using any appropriate medium, including but not limited to the Internet, wireline, optical fiber cable, RF, etc.

Computer program code for carrying out operations of the present disclosure may be written in an object oriented programming language such as Java, Smalltalk, C++ or the like. However, the computer program code for carrying out operations of the present disclosure may also be written in conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through a local area network/a wide area network/the Internet (e.g., network 14).

The present disclosure is described with reference to flowchart illustrations and/or block diagrams of methods, apparatus (systems) and computer program products according to embodiments of the disclosure. It will be understood that each block of the flowchart illustrations and/or block diagrams, and combinations of blocks in the flowchart illustrations and/or block diagrams, may be implemented by computer program instructions. These computer program instructions may be provided to a processor of a general purpose computer/special purpose computer/other programmable data processing apparatus, such that the instructions, which execute via the processor of the computer or other programmable data processing apparatus, create means for implementing the functions/acts specified in the flowchart and/or block diagram block or blocks.

These computer program instructions may also be stored in a computer-readable memory that may direct a computer or other programmable data processing apparatus to function in a particular manner, such that the instructions stored in the computer-readable memory produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions/acts specified in the flowchart and/or block diagram block or blocks.

The flowcharts and block diagrams in the figures may illustrate the architecture, functionality, and operation of possible implementations of systems, methods and computer program products according to various embodiments of the present disclosure. In this regard, each block in the flowchart or block diagrams may represent a module, segment, or portion of code, which comprises one or more executable instructions for implementing the specified logical function (s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustrations, and combinations of blocks in the block diagrams and/or flowchart illustrations, may be implemented by special purpose hardware-based systems that perform the specified functions or acts, or combinations of special purpose hardware and computer instructions.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. The embodiment was chosen and described in order to best explain the principles of the disclosure and the practical application, and to enable others of ordinary skill in the art to understand the disclosure for various embodiments with various modifications as are suited to the particular use contemplated.

A number of implementations have been described. Having thus described the disclosure of the present application in detail and by reference to embodiments thereof, it will be apparent that modifications and variations are possible without departing from the scope of the disclosure defined in the appended claims.

What is claimed is:

1. A computer-implemented method for synchronizing machine vision and audio, executed on a computing device, comprising:
    obtaining encounter information of a patient encounter, wherein the encounter information includes machine vision encounter information and audio encounter information, wherein obtaining encounter information includes utilizing a virtual assistant to prompt an encounter participant to provide at least one of a pre-visit portion of the patient encounter and a post-visit portion of the patient encounter, wherein the virtual assistant verbally prompts the encounter participant to provide at least one of the pre-visit portion of the patient encounter and the post-visit portion of the patient encounter;

temporally aligning the machine vision encounter information and the audio encounter information to produce a temporally-aligned encounter recording;

receiving a user selection of at least a portion of the temporally-aligned encounter information to be rendered, wherein at least the portion of the temporally-aligned encounter recording selected by the user is the at least one of the pre-visit portion of the patient encounter obtained by the virtual assistant and the post-visit portion of the patient encounter obtained by the virtual assistant; and rendering, visually, only the user selection of at least the portion of the temporally-aligned encounter recording selected by the user to include an indication of each of the portions of the audio encounter information during which the encounter participant of the patient encounter speaks in the pre-visit portion of the patient encounter when the pre-visit portion of the patient encounter is selected by the user, and rendering, visually, only the user selection of at least the portion of the temporally-aligned encounter recording selected by the user to include an indication of each of the portions of the audio encounter information during which the encounter participant of the patient encounter speaks in the post-visit portion of the patient encounter when the post-visit portion of the patient encounter is selected by the user.

2. The computer-implemented method of claim 1 wherein the machine vision encounter information is obtained via one or more machine vision systems.

3. The computer-implemented method of claim 2 wherein the one or more machine vision systems includes one or more of:
an RGB imaging system;
an infrared imaging system;
an ultraviolet imaging system;
a laser imaging system;
an X-ray imaging system;
a SONAR imaging system;
a RADAR imaging system; and
a thermal imaging system.

4. The computer-implemented method of claim 1 wherein the audio encounter information is obtained via one or more audio sensors.

5. The computer-implemented method of claim 1 wherein the indication of each of the portions of the audio encounter information during which the encounter participant of the patient encounter speaks is a visual indication of a display of each of the portions of the audio encounter information in at least the portion of the temporally-aligned encounter recording being rendered.

6. The computer-implemented method of claim 5 wherein the visual indication of each of the portions of the audio encounter information during which the encounter participant speaks is distinguished from the audio encounter information during which another encounter participant of the patient encounter speaks.

7. A computer program product residing on a non-transitory computer readable medium having a plurality of instructions stored thereon which, when executed by a processor, cause the processor to perform operations comprising:
obtaining encounter information of a patient encounter, wherein the encounter information includes machine vision encounter information and audio encounter information, wherein obtaining encounter information includes utilizing a virtual assistant to prompt an encounter participant to provide at least one of a pre-visit portion of the patient encounter and a post-visit portion of the patient encounter, wherein the virtual assistant verbally prompts the encounter participant to provide at least one of the pre-visit portion of the patient encounter and the post-visit portion of the patient encounter;

temporally aligning the machine vision encounter information and the audio encounter information to produce a temporally-aligned encounter recording;

receiving a user selection of at least a portion of the temporally-aligned encounter information to be rendered, wherein at least the portion of the temporally-aligned encounter recording selected by the user is the at least one of the pre-visit portion of the patient encounter obtained by the virtual assistant and the post-visit portion of the patient encounter obtained by the virtual assistant; and rendering, visually, only the user selection of at least the portion of the temporally-aligned encounter recording selected by the user to include an indication of each of the portions of the audio encounter information during which the encounter participant of the patient encounter speaks in the pre-visit portion of the patient encounter when the pre-visit portion of the patient encounter is selected by the user, and rendering, visually, only the user selection of at least the portion of the temporally-aligned encounter recording selected by the user to include an indication of each of the portions of the audio encounter information during which the encounter participant of the patient encounter speaks in the post-visit portion of the patient encounter when the post-visit portion of the patient encounter is selected by the user.

8. The computer program product of claim 7 wherein the machine vision encounter information is obtained via one or more machine vision systems.

9. The computer program product of claim 7 wherein the one or more machine vision systems includes one or more of:
an RGB imaging system;
an infrared imaging system;
an ultraviolet imaging system;
a laser imaging system;
an X-ray imaging system;
a SONAR imaging system;
a RADAR imaging system; and
a thermal imaging system.

10. The computer program product of claim 7 wherein the audio encounter information is obtained via one or more audio sensors.

11. The computer program product of claim 7 wherein the indication of each of the portions of the audio encounter information during which the encounter participant of the patient encounter speaks is a visual indication of a display of each of the portions of the audio encounter information in at least the portion of the temporally-aligned encounter recording being rendered.

12. The computer program product of claim 11 wherein the visual indication of each of the portions of the audio encounter information during which the encounter participant speaks is distinguished from the audio encounter information during which another encounter participant of the patient encounter speaks.

13. A computing system including a processor and memory configured to perform operations comprising:

obtaining encounter information of a patient encounter, wherein the encounter information includes machine vision encounter information and audio encounter information, wherein obtaining encounter information includes utilizing a virtual assistant to prompt an encounter participant to provide at least one of a pre-visit portion of the patient encounter and a post-visit portion of the patient encounter, wherein the virtual assistant verbally prompts the encounter participant to provide at least one of the pre-visit portion of the patient encounter and the post-visit portion of the patient encounter;

temporally aligning the machine vision encounter information and the audio encounter information to produce a temporally-aligned encounter recording;

receiving a user selection of at least a portion of the temporally-aligned encounter information to be rendered, wherein at least the portion of the temporally-aligned encounter recording selected by the user is the at least one of the pre-visit portion of the patient encounter obtained by the virtual assistant and the post-visit portion of the patient encounter obtained by the virtual assistant; and rendering, visually, only the user selection of at least the portion of the temporally-aligned encounter recording selected by the user to include an indication of each of the portions of the audio encounter information during which the encounter participant of the patient encounter speaks in the pre-visit portion of the patient encounter when the pre-visit portion of the patient encounter is selected by the user, and rendering, visually, only the user selection of at least the portion of the temporally-aligned encounter recording selected by the user to include an indication of each of the portions of the audio encounter information during which the encounter participant of the patient encounter speaks in the post-visit portion of the patient encounter when the post-visit portion of the patient encounter is selected by the user.

14. The computing system of claim 13 wherein the machine vision encounter information is obtained via one or more machine vision systems.

15. The computing system of claim 14 wherein the one or more machine vision systems includes one or more of:
 an RGB imaging system;
 an infrared imaging system;
 an ultraviolet imaging system;
 a laser imaging system;
 an X-ray imaging system;
 a SONAR imaging system;
 a RADAR imaging system; and
 a thermal imaging system.

16. The computing system of claim 13 wherein the audio encounter information is obtained via one or more audio sensors.

17. The computing system of claim 13 wherein the indication of each of the portions of the audio encounter information during which the encounter participant of the patient encounter speaks is a visual indication of a display of each of the portions of the audio encounter information in at least the portion of the temporally-aligned encounter recording being rendered.

18. The computing system of claim 17 wherein the visual indication of each of the portions of the audio encounter information during which the encounter participant speaks is distinguished from the audio encounter information during which another encounter participant of the patient encounter speaks.

* * * * *